US007794933B1

(12) United States Patent
Lanchbury et al.

(10) Patent No.: US 7,794,933 B1
(45) Date of Patent: Sep. 14, 2010

(54) DEPRESSION-RELATED GENE

(75) Inventors: Jerry Lanchbury, Salt Lake City, UT (US); Alexander Gutin, Sandy, UT (US); Kirsten Timms, Salt Lake City, UT (US); Andrey Zharkikh, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 540 days.

(21) Appl. No.: 11/326,603

(22) Filed: Jan. 4, 2006

Related U.S. Application Data

(60) Provisional application No. 60/641,182, filed on Jan. 4, 2005.

(51) Int. Cl.
    *C12Q 1/68* (2006.01)
(52) U.S. Cl. ......................................................... 435/6
(58) Field of Classification Search ........................ None
    See application file for complete search history.

(56) References Cited

U.S. PATENT DOCUMENTS

| 5,736,323 | A |   | 4/1998  | Soubrier et al. |      |
|-----------|---|---|---------|-----------------|------|
| 5,773,220 | A |   | 6/1998  | DeKosky et al.  |      |
| 5,942,390 | A |   | 8/1999  | Cominelli et al.|      |
| 5,994,080 | A |   | 11/1999 | Grobbee et al.  |      |
| 2003/0220224 | A1 | * | 11/2003 | Davison et al. | 514/1 |
| 2005/0209181 | A1 | * | 9/2005  | Akil et al.    | 514/44 |

FOREIGN PATENT DOCUMENTS

WO    WO2004-108899    12/2004

OTHER PUBLICATIONS

"Introduction". Merck Manuals online medical library. Nov. 2005. URL: http://www.merck.com/mmpe/sec15/ch200/ch200a.html.*
"Depressive Disorders". Merck Manuals online medical library. Nov. 2005. URL: http://www.merck.com/mmpe/sec15/ch200/ch200b.html.*
Detera-Wadleigh, et al. International Review of Psychiatry, 2004; 16(4):301-310.*
Green, et al. British Journal of Psychiatry, 2006; 188:21-25.*
Witczak, et al. EMBO Journal, 1999; 18(7):1858-1868.*
GenBank Accession No. AJ131693, Apr. 24, 1999.*
Nestler et al. (Neuron Mar. 28, 2002 vol. 34 p. 13).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
NCBI, GenBank: AY528715.
NCBI, EST: AW439271.
Arnaud et al., "Polymorphisms in the 5' Regulatory Region of the Tissue Factor Gene and the Risk of Myocardial Infarction and Venous Thromboembolism", *Arteriosclerosis, Thrombosis, and Vascular Biology*, 2000, 20:892-898.
Baron et al., "Genetic linkage between X-chromosome markers and bipolar affective illness", *Nature*, Mar. 19, 1987, 326(6110):289-292.
Baron et al., "X-Linkage and Manic-Depressive Illness: A Reassessment", *Social Biology*, 1991, 38(3-4):179-188.
Berrettini et al., "Chromosome 18 DNA markers and manic-depressive illness: Evidence for a susceptibility gene", *Proc. Natl. Acad. Sci.*, Jun. 1994, 91:5918-5921.
Bertina et al., "Mutation in blood coagulation factor V associated with resistance to activated protein C", *Nature*, May 5, 1994, 369:64-67.
Blackwood et al., "A locus for bipolar affective disorder on chromosome 4p", *Nature Genetics*, Apr. 1996, 12:427-430.
Craddock et al., "Genetics of bipolar disorder", *Journal of Medical Genetics*, Aug. 1999, 36:585-594.
Craddock et al., "Molecular genetics of bipolar disorder", *British Journal of Psychiatry*, 2001, 178(suppl. 41):s128-s133.
Dawson et al., "Linkage Studies of Bipolar Disorder in the Region of the Darier's Disease Gene on Chromosome 12q23-24.1", *American Journal of Medical Genetics*, Apr. 24, 1995, 60(2):94-102.
Degn et al., "Further evidence for a bipolar risk gene on chromosome 12q24 suggested by investigation of haplotype sharing and allelic association in patients from the Faroe Islands", *Molecular Psychiatry*, 2001. 6:450-455.
Detera-Wadleigh et al., "A high-density genome scan detects evidence for a bipolar-disorder susceptibility locus on 13q32 and other potential loci on 1q32 and 18p11.2", *Proc Natl Acad Sci*, May 1999, 96:5604-5609.
Detera-Wadleigh et al., "Chromosomes 12 and 16 workshop", *American Journal of Medical Genetics*, Jun. 18, 1999, 88(3):255-259.
Diviani et al., "AKAP signaling complexes at the cytoskeleton", *Journal of Cell Science*, 114:1431-1437.
Drazen et al., "Pharmacogenetic association between ALOX5 promoter genotype and the response to anti-asthma treatment", *Nature Genetics*, Jun. 1999, 22:168-170.
Egeland et al, "Bipolar affective disorders linked to DNA markers on chromosome 11", *Nature*, Feb. 26, 1987, 325(6107):783-787.
Ewald et al., "Significant linkage between bipolar affective disorder and chromosome 12q24", *Psychiatric Genetics*, Autumn 1998, 8(3):131-140.
Freimer et al., "Genetic mapping using haplotype, association and linkage methods suggests a locus for severe bipolar disorder (BPI) at 18q22-q23", *Nature Genetics*, Apr. 1996, 12:436-441.
Greenberg et al., "The Economic Burden of Depression in the United States: How Did It Change Between 1990 and 2000?", *Journal of Clinical Psychiatry*, Dec. 2003, 64(12):1465-1475.
Hayashi et al., "A novel mutation at the donor splice site of intron 3 of the GH-I gene in a patient with isolated growth hormone deficiency", *Growth Hormone & IGF Research*, 1999, 9:434-437.

(Continued)

Primary Examiner—Sarae Bausch
Assistant Examiner—Katherine Salmon
(74) Attorney, Agent, or Firm—Benjamin G. Jackson; Jay Z. Zhang; Myriad Genetics IP Department

(57) ABSTRACT

The invention relate to the discovery of a depression associated AKAP9 predisposing variant. The invention provides for detecting the variant. The invention also provides methods for screening for antidepressants based on modulating AKAP9 mediated signaling.

1 Claim, No Drawings

OTHER PUBLICATIONS

Jacobsen et al., "Association study of bipolar disorder at the phospholipase A2 gene (PLA2A) in the Darier's disease (DAR) region of chromosome 12q23-q24.1", *Psychiatric Genetics*, Winter 1996, 6(4):195-199.

Kelsoe et al, "Re-evaluation of the linkage relationship between chromosome 11p loci and the gene for bipolar affective disorder in the Old Order Amish", *Nature*, Nov. 16, 1989, 342(6247):238-243.

Krynetski et al., "Pharmacogenetics as a Molecular Basis for Individualized Drug Therapy: The Thiopurine S-methyltransferase Paradigm", *Pharmaceutical Research*, 1999, 16(3):342-349.

McCarthy et al., "The use of single-nucleotide polymorphism maps in pharmacogenomics", *Nature Biotechnology*, May 2000, 18(5):505-508.

McGuigan et al., "Susceptibility to Osteoporotic Fracture is Determined by Allelic Variation at the Sp1 Site, Rather than Other Polymorphic Sites at the COL1A1 Locus", *Osteoporosis International*, 2000, 11(4):338-343.

Morissette et al., "Genome Wide Search for Linkage of Bipolar Affective Disorders in a Very Large Pedigree Derived From a Homogeneous Population in Quebec Points to a Locus of Major Effect on Chromosome 12q23-q24", *American Journal of Medical Genetics*, Oct. 15, 1999, 88(5):567-587.

Nebert, "Invited Editorial Polymorphisms in Drug-Metabolizing Enzymes: What Is Their Clinical Relevance and Why Do They Exists?", *American Journal Human Genetics*, 1997, 60:265-271.

Nemer, et al., "Organization of the Human *LU* Gene and Molecular Basis of the $Lu^a/Lu^b$ Blood Group Polymorphism", *Blood*, Jun. 15, 1997, 89(12):4608-4616.

Otterness et al., "Human Thiopurine Methyltransferase Pharmacogenetics, Kindred with a Terminal Exon Splice Junction Mutation That Results in Loss of Activity", *Journal of Clinical Investigation*, Mar. 1998, 101(5):1036-1044.

Pekkarinen et al., "Evidence of a Predisposing Locus to Bipolar Disorder on Xq24-q27.1 in an Extended Finnish Pedigree", *Genome Research*, 1995, 5:105-115.

Puga et al., "Genetic Polymorphisms in Human Drug-Metabolizing Enzymes: Potential Uses of Reverse Genetics to Identify Genes of Toxicological Relevance", *Critical Reviews in Toxicology*, 1997, 27(2):199-222.

Rice et al., "Initial Genome Scan of the NIMH Genetics Initiative Bipolar Pedigrees: Chromosomes 1, 6, 8, 10, and 12" *American Journal of Medical Genetics*, May 1997, 74(3):247-253.

Rice et al., "The Familial Transmission of Bipolar Illness", *Arch Gen Psychiatry*, May 1987, 44(5):441-447.

Shen et al., "Single-nucleotide polymorphisms can cause different structural folds of mRNA", PNAS, Jul. 1999, 96:7871-7876.

Spence et al., "Bipolar Disorder: Evidence for a Major Locus", *American Journal of Medical Genetics (Neuropsychiatric Genetics)*, Oct. 9, 1995, 60(5):370-376.

States et al., "Splice site mutations in a xeroderma pigmentosum group A patient with delayed onset of neurological disease", *Mutation Research*, Aug. 8, 1996, 363(3):171-177.

Straub et al., "A possible vulnerability locus for bipolar affective disorder on chromosome 21q22.3", *Nature Genetics*, Nov. 1994, 8:291-296.

Tsai et al., "Identification of a Splice Site Mutation in the Cystathionine β-Synthase Gene Resulting in Variable and Novel Splicing Defects of Pre-mRNA", *Biochemical and Molecular Medicine*, 1997, 61(1):9-15.

Wong et al., "AKAP Signalling Complexes: Focal Points in Space and Time", *Molecular Cell Biology*, Dec. 2004, 5:959-970.

Yan et al. "Childhood-Onset Schizophrenia/Autistic Disorder and t(1;7) Reciprocal Translocation: Identification of a BAC Contig Spanning the Translocation Breakpoint at 7q21", *American Journal of Medical Genetics*, 2000, 96:749-753.

Yu et al., "Familial hypercholesterolemia. Acceptor splice site (G→C) mutation in intron 7 of the LDL-R gene: alternate RNA editing causes exon 8 skipping or a premature stop condon in exon 8", *Atherosclerosis*, 1999, 146:125-131.

\* cited by examiner

DEPRESSION-RELATED GENE

CROSS-REFERENCE TO RELATED APPLICATIONS

This application claim priority under 35 U.S.C. §119(e) to U.S. provisional application No. 60/641,182 filed Jan. 4, 2005, which is incorporated herein by reference in its entirety.

SEQUENCE LISTING

The instant application was filed with an informal Sequence Listing that has been replaced by a formal Sequence Listing submitted electronically as a text file. This text file, which was named "1318-01-2U 2007-09-18 Amended Formal Sequence Listing (TXT FILE) BGJ.ST25.txt", was created on Sep. 18, 2007, and is 93,994 bytes in size. Its contents are incorporated by reference herein in their entirety.

FIELD OF THE INVENTION

The invention relates to depression. In particular, the invention relates to a gene associated with depression and altered forms of the gene. The invention provides methods for predicting depression, predicting susceptibility to depression, and screening for drugs capable of treating depression.

BACKGROUND OF THE INVENTION

Genetic polymorphic variations such as SNPs are valuable tools for deciphering mechanisms of biological functions and understanding the underlying basis of human diseases. See generally, Cooper et al. in The Metabolic and Molecular Bases of Inherited Diseases, 1:259-291 (1995), Scriver et al., eds., McGraw-Hill, New York. Single-nucleotide polymorphisms (SNPs) are small variations in genomes. They are among the most common forms of human genetic variations. A large number of monogenic human diseases are associated with genetic polymorphic variations such as SNPs in the so-called susceptibility genes. For example, polymorphic variations in the coagulation factor gene F5 have been linked directly to deep-vein thrombosis. See Bertina et al., Nature, 369:64-67 (1994). SNPs in the Apolipoprotein E gene correlate with the risk of Alzheimer's disease. See U.S. Pat. No. 5,773,220.

Genetic polymorphic variations are also associated with varying response to drugs and natural environmental agents. See generally, McCarthy et al., Nat. Biotechnol., 18:505-508 (2000); Nebert, Am. J. Hum. Genet. 60:265-271 (1997); and Puga et al., Crit. Rev. Toxicol. 27(2):199-222 (1997). Pharmacogenomic studies have found a large number of SNPs responsible for differing drug response. For example, variants in the 5-lipoxygenase gene, which codes for an anti-asthma drug target, have been linked to variations in drug response. See Drazen et al., Nat. Genet. 22:168-170 (1999). In addition, genetic variants in the drug-metabolizing enzyme thiopurine methyltransferase correlate with adverse drug reactions. See Krynetski et al., Pharm. Res., 16:342-349 (1999).

Since proteins are intimately involved in essential biological functions and drug metabolism, the apparent nexus between genetic polymorphic variations and human diseases and drug response is not at all surprising because any gene sequence changes may potentially affect gene expression and protein functions. For example, SNPs in exons may lead to different protein sequences exhibiting altered protein activities (e.g., sickle cell anemia). SNPs in exons and thus mRNAs may also affect the splicing, processing, transport, translation, or stability of the mRNAs. See e.g., Cooper et al., in The Metabolic and Molecular Bases of Inherited Diseases, 1:259-291 (1995), Scriver et al., eds., McGraw-Hill, New York. SNPs in exons may also alter mRNA secondary or tertiary structures, i.e., mRNA folding, and thus affect post-transcriptional gene regulation. See Shen et al., Proc. Natl. Acad. Sci. USA, 96:7871-7876 (1999).

Polymorphic variations in non-coding regions have also been linked to diseases and other phenotypic effects. For example, SNPs in introns can affect mRNA splicing and thus alter gene expression. See e.g., Otterness et al., J. Clin. Invest., 101(5):1036-44 (1998); Hayashi et al., Growth Horm. IGF Res., 9:434-437 (1999); Tsai et al., Biochem. Mol. Med., 61:9-15 (1997); Yu et al., Atherosclerosis, 146:125-31 (1999); Nemer et al., Blood, 89:4608-16 (1997); States et al., Mutat. Res., 363:171-7 (1996). Genetic variations in intronic sequences may also influence gene transcription or interactions between gene transcription products and other cellular machines. Likewise, polymorphic variations in transcriptional regulatory regions of a gene may alter transcription pattern of the gene. See McGuigan et al., Osteoporos. Int., 11:338-43 (2000); Arnaud et al., Arterioscler. Thromb. Vasc. Biol., 20:892-898 (2000).

Very often, a genetic polymorphic variant alone does not cause any detectable effect on gene expression or gene function. However, it may act in concert with other known or unknown polymorphic variants in the gene and cause cumulative or synergistic effect sufficient to alter gene expression pattern or the properties of the protein encoded by the gene. Even if a particular genetic polymorphic variant does not contribute to any changes in gene expression or protein function, it may be near or linked to one or more other genetic variants that directly cause phenotypic defects. Therefore, by identifying such genetic variants, one could reasonably predict the phenotypic effect in an individual having such genetic variants. In addition, one can also identify haplotypes, that is, combinations of genetic variants in a particular gene or chromosome present in an individual. Haplotypes represent patterns of genetic variations and are important tools for genetic analysis and diagnosis.

Indeed, genetic polymorphic variations such as SNPs and haplotypes containing SNPs are invaluable genetic markers for a variety of applications. For example, genetic polymorphic variations are useful in genetic analysis for studying polymorphic allele segregation and polymorphism origins. In addition, genetic polymorphisms can be used as markers in population study, and in forensic medicine. More importantly, SNPs can be particularly useful in genetic diagnosis for identifying individuals predisposed to certain diseases. See e.g., U.S. Pat. Nos. 5,994,080, 5,942,390, 5,773,220, and 5,736,323. Further, SNPs can also be valuable tools for predicting an individual's response to drug treatment or other exogenous interventions.

Thus, there is need in the art to identify additional SNPs, particularly those associated with defined phenotypes like depression and/or neurological disorders.

Depression is thought to affect around twenty million Americans every year. The economic impact of depression is difficult to estimate, but reports indicate that the disease was responsible for an economic burden of approximately 44-52 billion dollars in 1990 and 83 billion dollars in 2000, in the United States alone (Greenberg et al. J. Clin. Psy. 23:1465-75 (2003)). Depression manifests itself in many different ways including persistent sad mood, loss of interest or pleasure in once enjoyable activities, significant change in appetite or body weight, sleep disorders, physical slowing or agitation, loss of energy, feelings of worthlessness, inappropriate guilt, difficulty thinking, difficulty concentrating, malaise, and recurrent thoughts of death or suicide. The families and friends of depressed individuals are often profoundly affected by the disease.

Depression is typically diagnosed as major depressive disorder (unipolar major depression, bipolar disorder (manic-depressive illness), and dysthymic disorder (dysthymia). There are a number of subtypes of these major categories of depression. Diagnosis of these mental disorders is based on the Diagnostic and Statistical Manual of Mental Disorders, fourth edition (DSM-IV) (American Psychiatric Association; Diagnostic and Statistical Manual of Mental Disorders, fourth edition (DSM-IV), Washington, D.C., American Psychiatric Press, 1994).

Major depression is associated with low mood, low energy and motivation, insomnia, and feelings of worthlessness and hopelessness. Bipolar disorder is a severe psychiatric disorder that affects approximately 1% of the world's population (Goodwin, F. K. and Jameson, K. R. Manic-Depressive Illness, Oxford Univ. Press, New York (1990)). It is characterized by extreme swings in mood between mania and depression. Mania is accompanied by euphoria, grandiosity, increased energy, decreased need for sleep, rapid speech, and risk taking. Psychosis can occur in either state, and there is a 17% lifetime risk for suicide. Dysthymic disorder is considered a milder form of depression with symptom similar to that of major depression.

The etiology of depression is currently unknown, but epidemiological studies argue for a strong genetic component. Family studies indicate an approximately 7-fold increase in risk to first-degree family members (Tsuang, M. T. and Faraone, S. V. (1990) The Genetics of Mood Disorders, Johns Hopkins Univ. Press, Baltimore). Twin studies find an average 4-fold increase in risk to monozygotic vs. dizygotic twins. The mode of genetic transmission is unclear. Although some studies have supported the presence of autosomal dominant major loci (Spence, M. A. et al. *Am. J. Med. Genet.* 60:370-376 (1995); Rice, J. et al *Arch. Gen. Psychiatry* 44:441-447 (1987)), it has also been argued that bipolar disorder is oligogenic with multiple loci of modest effect.

Although initial attempts at linkage studies met with inconsistent replication (Egeland, J. A. et al. *Nature* 325:783-787 (1987); Kelsoe, J. R. et al. *Nature* 342:238-243 (1989); Baron, M. et al. Nature 326:289-292 (1987); Baron, M. *Soc. Biol.* 38:179-188 (1991)), more recently, the accumulation of multiple studies of larger family sets has led to the reproducible identification of several genetic loci associated with depression. These include 4p, 12q, 13q, 18, 21q, and Xq among others (Blackwood, D. H. et al. *Nat. Genet.* 12:427-430 (1996); Dawson, E. et al. *Am. J. Med. Genet.* 60:94-102 (1995); Detera-Wadleigh, S. D. et al. *Proc. Natl. Acad. Sci. USA* 96:5604-5609 (1999); Berrettini, W. H. et al. *Proc. Natl. Acad. Sci. USA* 91:5918-5921 (1994); Freimer, N. B. et al. *Nat. Genet.* 12:436-441 (1996); Straub, R. E. et al. *Nat. Genet.* 8:291-296 (1994); Pekkarinen, P. et al. *Genome Res.* 5:105-115 (1995); Craddock, N. & Jones, I. *J. Med. Genet.* 36:585-594 (1999); Craddock, N. & Jones, I. *Br. J. Psychiatry* 41:s128-s133 (2001)). Linkage between bipolar disorder and chromosome 12q23-12q24 has been reported (Green, E. K. et al. *Am. J. Med. Genet.* 96:545 (2000); Morissette, J. et al. *Am. J. Med. Genet.* 88: 567-587 (1999); Ewald, H. et al. *Psychiatr. Genet.* 8:131-140 (1998); Degan, B. et al. *Mol. Psychiatry* 6:450-455 (2001); Detera-Wadleigh, S. D. et al. *Am. J. Med. Genet.* 88:255-259 (1999); Jacobsen, N. et al. *Psych. Genet.* 6:195-199 (1996); Rice, J. P. et al. *Am. J. Med. Genet.* 74:247-253 (1997)).

In view of the economic and emotional costs associated with depression, there is a need to identify genes associated with depression for diagnostic and therapeutic purposes.

The present invention relates generally to depression. More specifically, the present invention relates to a human depression predisposing gene, specifically the AKAP9 (A-Kinase Anchor Protein 9) gene, a mutant allele of which is associated with susceptibility or predisposition to depression. More specifically, the invention relates to a single nucleotide polymorphism within the AKAP9 gene and its use in the diagnosis of predisposition to depression. The invention also relates to the prophylaxis and/or therapy of depression associated with altered AKAP9. The invention further relates to the screening of drugs for depression therapy. Drugs which modulate AKAP9 bioactivity are expected to have therapeutic value in depression. Finally, the invention relates to screening the AKAP9 gene for mutations/alterations, which are useful for diagnosing predisposition to depression.

BRIEF SUMMARY OF THE INVENTION

The invention is related to the discovery of a mutation in the AKAP9 gene and its association with a susceptibility to depression. During the course of experiments designed to identify single nucleotide polymorphisms (SNPs) associated with heritable mRNA expression profiles, the inventors identified a polymorphism in AKAP9 that was associated with a heritable mRNA profile. Subsequent DNA sequencing of AKAP9 in a population with and without major depression revealed that a SNP in the AKAP9 gene is associated with major depression. This SNP results in a missense mutation, changing a lysine (K) residue to an arginine (R) residue. The association of an altered AKAP9 with depression provides for new methods of detecting predisposition to depression and allows for the development of therapeutics that modify AKAP9 mediated signaling for treating depression.

In a first aspect, the invention provides a method for detecting, in an individual, a susceptibility to depression. Thus, the present invention provides methods for determining whether a subject is at risk for developing depression due to a mutation in the AKAP9 gene. This method relies on the discovery that an AKAP9 SNP was correlated with depression. It will be understood by those of skill in the art, given the disclosure of the invention, that a variety of methods can be utilized to detect a mutation in the AKAP9 gene, including the SNP disclosed herein, which is associated with a susceptibility to depression.

The method can include detecting, in a sample from an individual, the presence or absence of a polymorphism in the AKAP9 gene. The detection of a polymorphism in the AKAP9 gene can include ascertaining the existence of at least one of: a deletion of one or more nucleotides; an addition of one or more nucleotides, a substitution of one or more nucleotides; a gross chromosomal rearrangement; an alteration in the level of a messenger RNA transcript; the presence of a non-wild type splicing pattern of a messenger RNA transcript; a non-wild type level of an AKAP9 protein; and/or an aberrant level of an AKAP9 protein.

For example, detecting the polymorphism can include (i) providing a probe/primer comprised of an oligonucleotide which hybridizes to a sense or antisense sequence of an AKAP9 gene or naturally occurring mutants thereof, or 5' or 3' flanking sequences naturally associated with an AKAP9 gene; (ii) contacting the probe/primer to an appropriate nucleic acid containing sample; and (iii) detecting, by hybridization of the probe/primer to the nucleic acid, the presence or absence of the polymorphism, wherein detecting the polymorphism comprises utilizing the probe/primer to determine the nucleotide sequence of an AKAP9 gene and, optionally, of the flanking nucleic acid sequences. For instance, the primer can be employed in a polymerase chain reaction (PCR), in a ligase chain reaction (LCR) or other amplification reactions known to a skilled artisan. In alternate embodiments, the level of an AKAP9 protein is detected in an immunoassay using an antibody which is specifically immunoreactive with the AKAP9 protein. In another embodiment, antibodies specific to AKAP9 mutants are used to determine AKAP9 for diagnostic purposes.

In a second aspect of the invention, compounds that are agonists or antagonists of a normal (functional) AKAP9 bioactivity and their use in preventing or treating depression are provided. For example, to ameliorate disease symptoms involving insufficient expression of an AKAP9 gene and/or inadequate amount of functional AKAP9 bioactivity in a subject, a gene therapeutic (comprising a gene encoding a functional AKAP9 protein) or a protein therapeutic (comprising a functional AKAP9 protein or fragment thereof) can be administered to the subject. Alternatively, agonists or antagonists of AKAP9 function (wild-type or mutant) or an AKAP9 receptor or a receptor for a fragment of AKAP9 can be administered.

In a third aspect of the invention, compounds that are antagonists of a disease causing AKAP9 bioactivity and their use in preventing or treating depression are provided. For example, to ameliorate disease symptoms involving expression of a mutant AKAP9 gene or aberrant expression of a normal AKAP9 gene in a subject, a therapeutically effective amount of an antisense, ribozyme, siRNA, or triple helix molecule to reduce or prevent gene expression may be administered to the subject. Alternatively, to ameliorate disease symptoms involving the regulation via an AKAP9 protein or AKAP9 protein fragments of an upstream or downstream element in an AKAP9 mediated biochemical pathway (e.g., signal transduction), a therapeutically effective amount of an agonist or antagonist compound (e.g., small molecule, peptide, peptidomimetic, protein or antibody) that can prevent normal binding of the wild-type AKAP9 protein, can induce a therapeutic effect.

In a fourth aspect of the invention, assays, e.g., screening compounds to identify antagonists (e.g., inhibitors), or alternatively, agonists (e.g., potentiators), of an interaction between an AKAP9 protein and, for example, a protein or nucleic acid that binds to the AKAP9 protein or fragments of AKAP9 are provided. An exemplary method includes the steps of (i) combining an AKAP9 polypeptide or bioactive fragments thereof, an AKAP9 target molecule (such as an AKAP9 receptor, ligand, or interacting protein partner), and a test compound, e.g., under conditions wherein, but for the test compound, the AKAP9 protein and AKAP9 target molecule are able to interact; and (ii) detecting the formation of a complex which includes the AKAP9 protein and the target molecule either by directly quantitating the complex or by measuring inductive effects of the AKAP9 protein or fragments of AKAP9 protein. A statistically significant change, such as a decrease, in the interaction of the AKAP9 and AKAP9 target molecule in the presence of a test compound (relative to what is detected in the absence of the test compound) is indicative of a modulation (e.g., inhibition or potentiation of the interaction between the AKAP9 protein or fragments of the AKAP9 protein and the target molecule). The assay of this aspect of the invention can involve determining the effect of a test compound on protein kinase A activity (PKA). For example, a mutant AKAP9, altered AKAP9 levels, or altered AKAP9 mediated signaling can result in altered PKA signaling. Assays can be performed with these altered AKAP9s to determine the effect of a test compound on PKA signaling. In one embodiment, the assay involves (1) providing an altered AKAP9 bioactivity that alters PKA signaling and (2) determining the effect of a test compound on the altered PKA signaling produced by the altered AKAP9 bioactivity. Compounds that modulate an altered AKAP9 via PKA signaling are potential antidepressants.

In a fifth aspect, the present invention provides methods for modulating the transcription of certain genes in a cell by modulating AKAP9 bioactivity, (e.g., by potentiating or disrupting an AKAP9 bioactivity). In general, whether carried out in vivo, in vitro, or in situ, the method comprises treating the cell with an effective amount of an AKAP9 therapeutic (agonist or antagonist of an AKAP9 bioactivity) so as to alter, relative to the cell in the absence of treatment, the level of transcription of certain genes. Accordingly, the method can be carried out with AKAP9 therapeutics such as peptide and peptidomimetics or other molecules identified in the above-referenced drug screens which agonize or antagonize the effects of an AKAP9 bioactivity (e.g., transcription) of a gene which is regulated by an AKAP9 protein. Other AKAP9 therapeutics include antisense or siRNA constructs for inhibiting expression of AKAP9 proteins, and dominant negative mutants of AKAP9 proteins which competitively inhibit interactions between ligands (e.g., proteins) and nucleic acids upstream and downstream of the wild-type AKAP9 protein.

In a sixth aspect, the invention relates to isolated nucleic acids encoding an altered AKAP9. In particular, the invention provides an isolated altered AKAP9 nucleic acid, having the following alteration (in reference to the nucleotides set forth in SEQ ID NO:1): the A at nucleotide position 7673 is substituted with G, or a complement thereof. According to this aspect of the present invention, an isolated human AKAP9 nucleic acid is provided containing the newly discovered genetic polymorphic. The present invention also encompasses an isolated oligonucleotide having a contiguous span of at least 18, preferably from 18 to 50 nucleotides of the sequence of a human AKAP9 gene, wherein the contiguous span encompasses and contains the discovered nucleotide variant.

In a seventh aspect, the invention provides a nucleic acid probe specifically hybridizable to a human altered AKAP9 DNA and not to the corresponding wild-type DNA. According to one embodiment of this aspect of the invention, the altered AKAP9 comprises an alteration of SEQ ID NO:1 or complements thereof, where the A at nucleotide position 7673 is substituted with G, or a complement thereof.

In an eighth aspect, the invention provides a method for diagnosing an alteration which causes or predisposes an individual to depression by hybridizing a probe to an altered (mutant) AKAP9 nucleic acid in a patient's sample of DNA or RNA under stringent conditions which allows hybridization of the probe to nucleic acid comprising the alteration but prevents hybridization of the probe to a wild-type nucleic acid. The presence of a hybridization signal indicates the presence of the alteration. In a preferred embodiment of this aspect of the invention, the method is performed using nucleic acid microchip technology.

In a ninth aspect, the invention provides an isolated altered AKAP9 polypeptide. According to this aspect of the invention, the isolated polypeptide has (in reference to SEQ ID NO:2) the lysine at position 2484 substituted with arginine (K2484R). In another embodiment of this aspect of the invention an antibody capable of binding the altered polypeptide but incapable of binding a wild-type AKAP9 polypeptide is provided. In accordance with this aspect of the invention, an isolated AKAP9 protein or a fragment thereof is provided having the discovered amino acid variant.

In a tenth aspect, the invention provides a method for detecting an alteration in AKAP9 that is associated with depression in a human. Accordingly, the method comprises analyzing an APAP9 gene, or an AKAP9 gene expression product from cells or tissue of a human. In various embodiments of the invention the alteration is detected by immunoblotting, immunocytochemistry, assaying for binding interactions between the gene product isolated from the tissue and a binding partner capable of specifically binding the polypeptide expression product of a mutant allele and/or a binding partner for the polypeptide, or assaying for the inhibition of biochemical activity of the binding partner. In another embodiment of this aspect of the invention, the method involves comparing the sequence of a subject AKAP9 gene with the sequence of one or more wild-type AKAP9 gene sequences to determine if there is an alteration in the subject AKAP9. According to other embodiments of this aspect of the invention, the mutation can be detected by any method including: (a) hybridizing a probe specific for an AKAP9 alterations to RNA isolated from the human sample and detecting the presence of a hybridization product, wherein the presence of the product indicates the presence of an AKAP9 alteration in the sample; (b) hybridizing a probe specific for an AKAP9 alteration to cDNA made from RNA isolated from the sample and detecting the presence of a hybridization product, wherein the presence of the product indicates the presence of an AKAP9 alteration in the sample; (c) hybridizing a probe specific for an AKAP9 alteration to genomic DNA isolated from the sample and detecting the presence of a hybridization product, wherein the presence of the product indicates the presence of the alteration in the sample; (d) amplifying all or part of the gene in the sample using a set of primers to produce amplified nucleic acids and sequencing the amplified nucleic acids to determine if there is an AKAP9 alteration; (e) amplifying part of the gene in the sample using a primer specific for an AKAP9 alteration and detecting the presence of an amplified product, wherein the presence of the product indicates the presence of the alteration in the sample; (f) cloning all or part of the AKAP9 gene in the sample to produce a cloned nucleic acid and sequencing the cloned nucleic acid; (g) amplifying the AKAP9 gene to produce amplified nucleic acids, hybridizing the amplified nucleic acids to a DNA probe specific for an AKAP9 alteration and detecting the presence of a hybridization product, wherein the presence of the product indicates the presence of the alteration; (h) forming single-stranded DNA from a gene fragment of the gene from a human sample and single-stranded DNA from a corresponding fragment of a wild-type gene, electrophoresing the single-stranded DNAs on a non-denaturing polyacrylamide gel and comparing the mobility of the single-stranded DNAs on the gel to determine if the single-stranded DNA from the sample is shifted relative to wild-type and sequencing the single-stranded DNA having a shift in mobility; (i) forming a heteroduplex consisting of a first strand of nucleic acid selected from the group consisting of a genomic DNA fragment isolated from the sample, an RNA fragment isolated from the sample and a cDNA fragment made from mRNA from the sample and a second strand of a nucleic acid consisting of a corresponding human wild-type gene fragment, analyzing for the presence of a mismatch in the heteroduplex, and sequencing the first strand of nucleic acid having a mismatch to determine if there is an AKP9 alteration in the sample; (j) forming single-stranded DNA from the gene of the human sample and from a corresponding fragment of an allele specific for one of the alterations, electrophoresing the single-stranded DNAs on a non-denaturing polyacrylamide gel and comparing the mobility of the single-stranded DNAs on the gel to determine if the single-stranded DNA from the sample is shifted relative to the allele, wherein no shift in electrophoretic mobility of the single-stranded DNA relative to the allele indicates the presence of an AKAP9 alteration in the sample; and (k) forming a heteroduplex consisting of a first strand of nucleic acid selected from the group consisting of a genomic DNA fragment of the gene isolated from the sample, an RNA fragment isolated from the sample and a cDNA fragment made from mRNA from the sample and a second strand of a nucleic acid consisting of a corresponding gene allele fragment specific for one of the alterations and analyzing for the presence of a mismatch in the heteroduplex, wherein no mismatch indicates the presence of the alteration.

In an eleventh aspect, the invention provides a method for determining whether a human subject has or is at risk for developing depression. In one embodiment, the method involves: (a) obtaining a sample from a subject, said sample comprising nucleic acid molecules containing the AKAP9 gene (or fragments thereof); and (b) detecting the presence or absence of a genetic alteration in the gene of said subject, wherein the presence of said genetic alteration identifies a subject that has or is at risk for developing depression. In another embodiment, the alteration (mutation) is A7673G or a complement thereof (referring to SEQ ID NO:1).

In a twelfth aspect, the invention provides a method for preventing or treating depression in a subject which comprises administering to the subject a therapeutically effective amount of a compound that agonizes or antagonizes wild-type AKAP9, or agonizes or antagonizes altered AKAP9, or agonizes or antagonizes an AKAP9 receptor. In one embodiment, the method for preventing or treating depression involves a compound is selected from: (a) a drug; (b) an antisense molecule; (c) an siRNA molecule; (d) a ribozyme; (e) a triplex molecule; (f) wild-type AKAP9 nucleic acid; (g) wild-type AKAP9 protein; (h) a protein which binds wild-type or altered AKAP9 protein; (i) a peptidomimetic; (j) a non-peptide, non-nucleic acid small molecule; and (k) an antibody.

In a thirteenth aspect, the invention provides a non-human animal which carries an altered AKAP9 allele in its genome. According to one embodiment of this aspect of the invention, a cell line isolated from the non-human animal is provided.

In a fourteenth aspect, the invention provides a method of screening for drug candidates useful in treating depression resulting from an alteration in AKAP9. The method, according to one embodiment, involves mixing a mutant AKAP9 in both the presence of a drug and the absence of the drug and measuring the level of the biological activity of the mutant AKAP9. If the level of the biological activity is different in the presence of the drug than in the absence of the drug, then it is a drug candidate for treating depression. According to another embodiment of this aspect of the invention, the method involves treating an animal, which is heterozygous or homozygous for AKAP9 containing an alteration, with a drug. If the animal does not develop depression, or symptoms thereof, then the drug is a candidate for treating depression. In yet another embodiment of this aspect of the invention, a method for screening potential depression therapeutics is provided. The method according to this embodiment involves combining an AKAP9 binding partner and a compound suspected of being a depression therapeutic and measuring the biological activity of the binding partner.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The invention relates to the discovery of an AKAP9 variant that is associated with depression. DNA sequencing of the AKAP9 gene in a population with and without major depression revealed that a SNP in the AKAP9 gene is associated with major depression. This SNP causes a missense mutation, changing a lysine residue to an arginine residue. The association of an altered AKAP9 with depression provides for new methods of detecting predisposition to depression and allows for the development of therapeutics that modify AKAP9 mediate signaling for treating depression.

AKAP9 (also known as yotiao, hyperion, CG-NAP, centrosome and golgi-localized PKN-associated protein, AKAP350A, AKAP450, AKAP120, KIAA0803) is known to be involved in a number of protein-protein interactions. AKAPs are known to interact with Protein Kinase A (PKA; cAMP-dependent protein kinase) through binding to a PKA regulatory subunit. The PKA holoenzyme consists of two catalytic subunits and a regulatory subunit dimer. Phosphorylation of PKA substrate is catalyzed by the catalytic subunit, while sub-cellular localization depends on protein-protein interactions between the regulatory dimer and AKAPs. There are four PKA regulatory subunit isoforms (RIα, RIβ, RIIα, and RIIβ). Each regulatory subunit has a similar overall structure but differs in responsiveness to cAMP and sub-cellular localization. An important function of AKAPs is to coordinate cAMP-mediated signaling by binding and localizing PKA via its regulatory subunits.

Cyclic AMP-dependent kinase signaling abnormalities have been associated with depression and symptoms of depression. Shelton et al. *Int. J. Neuropsychopharmacol.* 3:187-192 (1999) reported that reduced PKA in fibroblasts was associated with melancholic major depression. Dwivedi et al. *Biol. Psychiatry* 56(1):30-40 (2004) reported that PKA levels were altered in the brains of learned helpless rats. Perera et al. *CNS Spectrums* 6(7):565-572 (2001) discusses the potential roles of PKA in depression and antidepressants. Thus, AKAP9 mediated signaling may be involved in the etiology of depression by modulating PKA signaling.

One splice variant of AKAP9 has 3,908 amino acids, and there are at least five other different AKAP9 isoforms produced by alternative splicing. An alternative splice variant of AKAP9 consisting of 1,642 residues is found at neuronal and neuromuscular synapses. It specifically interacts with the N-methyl-D-aspartate (NMDA) receptor (NR1) in brain, and may function to attach NR1 to the postsynaptic cytoskeleton. It also binds to PKA and to type I protein phosphatase (PP1), leading to the conclusion that it is an AKAP that functions to bring together NR1 and its regulatory enzymes, thus regulating NR1 channel activity (Lin et al. *J. Neuroscience* 18:2012-2027 (1998)). Changes in expression levels of NMDA receptor subunits and associated intracellular proteins have been observed in patients with schizophrenia, bipolar disorder and major depression (see, e.g., Nudmanmud-Thanoi et al. *Neurosci. Lett.* 30:173-7 (2004); Clinton et al. *Neuropsychopharmacology* 29(7):1353-62 (2004); and Heresco-Levy et al. *Eur. Neuropsychopharmacol.* 8(2):141-52 (1998)).

Disruption of the association between PKA/PP1 and AKAP9 attenuates dopamine D4 modulation of $GABA_A$ currents, suggesting that targeting of PKA/PP1 to the vicinity of $GABA_A$ receptors by AKAP9 is required for dopaminergic signaling. The dopamine D4 receptor is a principal target of antipsychotic drugs, and disorders in dopaminergic signaling are thought to be involved in several psychiatric disorders including schizophrenia and depression. Thus, the inventors have identified an AKAP9 variant associated with depression and/or a predisposition to depression. This association links AKAP9 to PKA mediated signaling.

Recently, an amino acid variant was discovered in AKAP2 (A kinase-anchoring protein 2). The mutation was an isoleucine to valine substitution in the A-kinase binding domain. The mutation caused a three-fold change in binding affinity for PKA-RIα which resulted in altering the sub-cellular distribution of PKA-RIα. The authors hypothesized that this alteration imparted a negative health prognosis since this mutation was significantly correlated with age (Kammerer et al. *PNAS* 100(7):4066-71 (2003)). Thus, a conservative mutation in AKAP2 caused a changed in its ability to bind a PKA regulatory subunit.

Table 1 below shows the position of the SNP and the corresponding amino acid variant of AKAP9 (relative to several GenBank accession numbers representing different AKAP9 splice forms) that the inventors discovered was associated with depression.

TABLE 1

GenBank accession numbers and position of AKAP9 SNP

| GenBank Accession No. | Nucleotide Position | Amino Acid Position |
|---|---|---|
| NM_005751 | 7673 | K2484R |
| NM_147171 | 7709 | K2496R |
| NM_147185 | 7649 | K2476R |

The skilled artisan will readily recognize that the invention, in its various embodiments, encompasses these various AKAP9 splice variants and their use. Depending on the splicing, these splice variants may or may not have the AKAP9 variant as listed in Table 1.

The discovery that an AKAP9 variant plays a role in depression provides the means to detect depression or a predisposition to depression by determining if the individual has the AKAP9 variant disclosed herein. Since AKAP9 is now implicated in the etiology of depression, new therapeutics can be developed to target AKAP9 mediated signaling. Thus, the invention provides screens for modulators of AKAP9 mediated signaling.

Definitions

As used herein, the term "AKAP9" refers to human AKAP9 and splice variants of AKAP9 including, but not limited to those in GenBank accession number NM_005751, NM_147171, and NM_147185.

As used herein, the term "AKAP9 receptor" refers to a protein that is a receptor or ion channel that binds directly or indirectly to AKAP9. Examples of AKAP9 receptors include, but are not limited to, the type 1 inositol 1, 4, 5, triphosphates receptor ($InsP_3R1$) (Tu et al. *JBC* 279:19375-19382 (2004)); the NMDA receptor (Westphal et al. *Science* 285:93-96 (1999); and chloride intracellular channel 4(CLIC4) Berryman et al. *Cell Motil Cytoskeleton* 56(3):159-72 (2003).

As used herein, the term "AKAP9 binding partner" refers to a protein that binds AKAP9. Examples of AKAP9 binding partners include, but are not limited to, cAMP dependent protein kinase (PICA) via its regulatory subunit (PKA-R), protein kinase N (PKN) (Takahashi et al. *JBC* 274:17267-17274 (1999); protein phosphatase 1 (PP1) (Takahashi et al. *JBC* 274:17267-17274 (1999); protein phosphatase 2A (PP2A) via regulatory B subunit PR130 (Takahashi et al. *JBC* 274:17267-17274 (1999); transforming acidic coil-coiled protein 4 (TACC4)(Steadman et al. *JBC* 277:30165-30176 (2002); cdc42 Interacting Protein 4 (CIP4)(Larocca et al. *Mol. Biol. Cell* 15(6): 2771-2781 (2004); (PDE4D3) Tasken et al. *J. Biol. Chem.* 276:21999-22002, June 22, (2001); protein kinase C epsilon (PKC epsilon) cAMP phosphodiesterase 4D (PDE4D3)(Takahashi et al. *JBC* 275:34592-34596 (1999);).

As used herein, the terms "polypeptide;" "protein," and "peptide" interchangeably refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, prenylated forms, etc. Modifications also include intra-molecular cross-linking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the term "isolated" when used in reference to nucleic acids (which include gene sequences) of this invention is intended to mean that a nucleic acid molecule is present in a form other than that found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome, but not one or more other portions present on the same chromosome. Thus, for example, an isolated gene typically includes no more than 5 kb, preferably no more than 2.5 kb, more preferably no more than 1 kb naturally occurring nucleic acid sequence that immediately flanks the gene in the naturally existing chromosome or genomic DNA. However, it is noted that an "isolated nucleic acid" as used herein is distinct from a clone in a conventional library such as a genomic DNA library or a cDNA library in that the clones in a library are still in admixture with almost all the other nucleic acids in a chromosome or a cell. An isolated nucleic acid can be in a vector. An isolated nucleic acid can also be part of a composition so long as the composition is substantially different from the nucleic acid's original natural environment. In this respect, an isolated nucleic acid can be in a semi-purified state, i.e., in a composition having certain natural cellular components, while it is substantially separated from other naturally occurring nucleic acids and can be readily detected and/or assayed by standard molecular biology techniques. Preferably, an "isolated nucleic acid" is separated from at least 50%, more preferably at least 75%, most preferably at least 90% of other naturally occurring nucleic acids.

The term "isolated nucleic acid" encompasses the term "purified nucleic acid," which means a specified nucleic acid is in a substantially homogenous preparation of nucleic acid substantially free of other cellular components, other nucleic acids, viral materials, or culture medium, or chemical precursors or by-products associated with chemical reactions for chemical synthesis of nucleic acids. Typically, a "purified nucleic acid" can be obtained by standard nucleic acid purification methods. In a purified nucleic acid, preferably the specified nucleic acid molecule constitutes at least 75%, preferably at least 85%, and more preferably at least 95% of the total nucleic acids in the preparation. The term "purified nucleic acid" also means nucleic acids prepared from a recombinant host cell (in which the nucleic acids have been recombinantly amplified and/or expressed) or chemically synthesized nucleic acids.

The term "isolated nucleic acid" also encompasses "recombinant nucleic acid" which is used herein to mean a hybrid nucleic acid produced by recombinant DNA technology having the specified nucleic acid molecule covalently linked to one or more nucleic acid molecules that are not the nucleic acids naturally flanking the specified nucleic acid. Typically, such one or more nucleic acid molecules flanking the specified nucleic acid are no more than 50 kb, preferably no more than 25 kb.

As used herein, the term "isolated polypeptide" refers to a polypeptide molecule is present in a form other than found in nature in its original environment with respect to its association with other molecules. Typically, an "isolated polypeptide" is separated from at least 50%, more preferably at least 75%, most preferably at least 90% of other naturally co-existing polypeptides in a cell, tissue or organism.

The term "isolated polypeptide" encompasses a "purified polypeptide," which is used herein to mean a specified polypeptide that is in a substantially homogenous preparation substantially free of other cellular components, other polypeptides, viral materials, or culture medium, or when the polypeptide is chemically synthesized, chemical precursors or by-products associated with the chemical synthesis. For a purified polypeptide, preferably the specified polypeptide molecule constitutes at least 75%, preferably at least 85%, and more preferably at least 95% of the total polypeptide in the preparation. A "purified polypeptide" can be obtained from natural or recombinant host cells by standard purification techniques, or by chemically synthesis.

As used herein, the term "isolated polypeptide" also encompasses a "recombinant polypeptide" which is used herein to mean a hybrid polypeptide produced by recombinant DNA technology or chemical synthesis having a specified polypeptide molecule covalently linked to one or more polypeptide molecules that do not naturally flank the specified polypeptide.

As used herein, the term "homologue," when used in connection with a first native protein or fragment thereof that is discovered, according to the present invention, to interact with a second native protein or fragment thereof, means a polypeptide that exhibits an amino acid sequence homology and/or structural resemblance to the first native interacting protein, or to one of the interacting domains of the first native protein such that it is capable of interacting with the second native protein. Typically, a protein homologue of a native protein may have an amino acid sequence that is at least 50%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein. Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein-protein interactions, e.g., the yeast two-hybrid system described below, as will be apparent to skilled artisans apprised of the present invention. Other techniques for detecting protein-protein interactions include, e.g., protein affinity chromatography, affinity blotting, in vitro binding assays, and the like.

For the purpose of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, Bull. Math. Biol., 51:5-37 (1989) and Myers and Miller, Comput. Appl. Biosci., 4(1):11-17 (1988). Specifically, the identity is determined by the ALIGN program, which is available at http://www2.igh.cnrs.fr maintained by IGH, Montpellier, FRANCE. The default parameters are used. Where the length of the test sequence is at least 90% of the length of the reference sequence, the percentage identity is determined by the algorithm of Karlin and Altschul, Proc. Natl. Acad. Sci. USA, 90:5873-5877 (1993), which is incorporated into various BLAST programs. Specifically, the percentage identity is determined by the "BLAST 2 Sequences" tool, which is available at http://www.ncbi.nlm.nih.gov/gorf/bl2.html. See Tatusova and Madden, FEMS Microbiol. Lett., 174(2):247-250 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

As used herein, the term "derivative," when used in connection with a first native protein (or fragment thereof) that is discovered, according to the present invention, to interact with a second native protein (or fragment thereof), means a modified form of the first native protein prepared by modifying the side chain groups of the first native protein without changing the amino acid sequence of the first native protein. The modified form, i.e., the derivative should be capable of interacting with the second native protein. Examples of modified forms include glycosylated forms, phosphorylated forms, myristylated forms, ribosylated forms, ubiquitinated forms, prenylated forms, and the like. Derivatives also include hybrid or fusion proteins containing a native protein or a fragment thereof. Methods for preparing such derivative forms should be apparent to skilled artisans. The prepared derivatives can be easily tested for their ability to interact with the native interacting partner using techniques known in the art, e.g., protein affinity chromatography, affinity blotting, in vitro binding assays, yeast two-hybrid assays, and the like.

As used herein, the term "isolated protein complex" refers a protein complex present in a composition or environment that is different from that found in nature—in its native or original cellular or biological environment. Preferably, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex," that is, a substantially purified form in a substantially homogenous preparation substantially free of other cellular components, other polypeptides, viral materials, or culture medium, or, when the protein components in the protein complex are chemically synthesized, free of chemical precursors or by-products associated with the chemical synthesis. A "purified protein complex" typically means a preparation containing preferably at least 75%, more preferably at least 85%, and most preferably at least 95% a particular protein complex. A "purified protein complex" may be obtained from natural or recombinant host cells or other body samples by standard purification techniques, or by chemical synthesis.

As used herein, the terms "hybrid protein," "hybrid polypeptide," "hybrid peptide," "fusion protein," "fusion polypeptide," and "fusion peptide" interchangeably refer to a non-naturally occurring protein having a specified polypeptide molecule covalently linked to one or more polypeptide molecules that do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

As used herein, the term "interacting" or "interaction" means that two protein domains, fragments or complete proteins exhibit sufficient physical affinity to each other so as to bring the two "interacting" protein domains, fragments or proteins physically close to each other. An extreme case of interaction is the formation of a chemical bond that results in continual and stable proximity of the two entities. Interactions, that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interaction domains, fragments, proteins or entities may be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like. An "interaction" between two protein domains, fragments or complete proteins can be determined by a number of methods. For example, an interaction can be determined by functional assays such as the two-hybrid systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, Microbiol. Rev., 59:94-123 (1995).

As used herein, the term "protein complex" means a composite unit that is a combination of two or more proteins formed by interaction between the proteins. Typically, but not necessarily, a "protein complex" is formed by the binding of two or more proteins together through specific non-covalent binding interactions. However, covalent bonds may also be present between the interacting partners. For instance, the two interacting partners can be covalently cross-linked so that the protein complex becomes more stable.

The term "protein fragment" as used herein means a polypeptide that represents a portion of a protein. When a protein fragment exhibits interactions with another protein or protein fragment, the two entities are said to interact through interaction domains that are contained within the entities.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

As used herein, the term "antibody" refers to both monoclonal and polyclonal antibodies that fall within any antibody classes, e.g., IgG, IgM, IgA, IgE or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

As used herein, the term "selectively immunoreactive" refers to an antibody that binds to a specific protein or protein complex, but not other similar proteins or fragments or components thereof.

As used herein, the term "activity" when used in connection with proteins or protein complexes refers to any physiological or biochemical activities displayed by or associated with a particular protein or protein complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of protein complexes, the ability to maintain the form of a protein complex), antigenicity and immunogenecity, enzymatic activities, etc. Such activities may be detected or assayed by any of a variety of suitable methods as will be apparent to skilled artisans.

As used herein, the term "compound" refers to all types of organic or inorganic molecules, including but not limited to proteins, peptides, polysaccharides, lipids, nucleic acids, small organic molecules, inorganic compounds, and derivatives thereof.

As used herein, the term "interaction antagonist" refers a compound that interferes with, blocks, disrupts or destabilizes a protein-protein interaction; blocks or interferes with the formation of a protein complex; or destabilizes, disrupts or dissociates an existing protein complex.

As used herein, the term "interaction agonist" refers to a compound that triggers, initiates, propagates, nucleates, or otherwise enhances the formation of a protein-protein interaction; triggers, initiates, propagates, nucleates, or otherwise enhances the formation of a protein complex; or stabilizes an existing protein complex.

AKAP9 Nucleic Acids

Accordingly, the present invention provides an isolated AKAP9 nucleic acid containing the newly discovered nucleotide variant, or one or more nucleotide variants that will result in the resultant amino acid variant. The term "AKAP9 nucleic acid" is as defined above and means a naturally existing nucleic acid coding for a wild-type or variant or mutant AKAP9. The term "AKAP9 nucleic acid" is inclusive and may be in the form of either double-stranded or single-stranded nucleic acids, and a single strand can be either of the two complementing strands. The isolated AKAP9 nucleic acid can be naturally existing genomic DNA, mRNA or cDNA. In one embodiment, the isolated AKAP9 nucleic acid has a nucleotide sequence according to SEQ ID NO:1 or the complement thereof.

In another embodiment, the isolated AKAP9 nucleic acid has a nucleotide sequence that is at least 95%, preferably at least 97% and more preferably at least 99% identical to SEQ ID NO:1 and contains the discovered nucleotide variant, or one or more nucleotide variants that will result in the discovered amino acid variant, or the complement thereof.

In yet another embodiment, the isolated AKAP9 nucleic acid has a nucleotide sequence encoding AKAP9 protein having an amino acid sequence according to SEQ ID NO:2 and contains the discovered amino acid varians of Table 1. Isolated AKAP9 nucleic acids having a nucleotide sequence that is the complement of the sequence are also encompassed by the present invention.

In yet another embodiment, the isolated AKAP9 nucleic acid has a nucleotide sequence encoding a AKAP9 protein having an amino acid sequence that is at least 95%, preferably at least 97% and more preferably at least 99% identical to SEQ ID NO:2 and contains the discovered amino acid variant, or the complement thereof.

The present invention also provides an isolated nucleic acid, naturally occurring or artificial, having a nucleotide sequence that is at least 95%, preferably at least 97% and more preferably at least 99% identical to SEQ ID NO:1 and contains the discovered nucleotide variant, or the complement thereof.

In another embodiment, the present invention provides an isolated nucleic acid, naturally occurring or artificial, having a nucleotide sequence encoding an AKAP9 protein having an amino acid sequence according to SEQ ID NO:2 and containing the discovered amino acid variant of Table 1. Isolated nucleic acids having a nucleotide sequence that is the complement of the sequence are also encompassed by the present invention.

In addition, isolated nucleic acids are also provided which have a nucleotide sequence encoding a protein having an amino acid sequence that is at least 95%, preferably at least 97% and more preferably at least 99% identical to SEQ ID NO:2 and contains the discovered amino acid variant of Table 1, or the complement thereof.

Also encompassed are isolated AKAP9 nucleic acids obtainable by:

(a) providing a human genomic library;

(b) screening the genomic library using a probe having a nucleotide sequence according to any one of SEQ ID NO:1; and (c) producing a genomic DNA comprising a contiguous span of at least 30 nucleotides of any one of SEQ ID NO:1, wherein the genomic DNA thus produced contains the discovered nucleotide variants.

The present invention also includes isolated AKAP9 nucleic acids obtainable by:

(i) providing a cDNA library using human mRNA from a human tissue, e.g., blood;

(ii) screening the cDNA library using a probe having a nucleotide sequence according to any one of SEQ ID NO:1; and (iii) producing a cDNA DNA comprising a contiguous span of at least 30 nucleotides of any one of SEQ ID NO:1, wherein the cDNA thus produced contains the discovered nucleotide variant.

The present invention also encompasses an isolated nucleic acid comprising the nucleotide sequence of a region of a AKAP9 genomic DNA or cDNA or mRNA, wherein the region contains the discovered nucleotide variant or one or more nucleotide variants that will give rise to the discovered amino acid variant, or the complement thereof. Such regions can be isolated and analyzed to efficiently detect the nucleotide variants of the present invention. Also, such regions can also be isolated and used as probes or primers in detection of the nucleotide variants of the present invention and other uses as will be clear from the descriptions below.

Thus, in one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of a AKAP9 nucleic acid, the contiguous span containing the discovered nucleotide variant, or the complement thereof. In specific embodiments, the isolated nucleic acids are oligonucleotides having a contiguous span of from about 17, 18, 19, 20, 21, 22, 23 or 25 to about 30, 40 or 50, preferably from about 21 to about 30 nucleotide residues, of any AKAP9 nucleic acid, said contiguous span containing the discovered nucleotide variant.

In one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of any one of SEQ ID NO:1, containing the discovered nucleotide variant, or the complement thereof. In specific embodiments, the isolated nucleic acid comprises a nucleotide sequence according to any one of SEQ ID NO:1. In preferred embodiments, the isolated nucleic acids are oligonucleotides having a contiguous span of from about 17, 18, 19, 20, 21, 22, 23 or 25 to about 30, 40 or 50, preferably from about 21 to about 30 nucleotide residues, of SEQ ID NO:1 and containing the discovered nucleotide variant. The complements of the isolated nucleic acids are also encompassed by the present invention.

In preferred embodiments, an isolated oligonucleotide of the present invention is specific to an AKAP9 allele ("allele-specific") Containing the nucleotide variants as disclosed in the present invention. That is, the isolated oligonucleotide is capable of selectively hybridizing, under high stringency conditions generally recognized in the art, to a AKAP9 genomic or cDNA or mRNA containing one or more nucleotide variants as disclosed in the present invention, but not to an AKAP9 gene not having the variant. Such oligonucleotides will be useful in a hybridization-based method for detecting the nucleotide variants of the present invention as described in details below. An ordinarily skilled artisan would recognize various stringent conditions which enable the oligonucleotides of the present invention to differentiate between a AKAP9 gene having a reference sequence and a variant AKAP9 gene of the present invention. For example, the hybridization can be conducted overnight in a solution containing 50% formamide, 5×SSC, pH7.6, 5×Denhardt's solution, 10% dextran sulfate, and 20 microgram/ml denatured, sheared salmon sperm DNA. The hybridization filters can be washed in 0.1×SSC at about 65° C. Alternatively, typical PCR conditions employed in the art with an annealing temperature of about 55° C. can also be used.

In the isolated AKAP9 oligonucleotides containing a nucleotide variant according to the present invention, the nucleotide variant can be located in any position. In one embodiment, a nucleotide variant is at the 5' or 3' end of the oligonucleotides. In a more preferred embodiment, a AKAP9 oligonucleotide contains only one nucleotide variant according to the present invention, which is located at the 3' end of the oligonucleotide. In another embodiment, a nucleotide variant of the present invention is located within no greater than four (4), preferably no greater than three (3), and more preferably no greater than two (2) nucleotides of the center of the oligonucleotide of the present invention. In more preferred embodiment, a nucleotide variant is located at the center or within one (1) nucleotide of the center of the oligonucleotide. For purposes of defining the location of a nucleotide variant in an oligonucleotide, the center nucleotide of an oligonucleotide with an odd number of nucleotides is considered to be the center. For an oligonucleotide with an even number of nucleotides, the bond between the two center nucleotides is considered to be the center.

In other embodiments of the present invention, isolated nucleic acids are provided which encode a contiguous span of at least 6, 7, 8, 9, 10, 11, 12, 13, 14, 15, 16 or 17 amino acids of a AKAP9 protein wherein said contiguous span contains the discovered amino acid variant according to the present invention.

The oligonucleotides of the present invention can have a detectable marker selected from, e.g., radioisotopes, fluorescent compounds, enzymes, or enzyme co-factors operably linked to the oligonucleotide. The oligonucleotides of the present invention can be useful in genotyping as will be apparent from the description below.

In addition, the present invention also provides DNA microchips or microarray incorporating a variant AKAP9 genomic DNA or cDNA or mRNA or an oligonucleotide according to the present invention. The microchip will allow rapid genotyping and/or haplotyping in a large scale.

As is known in the art, in microchips, a large number of different nucleic acid probes are attached or immobilized in an array on a solid support, e.g., a silicon chip or glass slide. Target nucleic acid sequences to be analyzed can be contacted with the immobilized oligonucleotide probes on the microchip. See Lipshutz et al., *Biotechniques*, 19:442-447 (1995); Chee et al., *Science*, 274:610-614 (1996); Kozal et al., *Nat. Med.* 2:753-759 (1996); Hacia et al., *Nat. Genet.*, 14:441-447 (1996); Saiki et al., *Proc. Natl. Acad. Sci. USA*, 86:6230-6234 (1989); Gingeras et al., *Genome Res.*, 8:435-448 (1998). The microchip technologies combined with computerized analysis tools allow large-scale high throughput screening. See, e.g., U.S. Pat. No. 5,925,525 to Fodor et al; Wilgenbus et al., *J. Mol. Med.*, 77:761-786 (1999); Graber et al., *Curr. Opin. Biotechnol.*, 9:14-18 (1998); Hacia et al., *Nat. Genet.*, 14:441-447 (1996); Shoemaker et al., *Nat. Genet.*, 14:450-456 (1996); DeRisi et al., *Nat. Genet.*, 14:457-460 (1996); Chee et al., *Nat. Genet.*, 14:610-614 (1996); Lockhart et al., *Nat. Genet.*, 14:675-680 (1996); Drobyshev et al., *Gene*, 188:45-52 (1997).

AKAP9 Protein and Peptide

The present invention also provides isolated proteins encoded by one of the isolated nucleic acids according to the present invention. In one aspect, the present invention provides an isolated AKAP9 protein'encoded by one of the novel AKAP9 gene variants according to the present invention. Thus, for example, the present invention provides an isolated AKAP9 protein having an amino acid sequence according to SEQ ID NO:2 and contains the discovered amino acid variant.

In another example, the isolated AKAP9 protein of the present invention has an amino acid sequence at least 95%, preferably 97%, more preferably 99% identical to SEQ ID NO:2 wherein the amino acid sequence contains the discovered amino acid variant.

In addition, the present invention also encompasses isolated peptides having a contiguous span of at least 6, 7, 8, 9, 10, 11, 12, 13, 15, 17, 19 or 21 or more amino acids of an isolated AKAP9 protein of the present invention said contiguous span encompassing the discovered amino acid variant. In preferred embodiments, the isolated variant AKAP9 peptides contain no greater than 200 or 100 amino acids, and preferably no greater than 50 amino acids. In specific embodiments, the AKAP9 polypeptides, in accordance with the present invention, contains the discovered amino acid variant identified in accordance with the present invention. The peptides can be useful in preparing antibodies specific to the mutant AKAP9 proteins provided in accordance with the present invention.

As will be apparent to an ordinarily skilled artisan, the isolated nucleic acids and isolated polypeptides of the present invention can be prepared using techniques generally known in the field of molecular biology. See generally, Sambrook et al., *Molecular Cloning: A Laboratory Manual*, 2$^{nd}$ ed., Cold Spring Harbor Laboratory, Cold Spring Harbor, N.Y., 1989. The isolated AKAP9 gene or cDNA or oligonucleotides of this invention can be operably linked to one or more other DNA fragments. For example, the isolated AKAP9 nucleic acid (e.g., cDNA or oligonucleotides) can be ligated to another DNA such that a fusion protein can be encoded by the ligation product. The isolated AKAP9 nucleic acid (e.g., cDNA or oligonucleotides) can also be incorporated into a DNA vector for purposes of, e.g., amplifying the nucleic acid or a portion thereof, and/or expressing a mutant AKAP9 polypeptide or a fusion protein thereof.

Thus, the present invention also provides a vector construct containing an isolated nucleic acid of the present invention, such as a mutant AKAP9 nucleic acid (e.g., cDNA or oligonucleotides) of the present invention. Generally, the vector construct may include a promoter operably linked to a DNA of interest (including a full-length sequence or a fragment thereof in the 5' to 3' direction or in the reverse direction for purposes of producing antisense nucleic acids), an origin of DNA replication for the replication of the vector in host cells and a replication origin for the amplification of the vector in, e.g., *E. coli*, and selection marker(s) for selecting and maintaining only those host cells harboring the vector. Additionally, the vector preferably also contains inducible elements, which function to control the expression of the isolated gene sequence. Other regulatory sequences such as transcriptional termination sequences and translation regulation sequences (e.g., Shine-Dalgarno sequence) can also be included. An epitope tag-coding sequence for detection and/or purification of the encoded polypeptide can also be incorporated into the vector construct. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vector construct can be introduced into the host cells or organisms by any techniques known in the art, e.g., by direct DNA transformation, microinjection, electroporation, viral infection, lipofection, gene gun, and the like. The vector construct can be maintained in host cells in an extrachromosomal state, i.e., as self-replicating plasmids or viruses. Alternatively, the vector construct can be integrated into chromosomes of the host cells by conventional techniques such as selection of stable cell lines or site-specific recombination. The vector construct can be designed to be suitable for expression in various host cells, including but not limited to bacteria, yeast cells, plant cells, insect cells, and mammalian and human cells. A skilled artisan will recognize that the designs of the vectors can vary with the host cell used.

Diagnostics

The discovery by the present inventors that an AKAP9 mutation segregates with depression now allows for depression susceptibility testing based on detecting mutations in AKAP9.

Thus, the present invention also provides a method for genotyping the AKAP9 gene by determining whether an individual has a nucleotide variant or amino acid variant of the present invention.

Similarly, a method for haplotyping the AKAP9 gene is also provided. Haplotyping can be done by any methods known in the art. For example, only one copy of the AKAP9 gene can be isolated from an individual and the nucleotide at each of the variant positions is determined. Alternatively, an allele specific PCR or a similar method can be used to amplify only one copy of the AKAP9 gene in an individual, and the SNPs at the variant positions of the present invention are determined. The Clark method known in the art can also be employed for haplotyping. A high throughput molecular haplotyping method is also disclosed in Tost et al., *Nucleic Acids Res.*, 30(19):e96 (2002), which is incorporated herein by reference.

Thus, additional variant(s) that are in linkage disequilibrium with the variants and/or haplotypes of the present invention can be identified by a haplotyping method known in the art, as will be apparent to a skilled artisan in the field of genetics and haplotying. The additional variants that are in linkage disequilibrium with a variant or haplotype of the present invention can also be useful in the various applications as described below.

In one aspect, the invention features probes and primers for use in a prognostic or diagnostic assay. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or antisense sequence of AKAP9, including 5' and/or 3' untranslated regions. In preferred embodiments, the probe further comprises a detectable label group attached thereto, e.g. the label group is selected from amongst radioisotopes, fluorescent compounds, enzymes, and enzyme cofactors. The selection of probes and primers for diagnosis of a susceptibility of depression (i.e, detection of AKAP9 mutations) is within the capability of the skilled artisan apprised of the invention.

In a further aspect, the present invention features methods for determining whether a subject is at risk for developing depression. According to the diagnostic and prognostic methods of the present invention, alteration of the wild-type AKAP9 locus is detected. "Alteration of a wild-type gene" encompasses all forms of mutations including deletions, insertions and point mutations in the coding and non-coding regions. Deletions may be of the entire gene or of only a portion of the gene. Point mutations may result in stop codons, frameshift mutations or amino acid substitutions. Point mutations or deletions in the promoter can change transcription and thereby alter the gene function. Somatic mutations are those which occur only in certain tissues and are not inherited in the germline. Germline mutations can be found in any of a body's tissues and are inherited. The finding of AKAP9 germline mutations thus provides diagnostic information. An AKAP9 allele which is not deleted (e.g., found on the sister chromosome to a chromosome carrying an AKAP9 deletion) can be screened for other mutations, such as insertions, small deletions, and point mutations. Point mutational events may occur in regulatory regions, such as in the promoter of the gene, or in intron regions or at intron/exon junctions. In a preferred embodiment, the mutation is at nucleotide 7673 where the A is substituted with a G resulting in an AKAP9 protein having lysine 2484 substituted with arginine (referenced to SEQ ID NO:1).

Useful diagnostic techniques include, but are not limited to fluorescent in situ hybridization (FISH), direct DNA sequencing, PFGE (pulsed-field gel electrophoresis) analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology. In addition to the techniques described herein, similar and other useful techniques are also described in U.S. Pat. Nos. 5,837,492 and 5,800,998, each incorporated herein by reference.

Predisposition to disease can be ascertained by testing any tissue of a human for mutations of the AKAP9 gene. For example, a person who has inherited a germline AKAP9 mutation may be prone to developing depression. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the AKAP9 gene. Alteration of a wild-type AKAP9 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCA) (Orita, et al. *Proc. Natl. Acad. Sci. USA* 86:2776-2770 (1989)). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield, V. C., et al. *Am. J. Hum. Genet.* 49:699-706 (1991)), heteroduplex analysis (HA) (White, M. B., et al., *Genomics* 12:301-306 (1992)) and chemical mismatch cleavage (CMC) (Grompe, M., et al., *Proc. Natl. Acad. Sci. USA* 86:5855-5892 (1989)). None of the methods described above will detect large deletions, duplications or insertions, nor will they detect a regulatory mutation which affects transcription or translation of the protein. Other methods which can detect these classes of mutations such as a protein truncation assay or the asymmetric assay, detect only specific types of mutations and would not detect missense mutations. A review of currently available methods of detecting DNA sequence variation can be found in a recent review by Grompe, M., *Nature Genetics* 5:111-117 (1993). Once a mutation is known, an allele specific detection approach such as allele specific oligonucleotide (ASO) hybridization can be utilized to rapidly screen large numbers of other samples for that same mutation.

Detection of point mutations may be accomplished by molecular cloning of the AKAP9 allele(s) and sequencing the allele(s) using techniques well known in the art. Alternatively, the gene sequences can be amplified directly from a genomic DNA preparation from the tissue or cells, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita, et al. *Proc. Natl. Acad. Sci. USA* 86:2776-2770 (1989)); 2) denaturing gradient gel electrophoresis (DGGE) (Wartell, R. M., et al. *Nucl. Acids Res.* 18:2699-2705 (1990); Sheffield, V. C., et al. *Proc. Natl. Acad. Sci. USA* 86:232-236 (1989)); 3) RNase protection assays (Finkelstein, J., et al. *Genomics* 7:167-172 (1990); Kinszler, K. W., et al. *Science* 251:1366-1370 (1991)); 4) allele-specific oligonucleotides (ASOs) (Conner, B. J., et al. *Proc. Natl. Acad. Sci. USA* 80:278-282 (1983)); 5) the use of proteins which recognize nucleotide mismatches, such as the *E. coli* mutS protein (Modrich, P. *Ann. Rev. Genet.* 25:229-253 (1991)); and 6) allele-specific PCR (Rano & Kidd *Nucl. Acids Res.* 17:8392 (1989)). For allele-specific PCR, primers are used which hybridize at their 3' ends to a particular AKAP9 mutation. If the particular AKAP9 mutation is not present, an amplification product is not observed. Amplification Refractory Mutation System (ARMS) can also be used, as disclosed in European Patent Application Publication No. 0332435 and in Newton, C. R., et al. Nucl. Acids Res. 17:2503-2516 (1989). Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the AKAP9 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type AKAP9 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the AKAP9 mRNA or gene but can be a segment of either. If the riboprobe comprises only a segment of the AKAP9 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton, et al. *Proc. Natl. Acad. Sci. USA* 85:4397-4401 (1988); Shenk, et al. *Proc. Natl. Acad. Sci. USA* 72:989 (1975); and Novack, et al. *Proc. Natl. Acad. Sci.* USA 83:586 (1986). Alternatively, mismatches can be detected by shifts in the electrophoretic mobility of mismatched duplexes relative to matched duplexes. See, e.g., Cariello *Human Genetics* 42:726 (1988). With either riboprobes or DNA probes, the cellular mRNA or DNA which might contain a mutation can be amplified using PCR before hybridization. Changes in DNA of the AKAP9 gene can also be detected using Southern hybridization, especially if the changes are gross rearrangements, such as deletions and insertions.

DNA sequences of the AKAP9 gene which have been amplified by use of PCR may also be screened using allele-specific probes. These probes are nucleic acid oligomers, each of which contains a region of the AKAP9 gene sequence harboring a known mutation. For example, one oligomer may be about 30 nucleotides in length (although shorter and longer oligomers are also usable as well recognized by those of skill in the art), corresponding to a portion of the AKAP9 gene sequence. By use of a battery of such allele-specific probes, PCR amplification products can be screened to identify the presence of a previously identified mutation in the AKAP9 gene. Hybridization of allele-specific probes with amplified AKAP9 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, and/or one can measure expression levels of a gene of interest. The method is one of parallel processing of many, even thousands, of probes at once and can tremendously increase the rate of analysis. Several papers have been published which use this technique. See, e.g., Hacia J G, et al. *Nature Genetics* 14:441-447 (1996); Shoemaker D D, et al. *Nature Genetics* 14:450-456 (1996); Chee, M., et al. *Science* 274:610-614 (1996); Lockhart D J, et al. *Nature Biotechnology* 14:1675-1680 (1996); DeRisi, J., et al. *Nat. Genet.* 14:457-460 (1996); Lipshutz R J, et al. *BioTechniques* 19:442-447 (1995). This method has already been used to screen people for mutations in the breast cancer gene BRCA1 (Hacia, J G, et al. *Nature Genetics* 14:441-447 (1996)). This new technology has been reviewed in a news article in Chemical and Engineering News (Borman, S. Chemical & Engineering News, December 9 issue, pp. 42-43 (1996)) and been the subject of an editorial (*Nature Genetics*, 1996). Also see Fodor, S.P.A. *Science* 277:393-395 (1997).

The most definitive test for mutations in a candidate locus is to directly compare genomic AKAP9 sequences from disease patients with those from a control population. Alternatively, one could sequence messenger RNA after amplification, e.g., by PCR, thereby eliminating the necessity of determining the exon structure of the candidate gene.

Mutations from disease patients falling outside the coding region of AKAP9 can be detected by examining the non-coding regions, such as introns and regulatory sequences near or within the AKAP9 gene. An early indication that mutations in non-coding regions are important can come from Northern blot experiments that reveal messenger RNA molecules of abnormal size or abundance in disease patients as compared to control individuals.

Alteration of AKAP9 mRNA expression can be detected by any techniques known in the art. These include Northern blot analysis, PCR amplification and RNase protection. Diminished or increased mRNA expression indicates an alteration of the wild-type AKAP9 gene. Alteration of wild-type AKAP9 genes can also be detected by screening for alteration of wild-type AKAP9 protein. For example, monoclonal antibodies immunoreactive with AKAP9 can be used to screen a tissue. Lack of cognate antigen would indicate an AKAP9 mutation. Antibodies specific for products of mutant alleles could also be used to detect mutant AKAP9 gene product. Such immunological assays can be done in any convenient formats known in the art. These include Western blots, immunohistochemical assays and ELISA assays. Any means for detecting an altered AKAP9 protein can be used to detect alteration of wild-type AKAP9 genes. Functional assays, such as protein binding determinations, can be used. In addition, assays can be used which detect AKAP9 biochemical function. Finding a mutant AKAP9 gene product indicates alteration of a wild-type AKAP9 gene.

The primer pairs of the present invention are useful for determination of the nucleotide sequence of a particular AKAP9 allele using PCR. The pairs of single-stranded DNA primers can be annealed to sequences within or surrounding the AKAP9 gene on chromosome 12 in order to prime amplifying DNA synthesis of the AKAP9 gene itself. A complete set of these primers allows synthesis of all of the nucleotides of the AKAP9 gene coding sequences, i.e., the exons. The set of primers preferably allows synthesis of both intron and exon sequences. Allele-specific primers can also be used. Such primers anneal only to particular AKAP9 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from AKAP9 sequences or sequences adjacent to AKAP9, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the known sequences of the AKAP9 exons and the 5' alternate exon, the design of particular primers is well within the skill of the art. Suitable primers for mutation screening are also described herein.

The nucleic acid probes provided by the present invention are useful for a number of purposes. They can be used in Southern hybridization to genomic DNA and in the RNase protection method for detecting point mutations already discussed above. The probes can be used to detect PCR amplification products. They can also be used to detect mismatches with the AKAP9 gene or mRNA using other techniques.

It has been discovered that individuals with the wild-type AKAP9 gene do not have depression which results from the AKAP9 allele. However, mutations which interfere with the function of the AKAP9 protein are involved in the susceptibility to depression as shown herein. Thus, the presence of an altered (or a mutant) AKAP9 gene which produces a protein having a loss of function, or altered function, directly correlates to an increased risk of disease. In order to detect an AKAP9 gene mutation, a biological sample is prepared and analyzed for a difference between the sequence of the AKAP9 allele being analyzed and the sequence of the wild-type AKAP9 allele. Mutant AKAP9 alleles can be initially identified by any of the techniques described above. The mutant alleles are then sequenced to identify the specific mutation of the particular mutant allele. Alternatively, mutant AKAP9 alleles can be initially identified by identifying mutant (altered) AKAP9 proteins, using conventional techniques. The mutant alleles are then sequenced to identify the specific mutation for each allele. The mutations, especially those which lead to an altered function of the AKAP9 protein, are then used for the diagnostic methods of the present invention.

The present invention employs definitions commonly used in the art with specific reference to the gene described in the present application. Such definitions can be found in U.S. Pat. Nos. 5,837,492; 5,800,998; 6,261,801; 6,274,720 and 6,274,376, each incorporated herein by reference. Such definitions are employed herein unless the context indicates otherwise.

Methods of Use: Nucleic Acid Diagnosis and Diagnostic Kits

In order to detect the presence of an AKAP9 allele predisposing an individual to depression, a biological sample such as blood is prepared and analyzed for the presence or absence of predisposing alleles of AKAP9. Results of these tests and interpretive information are returned to the health care provider for communication to the tested individual. Such diagnoses can be performed by diagnostic laboratories, or, alternatively, diagnostic kits are manufactured and sold to health care providers or to private individuals for self-diagnosis. Diagnostic or prognostic tests can be performed as described herein or using well known techniques, such as described in U.S. Pat. No. 5,800,998, incorporated herein by reference.

Initially, the screening method can involve amplification of the relevant AKAP9 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with a polymerase. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for depression susceptibility), the biological sample to be analyzed, such as blood or serum, may be treated, if desired, to extract the nucleic acids. The sample nucleic acid can be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 12. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis T., et al. (1982) Molecular Cloning: A Laboratory Manual (Cold Spring Harbor Laboratory, Cold Spring Harbor, N.Y.) and Sambrook, J., et al. (1989) Molecular Cloning: A Laboratory Manual, 2nd Ed. (Cold Spring Harbor Laboratory, Cold Spring Harbor, N.Y.). Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka *Anal. Biochem.* 169:1 (1988); Landegren, et al. Science 242:229 (1988); Mittlin *Clinical Chem.* 35:1819 (1989); U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe can have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a 103-106 increase in sensitivity. For an example relating to the preparation of oligodeoxynucleotide-alkaline phosphatase conjugates and their use as hybridization probes see Jablonski, E., et al. *Nuc. Acids Res.* 14:6115-6128 (1986).

Two-step label amplification methodologies are known in the art. These assays work on the principle that a small ligand (such as digoxigenin, biotin, or the like) is attached to a nucleic acid probe capable of specifically binding AKAP9. Allele specific probes are also contemplated within the scope of this example and exemplary allele specific probes include probes encompassing the predisposing or potentially predisposing mutations summarized in herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby, P. W. J., et al. *J. Mol. Biol.* 113:237-251 (1977) and Nguyen, Q., et al. *BioTechniques* 13:116-123 (1992).

It is also contemplated within the scope of this invention that the nucleic acid probe assays of this invention will employ a cocktail of nucleic acid probes capable of detecting AKAP9. Thus, in one example to detect the presence of AKAP9 in a cell sample, more than one probe complementary to AKAP9 is employed and in particular the number of different probes is alternatively 2, 3, or 5 different nucleic acid probe sequences. In another example, to detect the presence of mutations in the AKAP9 gene sequence in a patient, more than one probe complementary to AKAP9 is employed where the cocktail includes probes capable of binding to the allele-specific mutations identified in populations of patients with alterations in AKAP9. In this embodiment, any number of probes can be used, and can preferably include probes corresponding to the major gene mutations identified as predisposing an individual to depression. Some candidate probes contemplated within the scope of the invention include probes that include the allele-specific mutations identified herein and those that have the AKAP9 regions corresponding to SEQ ID NO:1 both 5' and 3' to the mutation site.

Methods of Use: Peptide Diagnosis and Diagnostic Kits

Susceptibility to depression can also be detected on the basis of the alteration of wild-type AKAP9 polypeptide. Peptide diagnostic or prognostic tests can be performed as described herein or using well known techniques, such as described in U.S. Pat. No. 5,800,998, incorporated herein by reference. For example, such alterations can be determined by sequence analysis in accordance with conventional techniques. More preferably, antibodies (polyclonal or monoclonal) are used to detect differences in, or the absence of, AKAP9 peptides. The antibodies can be prepared in accordance with conventional techniques. Other techniques for raising and purifying antibodies are well known in the art and any such techniques may be chosen to achieve the preparations claimed in this invention. In a preferred embodiment of the invention, antibodies will immunoprecipitate AKAP9 proteins or fragments of the AKAP9 protein from solution as well as react with AKAP9 peptides on Western or immunoblots of polyacrylamide gels. In another preferred embodiment, antibodies will detect AKAP9 proteins and protein fragments in paraffin or frozen tissue sections, using immunocytochemical techniques.

Preferred embodiments relating to methods for detecting AKAP9 (or mutants thereof) include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference.

Methods of Use: Drug Screening

Polypeptides of the invention also may be used to assess the binding of small molecule substrates and ligands in, for example, cells, cell free preparations, chemical libraries, and natural product mixtures. These substrates and ligands may be natural substrates and ligands or may be structural or functional mimetics. See, e.g., Coligan et al., Current Protocols in Immunology 1(2):Chapter 5 (1991). Thus, the invention also provides a method of screening compounds to identify those which enhance (agonist) or block (antagonist) the action of AKAP9 polypeptides or polynucleotides, particularly those compounds for treating or preventing depression.

This invention is particularly useful for screening compounds by using a wild-type or mutant AKAP9 polypeptide or a binding fragment thereof in any of a variety of drug screening techniques. The individual components of the assays described herein are available commercially and/or can be produced by an ordinary skilled artisan. AKAP9 is described in U.S. Pat. No. 6,346,607 to Wang, issued Feb. 12, 2002, which is herein incorporated by reference in its entirety. The screens of the invention are intended to encompass the use of AKAP9 homologs and AKAP9 interacting proteins from any organism including, *C. elegans* and *Drosphila*, as well as human. The skilled artisan is capable of recognizing and employing AKAP9 homologs and homologs of AKAP9 interacting partners from other organisms in the assays of the invention. Drug screening can be performed as described herein or using well known techniques, such as described in U.S. Pat. Nos. 5,800,998 and 5,891,628, each incorporated herein by reference. Preferably test compounds that disrupt AKAP9 bioactivity are tested in a secondary assay such as an animal depression model, a cellular based apoptosis assay, and transgenic animal models being homozygous or heterozygous for an AKAP9 mutation that is associated with depression. Furthermore, as the skilled artisan readily understands, the screening assays described herein can be performed in a variety of configurations based on known AKAP9 biochemistry, including, but not limited to testing for modulation of AKAP9 mediated signaling, modulation of AKAP9 protein-protein interactions, modulation of PKA activity, modulation of cAMP levels, and so on. A few representative embodiments are described below.

The AKAP9 polypeptide or fragment employed in such a test can either be free in solution, affixed to a solid support, or borne on a cell surface. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an AKAP9 polypeptide or fragment and the agent being tested, or examine the degree to which the formation of a complex between an AKAP9 polypeptide or fragment and a known ligand, e.g., AKAP9 receptor (e.g., InsP$_3$R1, NMDA receptor, and CLIC4) or an AKAP9 interacting protein (e.g., PKA-R, PKN, PP1, PP2A-PR130, TACC4, TACC3, CIP4, PKCepsilon, and PDE4D3.), is modulated by the agent being tested.

Thus, the present invention provides methods of screening for drugs comprising contacting such an agent with an AKAP9 polypeptide or fragment thereof and assaying (i) for the presence of a complex between the agent and the AKAP9 polypeptide or fragment, or (ii) for the presence of a complex between the AKAP9 polypeptide or fragment and a ligand, by methods well known in the art. In such competitive binding assays the AKAP9 polypeptide or fragment is typically labeled. Free AKAP9 polypeptide or fragment is separated from that present in a protein:protein complex, and the amount of free (i.e., uncomplexed) label is a measure of the binding of the agent being tested to AKAP9 or its interference with AKAP9:ligand binding, respectively.

Another technique for drug screening provides high throughput screening for compounds having suitable binding affinity to the AKAP9 polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with AKAP9 polypeptides and washed. Bound AKAP9 polypeptides are then detected by methods well known in the art.

Purified AKAP9 can be coated directly onto plates for use in the aforementioned drug screening techniques. However, non-neutralizing antibodies to the polypeptide can be used to capture antibodies to immobilize the AKAP9 polypeptide on the solid phase.

This invention also contemplates the use of competitive drug screening assays in which neutralizing antibodies capable of specifically binding the AKAP9 polypeptide compete with a test compound for binding to the AKAP9 polypeptide or fragments thereof. In this manner, the antibodies can be used to detect the presence of any peptide which shares one or more antigenic determinants of the AKAP9 polypeptide.

A further technique for drug screening involves the use of host eukaryotic cell lines or cells (such as described above) which express a wild-type or mutant AKAP9 gene and as a consequence of expression of wild type or mutant AKAP9 demonstrate a specific phenotype. The phenotype of the cell's is examined to determine if the compound is capable of modulating the phenotype and thereby AKAP9 function.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel, P. L., et al. (1993) In: Cellular Interactions in Development: A Practical Approach, Oxford University Press, pp. 153-179; Fields, S, and Song, O-K. *Nature* 340:245-246 (1989); Chevray, P.M. and Nathans, D. N. *Proc. Natl. Acad. Sci. USA* 89:5789-5793 (1992); Lee, J. E., et al. *Science* 268:836-844 (1995)). This system can be used as a coarse screen prior to testing a substance for actual ability to modulate activity of the polypeptide. Alternatively, the screen could be used to screen test substances for binding to an AKAP9 specific binding partner, or to find mimetics of an AKAP9 polypeptide.

In another embodiment, the invention provides methods of screening for inhibitors of AKAP9 activity or an altered AKAP9 activity. In one aspect of this embodiment, the assays are configured to identify compounds that inhibit the ability of AKAP9 to activate a signaling pathway. The ability of AKAP9 to activate a signaling pathway can be determined by, e.g., analyzing the ability of AKAP9 to modulate PKA activity or the activity of other AKAP9 interacting proteins. The AKAP9-based screening can employ wild-type AKAP9 protein or a mutant AKAP9 protein as disclosed herein.

The invention provides screening assays for identifying inhibitors that disrupt the interaction between AKAP9, particularly an altered (mutant) AKAP9, and an AKAP9 receptor (InsP$_3$R1, NMDA receptor, and CLIC4) or an AKAP9 interacting partner (e.g., AKAP9, PKA-R, PKN, PP1, PP2A-PR130, TACC4, TACC3, CIP4, PKCepsilon, and PDE4D3). According to this embodiment, the screening methods are configured for selecting modulators of a protein complex formed between AKAP9 or a homologue, derivative, altered (mutant) form, or fragment thereof and at least one protein with which it interacts to (or a homologue, derivative, altered form, or fragment thereof). In a preferred aspect of this embodiment, the screening assays are configured to identify compounds that modulate an interaction between an altered AKAP9 and at least one protein with which it interacts to modulate an AKP9 mediated signaling pathway. Accordingly, the screen can use complexes comprising wild-type AKAP9 or altered AKAP9, to examine the effect of test compounds on AKAP9 mediated signaling. Comparing the results between the wild-type AKAP9 assays and the assays having an altered AKAP9 can allow for the identification of drug candidates that selectively modulate altered AKAP9 and/or its activation of an AKP9 mediated signaling pathway. Screening methods are also provided for selecting modulators of AKAP9. The compounds identified in the screening methods of the present invention can be used in preventing or ameliorating depression and related disorders.

Thus, test compounds can be screened in an in vitro binding assay to identify compounds capable of binding or affecting a protein-protein interaction between AKAP9 (including homologues, derivatives, altered (mutant) forms or fragments thereof) and proteins with which it interacts, such as AKAP9, an AKAP9 receptor, and AKAP9 interacting proteins (including homologues, derivatives, altered (mutant) forms, or fragments thereof). In addition, in vitro dissociation assays may also be employed to select compounds capable of dissociating or destabilizing the protein complexes comprising AKAP9 (or mutant AKAP9) identified in accordance with the present invention. An in vitro screening assay can also be used to identify compounds that trigger or initiate the formation of, or stabilize, a protein complex of the present invention. In preferred embodiments, in vivo assays such as yeast two-hybrid assays and various derivatives thereof, preferably reverse two-hybrid assays, are utilized in identifying compounds that interfere with or disrupt protein-protein interactions between AKAP9 or a homologue, derivative, altered form, mutant, or fragment thereof and an interacting partner which it interacts with such as AKAP9, an AKAP9 receptor, or an AKAP9 interacting protein (or a homologue, derivative, altered form, mutant, or fragment thereof). In addition, systems such as yeast two-hybrid assays are also useful in selecting compounds capable of triggering or initiating, enhancing or stabilizing protein-protein interactions between AKAP9 or a homologue, derivative, altered form, mutant, or fragment thereof and a protein with which it interacts, such as AKAP9, an AKAP9 receptor, or an AKAP9 interacting protein (or a homologue, derivative, altered form, mutant, or fragment thereof). For example, the assays can entail (1) contacting the interacting members of the protein complex with each other in the presence of a test compound; and (2) detecting the interaction between the interacting members.

The test compounds may be screened in an in vitro assay to identify compounds capable of binding the protein complexes or interacting protein members thereof in accordance with the present invention. For this purpose, a test compound is contacted with a protein complex or an interacting protein member thereof under conditions and for a time sufficient to allow specific interaction between the test compound and the target components to occur, thereby resulting in the binding of the compound to the target, and the formation of a complex. Subsequently, the binding event is detected. Various screening techniques known in the art may be used in the present invention. The protein complexes and the interacting protein members thereof may be prepared by any suitable methods, e.g., by recombinant expression and Purification. The protein complexes and/or interacting protein members thereof (both are referred to as "target" hereinafter in this section) may be free in solution. A test compound may be mixed with a target forming a liquid mixture. The compound may be labeled with a detectable marker. Upon mixing under suitable conditions, the binding complex having the compound and the target can be co-immunoprecipitated and washed. The compound in the precipitated complex can be detected based on the marker on the compound.

In a preferred embodiment, the target is immobilized on a solid support or on a cell surface. Preferably, the target can be arrayed into a protein microchip according to methods well-known in the art. For example, a target may be immobilized directly onto a microchip substrate such as glass slides or onto multi-well plates using non-neutralizing antibodies, i.e., antibodies capable of binding to the target but do not substantially affect its biological activities. To affect the screening, test compounds can be contacted with the immobilized target to allow binding to occur to form complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To identify binding compounds, one may measure the formation of the target-test compound complexes or kinetics for the formation thereof. When combinatorial libraries of organic non-peptide non-nucleic acid compounds are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, *J. Am. Chem. Soc.*, 116:373-374 (1994) and Moran et al., *J. Am. Chem. Soc.*, 117:10787-10788 (1995), both of which are incorporated herein by reference.

Alternatively, the test compounds can be immobilized on a solid support, e.g., forming a microarray of test compounds. The target protein or protein complex is then contacted with the test compounds. The target can be labeled with any suitable detection marker. For example, the target can be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies can be used to detect any bound target thus identifying the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See, e.g., Sikela and Hahn, *Proc. Natl. Acad. Sci. USA,* 84:3038-3042 (1987). The probe can be labeled with a radioactive isotope or a fluorescence marker. Alternatively, the probe can be biotinylated and detected with a streptavidin-alkaline phosphatase conjugate. More conveniently, the bound probe can be detected with an antibody.

In yet another embodiment, a known ligand capable of binding to the target can be used in competitive binding assays. Complexes between the known ligand and the target can be formed and then contacted with test compounds. The ability of a test compound to interfere with the interaction between the target and the known ligand is measured. One exemplary ligand is an antibody capable of specifically binding the target. Particularly, such an antibody is especially useful for identifying peptides that share one or more antigenic determinants of the target protein complex or interacting protein members thereof.

In a specific embodiment, a protein complex used in the screening assay includes a hybrid protein which is formed by fusion of two interacting protein members or fragments or interaction domains thereof. The hybrid protein can also be designed such that it contains a detectable epitope tag fused thereto. Suitable examples of such epitope tags include sequences derived from, e.g., influenza virus hemagglutinin (HA), Simian Virus 5 (V5), polyhistidine (6×His), c-myc, lacZ, GST, and the like.

Test compounds may also be screened in in vitro assays to identify compounds capable of dissociating the protein complexes identified in accordance with the present invention. Thus, for example, dissociation of a protein complex comprising AKAP9 (or mutant AKAP9) and at least one interacting partner (such as AKAP9, an AKAP9 receptor, or an AKAP9 interacting protein (or a homologue, derivative, altered form, mutant, or fragment thereof)) following treatment with a test compound can be detected. Conversely, test compounds may also be screened to identify compounds capable of enhancing the interaction between AKAP9 (or altered AKAP9) and at least one interacting partner (such as AKAP9, an AKAP9 receptor, or an AKAP9 interacting protein (or a homologue, derivative, altered form, mutant, or fragment thereof) or stabilizing the protein complex formed by the proteins.

The assay can be conducted in similar manners as the binding assays described above. For example, the presence or absence of a particular protein complex can be detected by an antibody selectively immunoreactive with the protein complex. Thus, after incubation of the protein complex with a test compound, an immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Similarly, two proteins the interaction between which is to be enhanced can be incubated together with a test compound. Thereafter, a protein complex can be detected by the selectively immunoreactive antibody. The amount of protein complex can be compared to that formed in the absence of the test compound. Various other detection methods can be suitable in the dissociation assay, as will be apparent to a skilled artisan apprised of the present disclosure.

Protein complexes comprising AKAP9 (or mutant AKAP9) and an interacting partner including AKAP9, an AKAP9 receptor, or an AKAP9 interacting protein (or a homologue, derivative, altered form, mutant, or fragment thereof), can be used in screening assays to identify modulators of protein complexes comprising AKAP9. In addition, mutants, homologues, derivatives or fragments of AKAP9 and protein complexes containing such homologues, derivatives, mutants, or fragments may also be used in such screening assays. As used herein, the term "modulator" encompasses any compounds that can cause any form of alteration of the biological activities or functions of the proteins or protein complexes, including, e.g., enhancing or reducing their biological activities, increasing or decreasing their stability, altering their affinity or specificity to certain other biological molecules, etc. In addition, the term "modulator" as used herein also includes any compounds that simply bind AKAP9, mutant AKAP9, and/or the proteins complexes of the present invention. For example, a modulator can be an "interaction antagonist" capable of interfering with or disrupting or dissociating protein-protein interaction between AKAP9 or a homologue, fragment or derivative thereof. A modulator can also be an "interaction agonist" that initiates or strengthens the interaction between the protein members of the protein complex of the present invention, or homologues, fragments, mutants, or derivatives thereof.

Accordingly, the present invention provides screening methods for selecting modulators of AKAP9 or an altered form thereof, or protein complexes formed between an AKAP9, an AKAP9 receptor, or an AKAP9 interacting protein (or a homologue, derivative, altered form, mutant, or fragment thereof). The protein complex targets suitable in the screening assays of the present invention can be any embodiments of the protein complexes of the present invention. Preferably, protein fragments are used in forming the protein complexes. In specific embodiments, fusion proteins are used in which a detectable epitope tag is fused to an interacting protein or a homologue or derivative or fragment thereof. Suitable examples of such epitope tags include sequences derived from, e.g., influenza virus hemagglutinin (HA), Simian Virus 5 (V5), polyhistidine (6×His), c-myc, lacZ, GST, and the like. In addition, an interacting protein alone or a homologue or derivative or fragment thereof can also be used as a protein target in screening assays. Preferably, a detectable epitope tag is fused to the protein target. For example, compounds capable of binding to AKAP9 protein, a homologue, derivative, mutant, or fragment thereof selected by the screening assays can be tested for their ability to inhibit or interfere with the interactions between AKAP9 and AKAP9, an AKAP9 receptor, or an AKAP9 interacting protein (or a homologue, derivative, altered form, mutant, or fragment thereof).

The modulators selected in accordance with the screening methods of the present invention can be effective in modulating the functions or activities of AKAP9 alone, or the protein complexes comprising AKAP9 or mutant AKAP9. Such complexes can include AKAP9, an AKAP9 receptor, or an AKAP9 interacting protein (or a homologue, derivative, altered form, mutant, or fragment thereof). For example, compounds capable of binding the protein complexes can be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods of the present invention can be made into therapeutically or prophylactically effective drugs for preventing or ameliorating diseases, disorders or symptoms caused by or associated with protein complexes comprising AKAP9 (or mutant AKAP9) and AKAP9, an AKAP9 receptor, or an AKAP9 interacting protein (or a homologue, derivative, altered form, mutant, or fragment thereof), or AKAP9 separately. Alternatively, they can be used as leads to aid the design and identification of therapeutically or prophylactically effective compounds for diseases, disorders or symptoms caused by or associated with protein complexes comprising AKAP9 (or an mutant AKAP9) and AKAP9, an AKAP9 receptor, or an AKAP9 interacting protein (or a homologue, derivative, altered form, mutant, or fragment thereof), or AKAP9 separately. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

In addition, potentially useful agents also include incomplete proteins, i.e., fragments of the interacting protein members that are capable of binding to their respective binding partners in a protein complex but are defective with respect to their normal cellular functions. For example, binding domains of the interacting member proteins of a protein complex can be used as competitive inhibitors of the activities of the protein complex. As will be apparent to skilled artisans, derivatives, homologues, or mutants of the binding domains can also be used. Binding domains can be easily identified using molecular biology techniques, e.g., mutagenesis in combination with yeast two-hybrid assays. Preferably, the protein fragment used is a fragment of an interacting protein member having a length of less than 90%, 80%, more preferably less than 75%, 65%, 50%, or less than 40% of the full length of the protein member. In one embodiment, an AKAP9 receptor or an AKAP9 interacting protein (or a homologue, derivative, altered form, mutant, or fragment thereof) protein fragment is administered. In a specific embodiment, one or more of the interaction domains of an AKAP9 receptor or an AKAP9 interacting protein (or a homologue, derivative, altered form, mutant, or fragment thereof), are administered to cells or tissue in vitro, or are administered to a patient in need of such treatment. For example, suitable protein fragments can include polypeptides having a contiguous span of 4, 5, 6, 7, 8, 9, 10, 11, 12, 13, 14, 15, 18, 20 or 25, preferably from 4 to 30, 40 or 50 amino acids or more of the sequence of an AKAP9 receptor or an AKAP9 interacting protein (or a homologue, derivative, altered form, mutant, or fragment thereof) that are capable of interacting with AKAP9 or mutant AKAP9. Also, suitable protein fragments can also include peptides capable of binding AKAP9, or mutant AKAP9, and having an amino acid sequence of from 4 to 30 amino acids that is at least 75%, 80%, 82%, 85%, 87%, 90%, 95% or more identical to a contiguous span of amino acids of an AKAP9 receptor, or an AKAP9 interacting protein (or a homologue, derivative, altered form, mutant, or fragment thereof) of the same length. Alternatively, a polypeptide capable of interacting with an AKAP9 receptor or an AKAP9 interacting protein (or a homologue, derivative, altered form, mutant, or fragment thereof) and having a contiguous span of 4, 5, 6, 7, 8, 9, 10, 11, 12, 13, 14, 15, 18, 20 or 25, preferably from 4 to 30, 40 or 50, or more amino acids of the amino acid sequence of AKAP9 can be administered. Also, other examples of suitable compounds include a peptide capable of binding an AKAP9 receptor, or an AKAP9 interacting protein (or a homologue, derivative, altered form, mutant, or fragment thereof) and having an amino acid sequence of from 4 to 30, 40, 50 or more amino acids that is at least 75%, 80%, 82%, 85%, 87%, 90%, 95% or more identical to a contiguous span of amino acids of the same length from AKAP9. In addition, the administered compounds can also be an antibody or antibody fragment, preferably single-chain antibody immunoreactive with AKAP9, an AKAP9 receptor, an AKAP9 interacting protein (or a homologue, derivative, altered form, mutant, or fragment thereof), or a protein complex of the present invention.

The protein fragments suitable as competitive inhibitors can be delivered into cells by direct cell internalization, receptor mediated endocytosis, or via a "transporter." It is noted that when the target proteins or protein complexes to be modulated reside inside cells, the compound administered to cells in vitro or in vivo in the method of the present invention preferably is delivered into the cells in order to achieve optimal results. Thus, preferably, the compound to be delivered is associated with a transporter capable of increasing the uptake of the compound by cells harboring the target protein or protein complex. As used herein, the term "transporter" refers to an entity (e.g., a compound or a composition or a physical structure formed from multiple copies of a compound or multiple different compounds) that is capable of facilitating the uptake of a compound of the present invention by animal cells, particularly human cells. Typically, the cell uptake of a compound of the present invention in the presence of a "transporter" is at least 20% higher, preferably at least 40%, 50%, 75%, and more preferably at least 100% higher than the cell uptake of the compound in the absence of the "transporter." Many molecules and structures known in the art can be used as "transporters." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84-87 (1998), which is incorporated herein by reference. Penetratins transport molecules attached thereto across cytoplasmic membranes or nuclear membranes efficiently, in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminus is tryptophan, while the amino acids at positions 3 and 5 counting from either the N- or C-terminus are not both valine. Preferably, the helix 3 of the homeodomain of *Drosophila* Antennapedia is used as a transporter. More preferably, a peptide having a sequence of amino acid residues 43-58 of the homeodomain Antp is employed as a transporter. In addition, other naturally occurring homologs of the helix 3 of the homeodomain of *Drosophila* Antennapedia can be used. For example, homeodomains of Fushi-tarazu and Engrailed have been shown to be capable of transporting peptides into cells. See Han et al., *Mol. Cells*, 10:728-32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272:16010-16017 (1997); Schwarze et al., *Science*, 285:1569-1572 (1999). It is known that the sequence responsible for cellular uptake consists of the highly basic region, amino acid residues 49-57. See, e.g., Vives et al., *J. Biol. Chem.*, 272:16010-16017 (1997); Wender et al., *Proc. Nat. Acad. Sci. USA*, 97:13003-13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569-1572 (1999). Any HIV tat-derived peptides or peptoid analogs thereof capable of transporting macromolecules such as peptides can be used for purposes of the present invention. For example, any native tat peptides having the highly basic region, amino acid residues 49-57 can be used as a transporter by covalently linking it to the compound to be delivered. In addition, various analogs of the tat peptide of amino acid residues 49-57 can also be useful transporters for purposes of this invention. Examples of various such analogs are disclosed in Wender et al., *Proc. Nat. Acad. Sci. USA*, 97:13003-13008 (2000) (which is incorporated herein by reference) including, e.g., d-Tat49-57, retro-inverso isomers of l- or d-Tat49-57 (i.e., l-Tat57-49 and d-Tat57-49), L-arginine oligomers, D-arginine oligomers, L-lysine oligomers, D-lysine oligomers, L-histidine oligomers, D-histidine oligomers, L-ornithine oligomers, D-ornithine oligomers, and various homologues, derivatives (e.g., modified forms with conjugates linked to the small peptides) and peptoid analogs thereof.

Other useful transporters known in the art include, but are not limited to, short peptide sequences derived from fibroblast growth factor (See Lin et al., *J. Biol. Chem.*, 270:14255-14258 (1998)), Galparan (See Pooga et al., *FASEB J.* 12:67-77 (1998)), and HSV-1 structural protein VP22 (See Elliott and O'Hare, *Cell*, 88:223-233 (1997)). As the above-described various transporters are generally peptides, fusion proteins can be conveniently made by recombinant expression to contain a transporter peptide covalently linked by a peptide bond to a competitive protein fragment. Alternatively, conventional methods can be used to chemically synthesize a transporter peptide or a peptide of the present invention or both.

The hybrid peptide can be administered to cells or tissue in vitro or to patients in a suitable pharmaceutical composition. In addition to peptide-based transporters, various other types of transporters can also be used, including but not limited to cationic liposomes (see Rui et al., *J. Am. Chem. Soc.*, 120: 11213-11218 (1998)), dendrimers (Kono et al., *Bioconjugate Chem.*, 10:1115-1121 (1999)), siderophores (Ghosh et al., *Chem. Biol.*, 3:1011-1019 (1996)), etc. In a specific embodiment, the compound according to the present invention is encapsulated into liposomes for delivery into cells. Additionally, when a compound according to the present invention is a peptide, it can be administered to cells by a gene therapy method. That is, a nucleic acid encoding the peptide can be administered to cells in vitro or to cells in a human or animal body. Any suitable gene therapy methods may be used for purposes of the present invention. Various gene therapy methods are well known in the art. Successes in gene therapy have been reported recently. See e.g., Kay et al., Nature Genet., 24:257-61 (2000); Cavazzana-Calvo et al., *Science,* 288:669 (2000); and Blaese et al., *Science,* 270: 475 (1995); Kantoff, et al., *J. Exp. Med.,* 166:219 (1987).

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, *J. Bio/Technology* 9:19-21 (1991). Rational drug design can be performed as described herein or using well known techniques, such as described in U.S. Pat. Nos. 5,800,998 and 5,891,628, each incorporated herein by reference.

In one approach, one first determines the three-dimensional structure of a protein of interest (e.g., AKAP9 polypeptide, fragments of the AKAP9 polypeptide, or AKAP9 signaling complex (Acehan et al. *Mol. Cell.* 9:423-432 (2002))) or, for example, of the AKAP9-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson, J. et al., Science 249:527-533 (1990)). In addition, peptides (e.g., AKAP9 polypeptide or fragments thereof) are analyzed by an alanine scan (Wells, J. A. *Methods in Enzymol.* 202:390-411 (1991)). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore. Thus, one may design drugs which have, e.g., improved AKAP9 polypeptide activity or stability or which act as inhibitors, agonists, antagonists, etc. of AKAP9 polypeptide activity.

Following identification of a substance which modulates or affects polypeptide activity, the substance can be investigated further. Furthermore, it can be manufactured and/or used in preparation, i.e., manufacture or formulation, or a composition such as a medicament, pharmaceutical composition or drug. These substances can be administered to individuals.

Thus, the present invention extends in various aspects not only to a substance identified using a nucleic acid molecule as a modulator of polypeptide activity, in accordance with what is disclosed herein, but also to a pharmaceutical composition, medicament, drug or other composition comprising such a substance, a method comprising administration of such a composition comprising such a substance, a method comprising administration of such a composition to a patient, e.g., for treatment or prophylaxis of depression, use of such a substance in the manufacture of a composition for administration, e.g., for treatment or prophylaxis of depression, and a method of making a pharmaceutical composition comprising admixing such a substance with a pharmaceutically acceptable excipient, vehicle or carrier, and optionally other ingredients.

A substance identified as a modulator of polypeptide function can be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Based Therapies

According to the present invention, a method is also provided of supplying wild-type AKAP9 function to a cell which carries mutant AKAP9 alleles. The wild-type AKAP9 gene or a part of the gene can be introduced into the cell in a vector such that the gene remains extrachromosomal. In such a situation, the gene will be expressed by the cell from the extrachromosomal location. If a gene fragment is introduced and expressed in a cell carrying a mutant AKAP9 allele, the gene fragment should encode a part of the AKAP9 protein which is required for normal physiological processes of the cell. More preferred is the situation where the wild-type AKAP9 gene or a part thereof is introduced into the mutant cell in such a way that it recombines with the endogenous mutant AKAP9 gene present in the cell. Such recombination requires a double recombination event which results in the correction of the AKAP9 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the routineer. See also U.S. Pat. Nos. 5,800,998 and 5,891,628, each incorporated by reference herein. Among the compounds which may exhibit antidepression activity are antisense, siRNA, ribozyme, and triple helix molecules. Such molecules may be designed to reduce or inhibit mutant AKAP9 activity. Techniques for the production and use of such molecules are well known to those of skill in the art, such as described herein or in U.S. Pat. No. 5,800,998, incorporated herein by reference.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the AKAP9 nucleotide sequence of interest, are preferred.

In one embodiment, the inhibitors of cellular levels of AKAP9 are double-stranded small interfering RNA (siRNA) compounds or a modified equivalent thereof. AKAP9 are commercially available from, for example, Dharmacon (Lafayette, Colo.) (citing Lassus et al. *Science* 297:1352-1354 (2002)). Alternatively, the skilled artisan, apprised of this disclosure, is capable of providing siRNA useful for reducing the levels of AKAP9 protein (or mutants thereof).

As is generally known in the art, siRNA compounds are RNA duplexes comprising two complementary single-stranded RNAs of 21 nucleotides that form 19 base pairs and possess 3' overhangs of two nucleotides. See Elbashir et al., *Nature* 411:494-498 (2001); and PCT Publication Nos. WO 00/44895; WO 01/36646; WO 99/32619; WO 00/01846; WO 01/29058; WO 99/07409; and WO 00/44914. When appropriately targeted via its nucleotide sequence to a specific mRNA in cells, a siRNA can specifically suppress gene expression through a process known as RNA interference (RNAi). See, e.g., Zamore & Aronin, *Nature Medicine*, 9:266-267 (2003). siRNAs can reduce the cellular level of specific mRNAs, and decrease the level of proteins coded by such mRNAs. siRNAs utilize sequence complementarity to target an mRNA for destruction, and are sequence-specific. Thus, they can be highly target-specific, and in mammals have been shown to target mRNAs encoded by different alleles of the same gene. Because of this precision, side effects typically associated with traditional drugs can be reduced or eliminated. In addition, they are relatively stable, and like antisense and ribozyme molecules, they can also be modified to achieve improved pharmaceutical characteristics, such as increased stability, deliverability, and ease of manufacture. Moreover, because siRNA molecules take advantage of a natural cellular pathway, i.e., RNA interference, they are highly efficient in destroying targeted mRNA molecules. As a result, it is relatively easy to achieve a therapeutically effective concentration of an siRNA compound in patients. Thus, siRNAs are a new class of drugs being actively developed by pharmaceutical companies.

In vivo inhibition of specific gene expression by RNAi was achieved in various organisms including mammals. For example, Song et al., *Nature Medicine*, 9:347-351 (2003) demonstrate that intravenous injection of Fas siRNA compounds into laboratory mice with autoimmune hepatitis specifically reduced Fas mRNA levels and expression of Fas protein in mouse liver cells. The gene silencing effect persisted without diminution for 10 days after the intravenous injection. The injected siRNA was effective in protecting the mice from liver failure and fibrosis. Song et al., *Nature Medicine*, 9:347-351 (2003). Several other approaches for delivery of siRNA into animals have also proved to be successful. See, e.g., McCaffery et al., *Nature*, 418:38-39 (2002); Lewis et al., *Nature Genetics*, 32:107-108 (2002); and Xia et al., *Nature Biotech.*, 20:1006-1010 (2002).

The siRNA compounds provided according to the present invention can be synthesized using conventional RNA synthesis methods. For example, they can be chemically synthesized using appropriately protected ribonucleoside phosphoramidites and a conventional DNA/RNA synthesizer. Various applicable methods for RNA synthesis are disclosed in, e.g., Usman et al., *J. Am. Chem. Soc.*, 109:7845-7854 (1987) and Scaringe et al., *Nucleic Acids Res.*, 18:5433-5441 (1990). Custom siRNA synthesis services are available from commercial vendors such as Ambion (Austin, Tex., USA), Dharmacon Research (Lafayette, Colo., USA), Pierce Chemical (Rockford, Ill., USA), ChemGenes (Ashland, Mass., USA), Proligo (Hamburg, Germany), and Cruachem (Glasgow, UK).

The siRNA compounds can also be various modified equivalents of the structures in of any AKAP9 siRNA. As used herein, "modified equivalent" means a modified form of a particular siRNA compound having the same target-specificity (i.e., recognizing the same mRNA molecules that complement the unmodified particular siRNA compound). Thus, a modified equivalent of an unmodified siRNA compound can have modified ribonucleotides, that is, ribonucleotides that contain a modification in the chemical structure of an unmodified nucleotide base, sugar and/or phosphate (or phosphodiester linkage). As is known in the art, an "unmodified ribonucleotide" has one of the bases adenine, cytosine, guanine, and uracil joined to the 1' carbon of beta-D-ribofuranose. Preferably, modified siRNA compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821;

5,541,306; 5,550,111; 5,563,253; 5,571,799; 5,587,361; and 5,625,050, each of which is herein incorporated by reference. Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Modified forms of siRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxymethyl)uridine, 5'-carboxymethylaminomethyl-2-thiouridine, 5-carboxymethylaminomethyluridine, 5-5-methylammomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., *Nucleic Acids Res.*, 22:2183 (1994), each of which is incorporated herein by reference in its entirety.

In addition, modified siRNA compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,0531 5,639,873; 5,646,265; 5,658,873; 5,670,633; and 5,700,920, each of which is herein incorporated by reference. Modified siRNA compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman and Cedergren, *Trends in Biochem. Sci.*, 17:334 (1992).

Preferably, the 3' overhangs of the siRNAs of the present invention are modified to provide resistance to cellular nucleases. In one embodiment the 3' overhangs comprise 2'-deoxyribonucleotides. In a preferred embodiment, these 3' overhangs comprise a dinucleotide made of two 2'-deoxythymine residues (i.e., dTdT) linked by a 5'-3' phosphodiester linkage.

siRNA compounds may be administered to mammals by various methods through different routes. For example, they can be administered by intravenous injection. See Song et al., *Nature Medicine*, 9:347-351 (2003). They can also be delivered directly to a particular organ or tissue by any suitable localized administration methods. Several other approaches for delivery of siRNA into animals have also proved to be successful. See, e.g., McCaffery et al., *Nature*, 418:38-39 (2002); Lewis et al., *Nature Genetics*, 32:107-108 (2002); and Xia et al., *Nature Biotech.*, 20:1006-1010 (2002). Alternatively, they may be delivered encapsulated in liposomes, by iontophoresis, or by incorporation into other vehicles such as hydrogels, cyclodextrins, biodegradable nanocapsules, and bioadhesive microspheres.

In addition, they can also be delivered by a gene therapy approach, using a DNA vector from which siRNA compounds in, e.g., small hairpin form (shRNA), can be transcribed directly. Recent studies have demonstrated that while double-stranded siRNAs are very effective at mediating RNAi, short, single-stranded, hairpin-shaped RNAs can also mediate RNAi, presumably because they fold into intramolecular duplexes that are processed into double-stranded siRNAs by cellular enzymes. Sui et al., *Proc. Natl. Acad. Sci. U.S.A.*, 99:5515-5520 (2002); Yu et al., *Proc. Natl. Acad. Sci. U.S.A.*, 99:6047-6052 (2002); and Paul et al., *Nature Biotech.*, 20:505-508 (2002)). This discovery has significant and far-reaching implications, since the production of such shRNAs can be readily achieved in vivo by transfecting cells or tissues with DNA vectors bearing short inverted repeats separated by a small number of (e.g., 3 to 9) nucleotides that direct the transcription of such small hairpin RNAs. Additionally, if mechanisms are included to direct the integration of the transcription cassette into the host cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice. See generally Hannon, *Nature* 418:244-251 (2002) and Shi *Trends Genet.* 19:9-12 (2003); see also Xia et al. *Nature Biotech.* 20:1006-1010 (2002).

Additional siRNA compounds targeted at different sites of the mRNA corresponding to AKAP9 can also be designed and synthesized according to general guidelines provided herein and generally known to skilled artisans. See e.g., Elbashir, et al. (*Nature* 411:494-498 (2001)). For example, guidelines have been compiled into "The siRNA User Guide" which is available at the following web address: www.mpib-pc.gwdg.de/abteilungen/100/105/sirna.html.

Additionally, to assist in the design of siRNAs for the efficient RNAi-mediated silencing of any target gene, several siRNA supply companies maintain web-based design tools that utilize these general guidelines for "picking" siRNAs when presented with the mRNA or coding DNA sequence of the target gene. Examples of such tools can be found at the web sites of Dharmacon, Inc. (Lafayette, Colo.), Ambion, Inc. (Austin, Tex.), an of approximately 30-50%; (3) lack of trinucleotide repeats, especially GGG and CCC, and (4) being unique to the target gene (i.e., sequences that share no significant homology with genes other than the one being targeted), so that other genes are not inadvertently targeted by the same siRNA designed for this particular target sequence. Another criterion to be considered is whether or not the target sequence includes a known polymorphic site. If so, siRNAs designed to target one particular allele may not effectively target another allele, since single base mismatches between the target sequence and its complementary strand in a given siRNA can greatly reduce the effectiveness of RNAi induced by that siRNA. Given that target sequence and such design tools and design criteria, an ordinarily skilled artisan apprised of the present disclosure should be able to design and synthesized additional siRNA compounds useful in reducing the mRNA level and therefore AKAP9 protein level which can be used to treat depression according to the invention.

In another embodiment, the inhibitors of cellular levels of AKAP9 are antisense compounds, or a modified equivalent thereof. These antisense compounds and methods can be employed to treat and/or prevent depression according to the therapeutic methods of the invention. The antisense compounds according to this embodiment specifically inhibit the expression of AKAP9. As is known in the art, antisense drugs generally act by hybridizing to a particular target nucleic acid thus blocking gene expression (particularly protein translation from mRNA). Methods for designing antisense compounds and using such compounds in treating diseases are well known and well developed in the art. For example, the antisense drug Vitravene® (fomivirsen), a 21-base long oligonucleotide, has been successfully developed and marketed by Isis Pharmaceuticals, Inc. for treating cytomegalovirus (CMV)-induced retinitis.

Antisense compounds useful in inhibiting protein translation from the AKAP9 mRNA can also be designed and prepared by an ordinary skilled artisan. Any methods for designing and making antisense compounds may be used for purpose of the present invention. See generally, Sanghvi et al., eds., Antisense Reseach and Applications, CRC Press, Boca Raton, 1993. Typically, antisense compounds are oligonucleotides designed based on the nucleotide sequence of the host cell's protein(s) involved in viral budding (or egress) mRNA or gene. As used herein, the term "specifically hybridize" or variations thereof means a sufficient degree of complementarity or pairing between an antisense oligo and a target DNA or mRNA such that stable and specific binding occurs therebetween. In particular, 100% complementarity or pairing is desirable but not required. Specific hybridization occurs when sufficient hybridization occurs between the antisense compound and its intended target nucleic acids in the substantial absence of non-specific binding of the antisense compound to non-target sequences under predetermined conditions, e.g., for purposes of in vivo treatment, preferably under physiological conditions. Preferably, specific hybridization results in the interference with normal expression of the gene product encoded by the target DNA or mRNA. For example, an antisense compound can be designed to specifically hybridize to the replication or transcription regulatory regions of a target gene, or the translation regulatory regions such as translation initiation region and exon/intron junctions, or the coding regions of a target mRNA.

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally-occurring oligonucleotides as described below. Typically an antisense compound of the present invention is an oligonucleotide having from about 6 to about 200, preferably from about 8 to about 30 nucleoside bases.

The antisense compounds preferably contain modified backbones or non-natural internucleoside linkages, including, but not limited to, modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference. Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Another useful modified oligonucleotide is peptide nucleic acid (PNA), in which the sugar-phosphate backbone of an oligonucleotide is replaced with an amide containing backbone, e.g., an aminoethylglycine backbone. See U.S. Pat. Nos. 5,539,082 and 5,714,331; and Nielsen et al. *Science* 254, 1497-1500 (1991), all of which are incorporated herein by reference. PNA antisense compounds are resistant to RNAse H digestion and thus exhibit longer half-lives within cells. In addition, various modifications may be made in PNA backbones to impart desirable drug profiles such as better stability, increased drug uptake, higher affinity to target nucleic acid, etc. Alternatively, the antisense compounds are oligonucleotides containing modified nucleosides, i.e., modified purine or pyrimidine bases, e.g., 5-substituted pyrimidines, 6-azapyrimidines, and N-2, N-6 and O-substituted purines, and the like. See e.g., U.S. Patent Nos. as well as U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, each of which is herein incorporated by reference in its entirety.

In addition, oligonucleotides with substituted or modified sugar moieties may also be used. For example, an antisense compound may have one or more 2'-O-methoxyethyl sugar moieties. See, e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,0531 5,639,873; 5,646,265; 5,658,873; 5,670,633; and 5,700,920, each of which is herein incorporated by reference.

Other types of oligonucleotide modifications are also useful including linking an oligonucleotide to a lipid, phospholipid or cholesterol moiety, cholic acid, thioether, aliphatic chain, polyamine, polyethylene glycol (PEG), or a protein or peptide. The modified oligonucleotides may exhibit increased uptake into cells, and/or improved stability, i.e., resistance to nuclease digestion and other biodegradation. See e.g., U.S. Pat. No. 4,522,811; Burnham *Am. J. Hosp. Pharm.* 15:210-218 (1994). Antisense compounds can be synthesized using any suitable methods known in the art. In fact, antisense compounds may be custom made by commercial suppliers. Alternatively, antisense compounds may be prepared using DNA/RNA synthesizers commercially available from various vendors, e.g., Applied Biosystems Group of Norwalk, Conn.

The antisense compounds can be formulated into a pharmaceutical composition with suitable carriers and administered into a patient using any suitable route of administration. Alternatively, the antisense compounds may also be used in a "gene-therapy" approach. That is, the oligonucleotide is subcloned into a suitable vector and transformed into human cells. The antisense oligonucleotide is then produced in vivo through transcription.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target AKAP9 mRNA, preferably the mutant AKAP9 mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding AKAP9, preferably mutant AKAP9 proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand.

In addition, nucleic acid molecules may be chosen that are purine-rich, for example, containing a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with one strand of a duplex first and then the other, eliminating the necessity for a sizeable stretch of either purines or pyrimidines to be present on one strand of a duplex.

It is possible that the siRNA, antisense, ribozyme, and/or triple helix molecules described herein may reduce or inhibit the translation of mRNA produced by both normal and mutant AKAP9 alleles. In order to ensure that substantial normal levels of AKAP9 activity are maintained in the cell, nucleic acid molecules that encode and express AKAP9 polypeptides exhibiting normal AKAP9 activity can be introduced into cells which do not contain sequences susceptible to the siRNA, antisense, ribozyme, or triple helix treatments. Such sequences can be introduced via gene therapy methods. Alternatively, it may be preferable to co-administer normal AKAP9 protein into the cell or tissue in order to maintain the requisite level of cellular or tissue AKAP9 activity.

Antisense RNA and DNA molecules, siRNA molecules, ribozyme molecules, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2'O-methyl rather than phosphodiesterase linkages within the oligodeoxyribonucleotide backbone.

Gene therapy would be carried out according to generally accepted methods, for example, as described in further detail in U.S. Pat. Nos. 5,837,492 and 5,800,998 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Methods of Use: Peptide Therapy

Peptides which have AKAP9 activity can be supplied to cells which carry mutant or missing AKAP9 alleles. Peptide therapy is performed as described herein or using well known techniques, such as described in U.S. Pat. Nos. 5,800,998 and 5,891,628, each incorporated herein by reference.

Protein can be produced by expression of the cDNA sequence in bacteria, for example, using known expression vectors. Alternatively, AKAP9 polypeptide can be extracted from AKAP9-producing mammalian cells. In addition, the techniques of synthetic chemistry can be employed to synthesize AKAP9 protein. Any of such techniques can provide the preparation of the present invention which comprises the AKAP9 protein. Preparation is substantially free of other human proteins. This is most readily accomplished by synthesis in a microorganism or in vitro.

Active AKAP9 molecules can be introduced into cells by microinjection or by use of liposomes, for example. Alternatively, some active molecules can be taken up by cells, actively or by diffusion. Extracellular application of the AKAP9 gene product can be sufficient to affect the development and or progression of depression. Supply of molecules with AKAP9 activity should lead to partial reversal of the depression phenotype. Other molecules with AKAP9 activity (for example, peptides, drugs or organic compounds) can also be used to effect such a reversal. Modified polypeptides having substantially similar function are also used for peptide therapy.

Alternatively, antibodies that are both specific for mutant AKAP9 gene product and interfere with its activity can be used. Such antibodies can be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include, but are not limited to, polyclonal, monoclonal, Fab fragments, F(ab')2 fragments, single chain antibodies, chimeric antibodies, humanized antibodies etc.

Method of Use: Indicating and/or Predicting a Susceptibility to an Alteration in Signal Transduction The invention provides a method for indicating an alteration in signal transduction and/or predicting a susceptibility to an alteration in signal transduction in a subject. According to one embodiment, the method involves detecting the presence or absence of an allelic variant of an AKAP9 gene, wherein the presence of the allelic variant is indicative of an alteration in signal transduction.

The alteration in signal transduction maybe related to disorders such as neurological disorders and depression.

Further provided are the above described methods for which the detecting step is by allele specific hybridization, primer specific extension, oligonucleotide ligation assay, restriction enzyme site analysis and single-stranded conformation polymorphism analysis.

Also provided are methods wherein the detecting is effected by mass spectrometry.

Further provided are methods wherein the detecting is effected by a signal moiety such as radioisotopes, enzymes, antigens, antibodies, spectrophotometric reagents, chemiluminescent reagents, fluorescent reagents and other light producing reagents.

As used herein, "signal transduction" refers to the propagation of a signal. In general, an extracellular signal is transmitted through the cell membrane to become an intracellular signal. This signal can then stimulate a cellular response. The term also encompasses signals that are propagated entirely within a cell. The polypeptide molecules involved in signal transduction processes are typically receptor and non-receptor protein kinases, receptor and non-receptor protein phosphatases, nucleotide exchange factors and transcription factors. One of the key biochemical mechanisms involved in signal transduction is protein phosphorylation. AKAP9 proteins are involved in signal transduction as they bind to protein kinase A (PKA) and are thought to anchor the kinase at a location, e.g., the plasma membrane, the Golgi membrane, the mitochondria, etc., where PKA acts to phosphorylate a specific substrate. Thus, an alteration in AKAP9 binding to PKA, localization to the mitochondria, or phosphorylation by PKA, among other steps will result in an alteration in signal transduction. Assays including those that determine phosphorylation by PKA, association of PKA and AKAP9 and localization of AKAP9 can be used to monitor the state of signal transduction.

Methods of Use: Transformed Hosts; Transgenic/Knockout Animals and Models

Similarly, cells and animals which carry a mutant AKAP9 allele can be used as model systems to study and test for substances which have potential as therapeutic agents. These can be isolated from individuals with AKAP9 mutations, either somatic or germline. Alternatively, the cell line can be engineered to carry the mutation in the AKAP9 allele, as described above. After a test substance is applied to the cells, the phenotype of the cell is determined. Any trait of the transformed cells can be assessed using techniques well known in the art. Transformed hosts, transgenic/knockout animals and models are prepared and used as described herein or using well known techniques, such as described in U.S. Pat. Nos. 5,800,998 and 5,891,628, each incorporated herein by reference.

Animals for testing therapeutic agents can be selected after mutagenesis of whole animals or after treatment of germline cells or zygotes. Such treatments include insertion of mutant AKAP9 alleles, usually from a second animal species, as well as insertion of disrupted homologous genes. Alternatively, the endogenous AKAP9 gene(s) of the animals can be disrupted by insertion or deletion mutation or other genetic alterations using conventional techniques (Capecchi, M. R. *Science* 244: 1288 (1989); Hasty, P., K., et al. *Nature* 350:243 (1991); Shinkai, Y., et al. *Cell* 68:855 (1992); Mombaerts, P., et al. *Cell* 68:869 (1992); Philpott, K. L., et al. *Science* 256:1448 (1992); Snouwaert, J. N., et al. *Science* 257:1083 (1992); Donehower, L. A., et al. *Nature* 356:215 (1992)) to produce knockout or transplacement animals. A transplacement is similar to a knockout because the endogenous gene is replaced, but in the case of a transplacement the replacement is by another version of the same gene. After test substances have been administered to the animals, the depression phenotype must be assessed. If the test substance prevents or suppresses the depression phenotype, then the test substance is a candidate therapeutic agent for the treatment of depression. These animal models provide an extremely important testing vehicle for potential therapeutic products.

In one embodiment of the invention, transgenic animals are produced which contain a functional transgene encoding a functional AKAP9 polypeptide or variants thereof. Transgenic animals expressing AKAP9 transgenes, recombinant cell lines derived from such animals and transgenic embryos may be useful in methods for screening for and identifying agents that induce or repress function of AKAP9. Transgenic animals of the present invention also can be used as models for studying indications such as depression.

In one embodiment of the invention, an AKAP9 transgene is introduced into a non-human host to produce a transgenic animal expressing a human, murine or other species AKAP9 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985) Mol. Cell. Biol. 8:1977-83; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It can be desirable to replace the endogenous AKAP9 by homologous recombination between the transgene or a mutant gene and the endogenous gene; or the endogenous gene may be eliminated by deletion as in the preparation of "knock-out" animals. Typically, an AKAP9 gene flanked by genomic sequences is transferred by microinjection into a fertilized egg. The microinjected eggs are implanted into a host female, and the progeny are screened for the expression of the transgene. Transgenic animals can be produced from the fertilized eggs from a number of animals including, but not limited to reptiles, amphibians, birds, mammals, and fish. Within a particularly preferred embodiment, transgenic mice are generated which overexpress AKAP9 or express a mutant form of the polypeptide. Alternatively, the absence of an AKAP9 in "knock-out" mice permits the study of the effects that loss of AKAP9 protein has on a cell in vivo. Knock-out mice also provide a model for the development of AKAP9-related depression.

Methods for producing knockout animals are generally described by Shastry (Shastry et al. *Experientia* 51:1028-1039 (1995); Shastry et al. *Mol. Cell. Biochem.* 181:163-179 (1998)) and Osterrieder and Wolf *Rev. Sci. Tech.* 17:351-364 (1998). The production of conditional knockout animals, in which the gene is active until knocked out at the desired time is generally described by Feil et al. *Proc. Natl. Acad. Sci. USA* 93:10887-10890 (1996); Gagneten et al. *Nucl. Acids Res.* 25:3326-3331 (1997); and Lobe & Nagy *Bioessays* 20:200-208 (1998). Each of these references is incorporated herein by reference.

As noted above, transgenic animals and cell lines derived from such animals can find use in certain testing experiments. In this regard, transgenic animals and cell lines capable of expressing wild-type or mutant AKAP9 can be exposed to test substances. These test substances can be screened for the ability to alter expression of wild-type AKAP9 or alter the expression or function of mutant AKAP9.

In a preferred aspect of the invention, compounds that are identified as modulators of AKAP9, apoptosome formation, and/or procaspase-9 activation, i.e., drug candidates for treating depression, are tested in animal or cell-based depression models. For example, a drug candidate identified in the screening of the invention methods of the invention is further tested in any of the abovementioned knock-out animal models to evaluate its therapeutic effect. Alternatively, a drug candidate identified in the screening of the invention methods of the invention is further tested in an animal depression model such as the forced swim test, the tail suspension test, learned helplessness test, chronic mild test stress, social stress test, early life stress test, olfactory bulbectomy test, fear conditioning test, anxiety based tests, reward based-tests, and cognition tests. See, e.g., Willner *Adv. Biochem. Psychopharmacol.* 49:19-41 (1995); Porsolt *Rev. Neurosci.* 11:53-58 (2000); and Nestler et al. *Neuron* 34:13-25 (2002).

Pharmaceutical Compositions and Routes of Administration

The AKAP9 polypeptides, antibodies, peptides and nucleic acids of the present invention can be formulated in pharmaceutical compositions, which are prepared according to conventional pharmaceutical compounding techniques. See, e.g., Remington's Pharmaceutical Sciences, 18th Ed. (1990, Mack Publishing Co., Easton, Pa.). The pharmaceutical compositions of the invention comprise a depression therapeutically effective amount of therapeutic compound. The methods of treating depression comprise administering to an individual in need of treatment a therapeutically effective amount of a pharmaceutical ingredient according to the invention. The composition can contain the active agent or pharmaceutically acceptable salts of the active agent. These compositions can comprise, in addition to one of the active substances, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets can be sugar-coated or enteric-coated by standard techniques. The active agent can be encapsulated to make it stable to passage through the gastrointestinal tract while at the same time allowing for passage across the blood brain barrier. See, e.g., WO 96/11698.

For parenteral administration, the compound can be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier can also contain other ingredients, for example, preservatives, suspending agents, solubilizing agents, buffers and the like. When the compounds are being administered intrathecally, they can also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the active agent more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

Instead of administering these agents directly, they can be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635 (all of which are herein incorporated by reference), designed for implantation in a patient. The vector can be targeted to the specific cells to be treated, or it can contain regulatory elements which are more tissue specific to the target cells. The cell based delivery system is designed to be implanted in a patient's body at the desired target site and contains a coding sequence for the active agent. Alternatively, the agent can be administered in a precursor form for conversion to the active form by an activating agent produced in, or targeted to, the cells to be treated. See for example, EP 425,731A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis, T., et al. (1982) Molecular Cloning: A Laboratory Manual (Cold Spring Harbor Laboratory, Cold Spring Harbor, N.Y.); Sambrook, J., et al. (1989) Molecular Cloning: A Laboratory Manual, 2nd Ed. (Cold Spring Harbor Laboratory, Cold Spring Harbor, N.Y.); Ausubel, F. M., et al. (1992) Current Protocols in Molecular Biology, (J. Wiley and Sons, NY); Glover, D. (1985) DNA Cloning, I and II (Oxford Press); Anand, R. (1992) Techniques for the Analysis of Complex Genomes, (Academic Press); Guthrie, G. and Fink, G. R. (1991) Guide to Yeast Genetics and Molecular Biology (Academic Press); Harlow and Lane (1988) Antibodies: A Laboratory Manual (Cold Spring Harbor Laboratory, Cold Spring Harbor, N.Y.; Jakoby, W. B. and Pastan, I. H. (eds.) (1979) Cell Culture. Methods in Enzymology, Vol. 58 (Academic Press, Inc., Harcourt Brace Jovanovich (NY); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Hogan et al. (eds) (1994) Manipulating the Mouse Embryo: A Laboratory Manual, 2nd Edition, Cold Spring Harbor Laboratory Press, Cold Spring Harbor, N.Y. A general discussion of techniques and materials for human gene mapping, including mapping of human chromosome 1, is provided, e.g., in White and Lalouel (1988) Ann. Rev. Genet. 22:259-279.

EXAMPLES

Example 1

Identification of an SNP Associated with Depression

To identify sequence variants associated with common diseases, variant discovery was carried out on all exons of the AKAP9 gene and 1 kb of upstream regulatory sequence. Thirty random individuals were selected for variant detection. Reference sequence for genomic and mRNA sequences were derived from public databases: Genome DNA was taken from GenBank accession nos. AC003086, AC000066, AC004013, AC000120, and mRNA sequence was referenced to GenBank accession no. NM_005751.

For each exon and 1000 bases upstream of exon1 two pairs of nested primers were designed using proprietary software, although, as the skilled artisan recognizes, other primer design software can be used. The nested primer pair was tailed with universal M13 primers. Primers were positioned to include a minimum of 30 bases of intronic sequence at either end of an exon in the final PCR product. This allows for examination of exon/intron boundaries. Large exons and continuous promoter sequence was amplified with overlapping primers sets. All amplicons were amplified using a robotic system and standard PCR conditions. PCR products were treated with shrimp alkaline phosphatase to remove free nucleotides and submitted to dye-primer sequencing using forward and reverse M13 sequencing primers. Products were separated on capillary sequencing machines (MegaBACE) and base-called using proprietary software, although, as the skilled artisan recognizes, other base-calling software can be used. Detection of variants was performed by proprietary software that compares individual base-called sequence traces to a reference sequence. All sequence, exon, primer, amplicon, polymorphism and genotype information was deposited in a relational database.

SNP Identified with Association to Major Depression

```
PID          Position                  Alleles  Location
crv624.56 ex.33@506ampl.26ds@135  A/G      K2484R SNP sequence in CRV624.56
agtccttacagaggatgctcttaaatccctagaaaatcagacatacttca
[A/G]

atcttttgaagaaaatggcaaaggttccataattaatttggaaacaaggt
(SEQ ID NO: 3)
```

A customized Taqman assay against the AKAP9 polymorphism was used to genotype a case/control sample set derived from Utah families segregating depression (DMV4 for depression phenotyping). 130 independent male cases, 142 independent female case and 453 Utah controls were assayed under standard conditions. Genotyping data were analysed using a one-sided Fisher's Exact test. The results were confirmed in an independent sample set collected in LA (Los Angeles, Calif.). N=number of samples, q=frequency, and P=the P-value (statistical significance via obe-sided Fischer's Exact test).

| Utah Samples | | | |
|---|---|---|---|
| Samples | Controls | Cases Male | Cases Female |
| N | 453 | 130 | 142 |
| q | 0.12 | 0.14 | 0.17 |
| P | | | 0.03 |

| Los Angeles Samples | | | | |
|---|---|---|---|---|
| Samples | LA Controls | LA Cases Male | LA Cases, Female | LA cases |
| N | 185 | 92 | 93 | 185 |
| q | | 0.12 | 0.12 | 0.17 |
| P | | 0.04 | 0.05 | 0.02 |

Example 2

Secondary Screen of AKAP9 Modulators in Animal Depression Models

Test compounds identified in the screens of the invention as potential depression therapeutics are desirably further tested in an animal depression model. The potential depression therapeutics can be tested in transgenic animals being homozygous or heterozygous for a mutant AKAP9. For example a transgenic animal being homozygous or heterozygous for a mutant AKAP9 will display a certain phenotype, animals treated with potential depression therapeutics that are capable of modifying depression are expected to modify that phenotype. Thus, a group of untreated animals can be compared to a group of animal treated with the potential depression therapeutic. The treated group is expected to display an improved phenotype. Any phenotypic measurement known to the skilled artisan can be used to assess the treatment.

Alternatively, the test compounds identified in the screens of the invention as potential depression therapeutics are desirably tested in an art-accepted animal depression model such as those in Willner *Adv. Biochem. Psychopharmacol.* 49:19-41 (1995); Porsolt Rev. Neurosci. 11:53-58 (2000); and Nestler et al. *Neuron* 34:13-25 (2002). These tests can include the forced swim test, the tail suspension test, learned helplessness test, chronic mild test stress, social stress test, early life stress test, olfactory bulbectomy test, fear conditioning test, anxiety based tests, reward based-tests, and cognition tests. A potential depression therapeutic identified in the screens of the invention has anti-depression activity if it increases the struggle time in the forced swim test, increases struggle time in the tail suspension test, decrease escape time and latency in the learned helplessness test, increased sexual behavior or sucrose preference in the chronic mild stress test, decrease behavioral abnormalities in the social stress test, reverse behavioral problems in the early life stress test, reverses behavioral abnormalities in the olfactory bulbectomy test, decreases fear-like response when exposed to previously neutral cues that have been associated with aversive stimuli, increase the degree to which an animal explores a particular environment in an anxiety based test, and so on.

Example 3

In Vitro Binding Assay to Identify AKAP9 Receptors and Binding Partners

See Huang et al. *PNAS* 272:8057-8064 (1997); Protein preparations containing AKAP9 are incubated with glutathione resin in PBS for 2 hours at 4 degrees Celsius with 0.1% Triton X-100, 1 mM phenylmethylsulfonyl fluoride, 1 mM EDTA, 5 mM benzamidine, and 5 mM B-mercaptoethanol and washed extensively with the same buffer. 200 micrograms of PKA regulatory subunit RII and/or RI are added to the resin and incubated at 4° C. Proteins associated with the AKAP9 are eluted and analyzed by Laemmli electrophoresis. The proteins are visualized by Coomassie Staining. PKA proteins can be radiolabeled or labeled with a fluorophore to allow detection.

Example 4

PKA Phosphorylation of Protein Substrate

Cyclic AMP-dependent protein kinase (PKA) catalyzes the transfer of gamma phosphate from adenosine triphosphate (ATP) to a serine or threonine residue in a protein substrate. A short synthetic peptide (Leucine-Arg-Arg-Alanine-Serine-Leucine-Glycine or LRRASLG) can be used as a substrate to assay the specific type of PKA activity as described in Pearson et. al. *Methods of Enzymology* 200:62-81 (1991).

The PKA assay can be carried out in a reaction of the enzyme with a peptide substrate and $\gamma^{32}$P-ATP followed by separation of the $^{32}$P-peptide product from the unreacted $\gamma^{32}$P-ATP on a phosphocellulose membrane. This method requires at least one basic amino acid residue in the peptide substrate. The peptide substrate can be tagged with a biotin group so that the biotinylated $^{32}$P-peptide product consistently binds to a streptavidin membrane in a manner independent of the peptide sequence as described in Goueli et al *Analytical Biochemistry* 225:10-17 (1995). The separation of the $^{32}$P-peptide product from the free $\gamma^{32}$P-ATP using affinity binding and ultrafiltration separation to analyze a mixture sample is described in U.S. Pat. No. 5,869,275. Thus, cells (or cell-free preparations) having an altered AKAP can be treated with a test compound to determine its effect on PKA signaling.

In some aspects and embodiments, compounds that increase PKA activity in the assays of the invention, or compounds that modulate AKAP9 activity to increase PKA activity are identified as compounds with antidepressant activity. In one aspect the assay involves monitoring cyclic AMP stimulated PKA activity in the presence and absence of a test compound.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. An in vitro method of detecting an AKAP9 single nucleotide polymorphism in a human subject comprising:
   identifying a human subject diagnosed with major depression or suspected of having major depression; and
   detecting, in an AKAP9 gene of a sample obtained from said human subject, a guanine in place of an adenine at position 7673 of SEQ ID NO:1.

* * * * *

SEQUENCE LISTING

```
<160> NUMBER OF SEQ ID NOS: 3

<210> SEQ ID NO 1
<211> LENGTH: 12462
<212> TYPE: DNA
<213> ORGANISM: Homo sapiens
<220> FEATURE:
```

```
<221> NAME/KEY: CDS
<222> LOCATION: (223)..(11946)

<400> SEQUENCE: 1
gaagatggcg gcggcggcgg cggtgacggc gcttcccgtg cggctgagga cgatccgcca      60
gtgagcgcgg agactgcttc cacttcgggc gggggagcgc cggaccgaat cggctctcta     120
ggccgtggag cttgccgtcc cacctccgtc caaatcgacc tttcctttct atccccaacc     180 accctcaac  ccctgttttc cctgccttc  cttgcagagg cc atg gag gac gag        234
                                                Met Glu Asp Glu
                                                 1 gag aga cag aag aag ctg gag gcc ggc aaa gcc aag ctt gcc cag ttt       282
Glu Arg Gln Lys Lys Leu Glu Ala Gly Lys Ala Lys Leu Ala Gln Phe
 5              10                  15                  20 cga caa aga aaa gct cag tcg gat ggg cag agt cct tcc aag aag cag       330
Arg Gln Arg Lys Ala Gln Ser Asp Gly Gln Ser Pro Ser Lys Lys Gln
             25                  30                  35 aaa aaa aag aga aaa acg tca agc agt aaa cat gat gtg tca gca cac       378
Lys Lys Lys Arg Lys Thr Ser Ser Ser Lys His Asp Val Ser Ala His
         40                  45                  50 cat gat ttg aat att gat caa tca cag tgt aat gaa atg tac ata aat       426
His Asp Leu Asn Ile Asp Gln Ser Gln Cys Asn Glu Met Tyr Ile Asn
     55                  60                  65 agt tct cag aga gta gaa tca act gtg att cct gaa tct aca ata atg       474
Ser Ser Gln Arg Val Glu Ser Thr Val Ile Pro Glu Ser Thr Ile Met
 70                  75                  80 aga act cta cat agt gga gaa ata acc agt cat gag cag ggc ttc tct       522
Arg Thr Leu His Ser Gly Glu Ile Thr Ser His Glu Gln Gly Phe Ser
 85                  90                  95                 100 gtg gaa ctg gaa agt gaa att tca acc aca gca gat gac tgc agt tca       570
Val Glu Leu Glu Ser Glu Ile Ser Thr Thr Ala Asp Asp Cys Ser Ser
                105                 110                 115 gag gta aat ggt tgc agt ttt gtg atg aga aca gga aag cct aca aat       618
Glu Val Asn Gly Cys Ser Phe Val Met Arg Thr Gly Lys Pro Thr Asn
            120                 125                 130 tta tta agg gaa gaa gaa ttt ggt gtt gat gat tct tat tct gaa caa       666
Leu Leu Arg Glu Glu Glu Phe Gly Val Asp Asp Ser Tyr Ser Glu Gln
        135                 140                 145 gga gca caa gac agt ccg act cat cta gag atg atg gaa agt gag ttg       714
Gly Ala Gln Asp Ser Pro Thr His Leu Glu Met Met Glu Ser Glu Leu
    150                 155                 160 gct ggg aag cag cat gag att gaa gag cta aac aga gag ctg gaa gaa       762
Ala Gly Lys Gln His Glu Ile Glu Glu Leu Asn Arg Glu Leu Glu Glu
165                 170                 175                 180 atg agg gtt acc tat ggg act gaa gga ctg cag cag tta caa gaa ttt       810
Met Arg Val Thr Tyr Gly Thr Glu Gly Leu Gln Gln Leu Gln Glu Phe
                185                 190                 195 gaa gct gcc att aaa caa aga gat ggc att ata acc cag ctc act gct       858
Glu Ala Ala Ile Lys Gln Arg Asp Gly Ile Ile Thr Gln Leu Thr Ala
            200                 205                 210 aat tta caa caa gca aga aga gaa aag gat gag aca atg aga gaa ttt       906
Asn Leu Gln Gln Ala Arg Arg Glu Lys Asp Glu Thr Met Arg Glu Phe
        215                 220                 225 tta gag ttg aca gaa cag agt caa aaa tta cag att caa ttt cag caa       954
Leu Glu Leu Thr Glu Gln Ser Gln Lys Leu Gln Ile Gln Phe Gln Gln
    230                 235                 240 tta cag gct agt gaa act ctg aga aac agc act cat agt agc aca gct      1002
Leu Gln Ala Ser Glu Thr Leu Arg Asn Ser Thr His Ser Ser Thr Ala
245                 250                 255                 260
```

```
gca gac tta cta caa gcc aaa caa cag atc ctc act cat caa cag cag     1050
Ala Asp Leu Leu Gln Ala Lys Gln Gln Ile Leu Thr His Gln Gln Gln
            265                 270                 275 ctt gaa gaa caa gac cac tta tta gaa gat tat cag aaa aag aaa gaa     1098
Leu Glu Glu Gln Asp His Leu Leu Glu Asp Tyr Gln Lys Lys Lys Glu
        280                 285                 290 gac ttc aca atg caa att agt ttc ttg caa gag aaa att aaa gta tat     1146
Asp Phe Thr Met Gln Ile Ser Phe Leu Gln Glu Lys Ile Lys Val Tyr
    295                 300                 305 gaa atg gaa caa gat aaa aaa gta gaa aac tca aat aaa gaa gaa ata     1194
Glu Met Glu Gln Asp Lys Lys Val Glu Asn Ser Asn Lys Glu Glu Ile
310                 315                 320 cag gaa aag gag aca atc att gaa gaa tta aac aca aaa ata ata gaa     1242
Gln Glu Lys Glu Thr Ile Ile Glu Glu Leu Asn Thr Lys Ile Ile Glu
325                 330                 335                 340 gaa gaa aag aaa act ctt gag cta aag gat aaa tta aca act gct gat     1290
Glu Glu Lys Lys Thr Leu Glu Leu Lys Asp Lys Leu Thr Thr Ala Asp
            345                 350                 355 aaa tta cta gga gaa tta caa gaa cag att gtg caa aag aac caa gaa     1338
Lys Leu Leu Gly Glu Leu Gln Glu Gln Ile Val Gln Lys Asn Gln Glu
        360                 365                 370 ata aaa aac atg aaa tta gag ctg act aat tct aag caa aaa gaa aga     1386
Ile Lys Asn Met Lys Leu Glu Leu Thr Asn Ser Lys Gln Lys Glu Arg
    375                 380                 385 cag tct tct gaa gaa ata aaa cag tta atg ggg aca gtc gaa gaa ctt     1434
Gln Ser Ser Glu Glu Ile Lys Gln Leu Met Gly Thr Val Glu Glu Leu
        390                 395                 400 cag aag aga aat cat aaa gac agc cag ttc gaa act gat ata gta caa     1482
Gln Lys Arg Asn His Lys Asp Ser Gln Phe Glu Thr Asp Ile Val Gln
405                 410                 415                 420 cga atg gaa caa gaa aca caa aga aag tta gaa caa ctc cgg gca gag     1530
Arg Met Glu Gln Glu Thr Gln Arg Lys Leu Glu Gln Leu Arg Ala Glu
            425                 430                 435 ctg gat gag atg tat ggg cag cag ata gtg caa atg aaa caa gaa tta     1578
Leu Asp Glu Met Tyr Gly Gln Gln Ile Val Gln Met Lys Gln Glu Leu
        440                 445                 450 ata aga caa cac atg gca cag atg gag gaa atg aaa aca cgg cat aag     1626
Ile Arg Gln His Met Ala Gln Met Glu Glu Met Lys Thr Arg His Lys
    455                 460                 465 gga gaa atg gag aat gct tta agg tca tat tca aat att aca gtt aat     1674
Gly Glu Met Glu Asn Ala Leu Arg Ser Tyr Ser Asn Ile Thr Val Asn
    470                 475                 480 gaa gat cag ata aag tta atg aat gtg gca ata aat gaa ctg aat ata     1722
Glu Asp Gln Ile Lys Leu Met Asn Val Ala Ile Asn Glu Leu Asn Ile
485                 490                 495                 500 aaa ttg caa gat act aac tct caa aag gaa aaa ctc aag gaa gaa cta     1770
Lys Leu Gln Asp Thr Asn Ser Gln Lys Glu Lys Leu Lys Glu Glu Leu
            505                 510                 515 gga cta att tta gaa gaa aag tgt gct cta cag aga cag ctt gaa gac     1818
Gly Leu Ile Leu Glu Glu Lys Cys Ala Leu Gln Arg Gln Leu Glu Asp
        520                 525                 530 ctt gtt gaa gaa ttg agc ttt tca agg gaa cag att cag aga gct aga     1866
Leu Val Glu Glu Leu Ser Phe Ser Arg Glu Gln Ile Gln Arg Ala Arg
    535                 540                 545 cag aca ata gct gaa caa gaa agt aaa ctt aat gaa gca cat aag tcc     1914
Gln Thr Ile Ala Glu Gln Glu Ser Lys Leu Asn Glu Ala His Lys Ser
    550                 555                 560 ctt agt aca gtg gaa gat ttg aaa gct gag att gtt tct gca tct gaa     1962
Leu Ser Thr Val Glu Asp Leu Lys Ala Glu Ile Val Ser Ala Ser Glu
565                 570                 575                 580
```

```
tcc aga aag gaa cta gaa tta aaa cat gaa gca gaa gtt aca aat tac       2010
Ser Arg Lys Glu Leu Glu Leu Lys His Glu Ala Glu Val Thr Asn Tyr
            585                 590                 595 aag ata aaa ctt gaa atg tta gaa aaa gaa aag aat gct gtg tta gac       2058
Lys Ile Lys Leu Glu Met Leu Glu Lys Glu Lys Asn Ala Val Leu Asp
600                 605                 610 aga atg gct gaa tca caa gaa gct gaa tta gag agg ctg aga aca cag       2106
Arg Met Ala Glu Ser Gln Glu Ala Glu Leu Glu Arg Leu Arg Thr Gln
            615                 620                 625 ctt cta ttt agt cac gaa gaa gag ctt tcc aaa ctg aag gaa gat tta       2154
Leu Leu Phe Ser His Glu Glu Glu Leu Ser Lys Leu Lys Glu Asp Leu
        630                 635                 640 gaa att gaa cat cga ata aat att gaa aaa ctt aaa gat aat tta ggc       2202
Glu Ile Glu His Arg Ile Asn Ile Glu Lys Leu Lys Asp Asn Leu Gly
645                 650                 655                 660 att cac tat aaa cag cag ata gat ggt tta cag aat gaa atg agt caa       2250
Ile His Tyr Lys Gln Gln Ile Asp Gly Leu Gln Asn Glu Met Ser Gln
            665                 670                 675 aag ata gaa acc atg cag ttt gaa aag gac aat ttg ata act aag cag       2298
Lys Ile Glu Thr Met Gln Phe Glu Lys Asp Asn Leu Ile Thr Lys Gln
        680                 685                 690 aat caa tta att ttg gaa att tca aag cta aaa gat tta cag cag tct       2346
Asn Gln Leu Ile Leu Glu Ile Ser Lys Leu Lys Asp Leu Gln Gln Ser
        695                 700                 705 ctt gta aat tca aag tca gaa gaa atg act ctt caa atc aat gaa ctt       2394
Leu Val Asn Ser Lys Ser Glu Glu Met Thr Leu Gln Ile Asn Glu Leu
        710                 715                 720 caa aaa gaa att gaa ata ctc aga caa gaa gaa aaa gaa aag ggt aca       2442
Gln Lys Glu Ile Glu Ile Leu Arg Gln Glu Glu Lys Glu Lys Gly Thr
725                 730                 735                 740 ctt gaa caa gaa gtt caa gaa tta caa ctt aaa aca gaa ttg tta gaa       2490
Leu Glu Gln Glu Val Gln Glu Leu Gln Leu Lys Thr Glu Leu Leu Glu
            745                 750                 755 aaa cag atg aag gaa aaa gag aat gat ctt caa gaa aaa ttt gca caa       2538
Lys Gln Met Lys Glu Lys Glu Asn Asp Leu Gln Glu Lys Phe Ala Gln
        760                 765                 770 ctt gaa gca gag aat agc att ctt aaa gat gaa aag aaa acc ctt gaa       2586
Leu Glu Ala Glu Asn Ser Ile Leu Lys Asp Glu Lys Lys Thr Leu Glu
        775                 780                 785 gac atg ttg aaa ata cat act cct gtt agc caa gaa gaa aga ttg att       2634
Asp Met Leu Lys Ile His Thr Pro Val Ser Gln Glu Glu Arg Leu Ile
790                 795                 800 ttc tta gac tcc att aag tcc aaa tcc aaa gac tct gtg tgg gaa aaa       2682
Phe Leu Asp Ser Ile Lys Ser Lys Ser Lys Asp Ser Val Trp Glu Lys
805                 810                 815                 820 gaa ata gaa ata ctt ata gag gaa aat gag gac ctc aaa caa caa tgt       2730
Glu Ile Glu Ile Leu Ile Glu Glu Asn Glu Asp Leu Lys Gln Gln Cys
            825                 830                 835 att cag cta aat gaa gag att gaa aag caa agg aac act ttt tca ttt       2778
Ile Gln Leu Asn Glu Glu Ile Glu Lys Gln Arg Asn Thr Phe Ser Phe
        840                 845                 850 gct gaa aaa aac ttt gaa gtt aac tat caa gag tta caa gag gag tat       2826
Ala Glu Lys Asn Phe Glu Val Asn Tyr Gln Glu Leu Gln Glu Glu Tyr
        855                 860                 865 gct tgc ctt ctc aaa gta aaa gat gat tta gaa gac agt aaa aat aaa       2874
Ala Cys Leu Leu Lys Val Lys Asp Asp Leu Glu Asp Ser Lys Asn Lys
870                 875                 880 cag gaa tta gag tat aaa agt aaa ctt aaa gca ctt aat gaa gag ctt       2922
Gln Glu Leu Glu Tyr Lys Ser Lys Leu Lys Ala Leu Asn Glu Glu Leu
```

-continued

```
      885              890              895              900
cat ttg caa aga ata aat cca act aca gtg aaa atg aaa agt tct gtc    2970
His Leu Gln Arg Ile Asn Pro Thr Thr Val Lys Met Lys Ser Ser Val
                 905              910              915 ttt gat gaa gac aaa act ttt gta gca gaa aca ttg gaa atg ggt gag    3018
Phe Asp Glu Asp Lys Thr Phe Val Ala Glu Thr Leu Glu Met Gly Glu
             920              925              930 gtt gtt gaa aag gat aca aca gaa ctc atg gaa aaa ctt gag gta acc    3066
Val Val Glu Lys Asp Thr Thr Glu Leu Met Glu Lys Leu Glu Val Thr
         935              940              945 aag cga gag aaa tta gag ctg tca cag aga ctg tct gat ctt tct gaa    3114
Lys Arg Glu Lys Leu Glu Leu Ser Gln Arg Leu Ser Asp Leu Ser Glu
     950              955              960 caa ttg aaa cag aaa cat ggt gag att agt ttt cta aat gaa gaa gtt    3162
Gln Leu Lys Gln Lys His Gly Glu Ile Ser Phe Leu Asn Glu Glu Val
965              970              975              980 aaa tct tta aag caa gag aaa gaa caa gtt tca ttg aga tgt aga gag    3210
Lys Ser Leu Lys Gln Glu Lys Glu Gln Val Ser Leu Arg Cys Arg Glu
                 985              990              995 cta gaa atc att att aac cac aac agg gca gaa aat gta cag tca        3255
Leu Glu Ile Ile Ile Asn His Asn Arg Ala Glu Asn Val Gln Ser
             1000             1005             1010 tgt gat act caa gta agc tct tta tta gat gga gtt gtg acc atg        3300
Cys Asp Thr Gln Val Ser Ser Leu Leu Asp Gly Val Val Thr Met
         1015             1020             1025 aca agc agg ggt gct gaa gga tca gtt tct aaa gta aat aaa agt        3345
Thr Ser Arg Gly Ala Glu Gly Ser Val Ser Lys Val Asn Lys Ser
     1030             1035             1040 ttt ggt gaa gaa tca aaa ata atg gtg gaa gat aaa gtt tct ttt        3390
Phe Gly Glu Glu Ser Lys Ile Met Val Glu Asp Lys Val Ser Phe
 1045             1050             1055 gaa aat atg act gtt gga gaa gaa agt aag caa gaa cag ttg att        3435
Glu Asn Met Thr Val Gly Glu Glu Ser Lys Gln Glu Gln Leu Ile
             1060             1065             1070 ttg gat cac tta cca tct gta aca aag gaa tca tca ctt aga gca        3480
Leu Asp His Leu Pro Ser Val Thr Lys Glu Ser Ser Leu Arg Ala
         1075             1080             1085 act caa cca agt gaa aat gat aaa ctt cag aaa gaa ctc aat gta        3525
Thr Gln Pro Ser Glu Asn Asp Lys Leu Gln Lys Glu Leu Asn Val
     1090             1095             1100 ctt aaa tca gaa cag aat gat tta agg cta cag atg gaa gcc caa        3570
Leu Lys Ser Glu Gln Asn Asp Leu Arg Leu Gln Met Glu Ala Gln
 1105             1110             1115 cgc att tgc ctc tct ctg gtt tat tca act cat gtg gat cag gtt        3615
Arg Ile Cys Leu Ser Leu Val Tyr Ser Thr His Val Asp Gln Val
             1120             1125             1130 cgt gaa tat atg gaa aat gaa aaa gat aaa gct ctt tgc agt ctt        3660
Arg Glu Tyr Met Glu Asn Glu Lys Asp Lys Ala Leu Cys Ser Leu
         1135             1140             1145 aaa gaa gag ctt att ttt gct caa gag gaa aag atc aag gaa ctt        3705
Lys Glu Glu Leu Ile Phe Ala Gln Glu Glu Lys Ile Lys Glu Leu
     1150             1155             1160 cag aaa ata cac cag tta gaa cta cag act atg aaa aca caa gaa        3750
Gln Lys Ile His Gln Leu Glu Leu Gln Thr Met Lys Thr Gln Glu
 1165             1170             1175 aca ggt gat gaa gga aag cct tta cat ctg ctc att gga aaa ctt        3795
Thr Gly Asp Glu Gly Lys Pro Leu His Leu Leu Ile Gly Lys Leu
             1180             1185             1190 caa aag gca gtg tct gaa gaa tgt tct tat ttt tta cag act tta        3840
```

```
                Gln Lys Ala Val Ser Glu Glu Cys Ser Tyr Phe Leu Gln Thr Leu
                            1195                1200                1205 tgc agt gtc ctt ggt gaa tat tat act cct gct tta aaa tgt gaa           3885
Cys Ser Val Leu Gly Glu Tyr Tyr Thr Pro Ala Leu Lys Cys Glu
        1210                1215                1220 gta aat gca gaa gac aaa gag aat tct ggt gat tac att tct gaa           3930
Val Asn Ala Glu Asp Lys Glu Asn Ser Gly Asp Tyr Ile Ser Glu
        1225                1230                1235 aat gaa gat cca gaa tta caa gat tat aga tat gaa gtt caa gac           3975
Asn Glu Asp Pro Glu Leu Gln Asp Tyr Arg Tyr Glu Val Gln Asp
        1240                1245                1250 ttt caa gaa aat atg cac act ctt ctc aac aaa gta aca gaa gaa           4020
Phe Gln Glu Asn Met His Thr Leu Leu Asn Lys Val Thr Glu Glu
        1255                1260                1265 tac aac aaa ctc ttg gta ctt caa aca cga cta agc aag atc tgg           4065
Tyr Asn Lys Leu Leu Val Leu Gln Thr Arg Leu Ser Lys Ile Trp
        1270                1275                1280 gga cag cag aca gat ggt atg aaa ctt gaa ttt gga gaa gaa aac           4110
Gly Gln Gln Thr Asp Gly Met Lys Leu Glu Phe Gly Glu Glu Asn
        1285                1290                1295 ctt cca aaa gag gaa aca gag ttt tta tca atc cat tct cag atg           4155
Leu Pro Lys Glu Glu Thr Glu Phe Leu Ser Ile His Ser Gln Met
        1300                1305                1310 acc aat ttg gaa gac att gat gtc aat cat aaa agc aag tta tct           4200
Thr Asn Leu Glu Asp Ile Asp Val Asn His Lys Ser Lys Leu Ser
        1315                1320                1325 tct ctg caa gat ctt gaa aaa act aaa ctt gaa gaa caa gtt caa           4245
Ser Leu Gln Asp Leu Glu Lys Thr Lys Leu Glu Glu Gln Val Gln
        1330                1335                1340 gaa tta gaa agc ctc ata tcc tct ttg cag caa cag ttg aaa gaa           4290
Glu Leu Glu Ser Leu Ile Ser Ser Leu Gln Gln Gln Leu Lys Glu
        1345                1350                1355 act gaa caa aac tat gag gca gag atc cac tgt tta cag aag agg           4335
Thr Glu Gln Asn Tyr Glu Ala Glu Ile His Cys Leu Gln Lys Arg
        1360                1365                1370 ctt caa gct gtt agt gag tcc acg gtt ccg cca agc tta cct gtt           4380
Leu Gln Ala Val Ser Glu Ser Thr Val Pro Pro Ser Leu Pro Val
        1375                1380                1385 gat tcg gtg gta att aca gaa tct gat gca cag aga aca atg tac           4425
Asp Ser Val Val Ile Thr Glu Ser Asp Ala Gln Arg Thr Met Tyr
        1390                1395                1400 cct gga agt tgt gtg aaa aag aat att gat ggt aca ata gag ttt           4470
Pro Gly Ser Cys Val Lys Lys Asn Ile Asp Gly Thr Ile Glu Phe
        1405                1410                1415 tct ggt gaa ttt gga gtg aaa gag gaa aca aat atc gtt aag ttg           4515
Ser Gly Glu Phe Gly Val Lys Glu Glu Thr Asn Ile Val Lys Leu
        1420                1425                1430 ctt gaa aaa caa tac caa gaa caa tta gaa gaa gaa gta gct aag           4560
Leu Glu Lys Gln Tyr Gln Glu Gln Leu Glu Glu Glu Val Ala Lys
        1435                1440                1445 gtt att gtg tca atg agt ata gca ttt gct caa caa act gaa ctg           4605
Val Ile Val Ser Met Ser Ile Ala Phe Ala Gln Gln Thr Glu Leu
        1450                1455                1460 tct aga ata tct ggg gga aaa gaa aat act gca tca tca aag caa           4650
Ser Arg Ile Ser Gly Gly Lys Glu Asn Thr Ala Ser Ser Lys Gln
        1465                1470                1475 gca cat gct gtg tgt cag caa gaa caa cat tat ttt aat gaa atg           4695
Ala His Ala Val Cys Gln Gln Glu Gln His Tyr Phe Asn Glu Met
        1480                1485                1490
```

```
aaa tta tca cag gat caa att ggt ttt cag act ttt gag aca gtg      4740
Lys Leu Ser Gln Asp Gln Ile Gly Phe Gln Thr Phe Glu Thr Val
        1495                1500                1505 gat gtg aaa ttt aaa gaa gaa ttt aaa cca ctt agt aaa gag tta      4785
Asp Val Lys Phe Lys Glu Glu Phe Lys Pro Leu Ser Lys Glu Leu
    1510                1515                1520 gga gaa cat gga aag gaa att tta tta tca aat agt gat ccc cat      4830
Gly Glu His Gly Lys Glu Ile Leu Leu Ser Asn Ser Asp Pro His
1525                1530                1535 gat ata cca gaa tca aag gac tgt gtg ctg act att tca gaa gaa      4875
Asp Ile Pro Glu Ser Lys Asp Cys Val Leu Thr Ile Ser Glu Glu
        1540                1545                1550 atg ttc tcc aaa gat aaa aca ttt ata gtt aga cag tct att cat      4920
Met Phe Ser Lys Asp Lys Thr Phe Ile Val Arg Gln Ser Ile His
    1555                1560                1565 gat gag att tca gtg tca agc atg gat gct tct aga caa cta atg      4965
Asp Glu Ile Ser Val Ser Ser Met Asp Ala Ser Arg Gln Leu Met
1570                1575                1580 ttg aat gaa gaa cag ttg gaa gat atg aga cag gaa ctt gta cga      5010
Leu Asn Glu Glu Gln Leu Glu Asp Met Arg Gln Glu Leu Val Arg
        1585                1590                1595 caa tac caa gaa cat caa cag gca acg gaa ttg tta agg caa gca      5055
Gln Tyr Gln Glu His Gln Gln Ala Thr Glu Leu Leu Arg Gln Ala
    1600                1605                1610 cat atg cgg caa atg gag aga cag cga gaa gac cag gaa cag cta      5100
His Met Arg Gln Met Glu Arg Gln Arg Glu Asp Gln Glu Gln Leu
1615                1620                1625 caa gaa gag att aag aga ctt aat aga caa tta gcc cag aga tcc      5145
Gln Glu Glu Ile Lys Arg Leu Asn Arg Gln Leu Ala Gln Arg Ser
        1630                1635                1640 tcc ata gat aat gaa aac ctg gtt tca gag aga gag agg gtg ctt      5190
Ser Ile Asp Asn Glu Asn Leu Val Ser Glu Arg Glu Arg Val Leu
    1645                1650                1655 tta gag gag ctg gaa gca cta aag cag ctg tct tta gct gga aga      5235
Leu Glu Glu Leu Glu Ala Leu Lys Gln Leu Ser Leu Ala Gly Arg
1660                1665                1670 gag aag ctg tgt tgt gag ctg cgc aac agc agt acg caa aca cag      5280
Glu Lys Leu Cys Cys Glu Leu Arg Asn Ser Ser Thr Gln Thr Gln
        1675                1680                1685 aat gga aat gaa aac caa gga gaa gtt gaa gaa caa aca ttt aaa      5325
Asn Gly Asn Glu Asn Gln Gly Glu Val Glu Glu Gln Thr Phe Lys
    1690                1695                1700 gaa aag gaa tta gac aga aaa cct gaa gat gtg cct cct gag att      5370
Glu Lys Glu Leu Asp Arg Lys Pro Glu Asp Val Pro Pro Glu Ile
1705                1710                1715 ttg tct aat gaa agg tat gca ctc cag aaa gct aat aat aga ctt      5415
Leu Ser Asn Glu Arg Tyr Ala Leu Gln Lys Ala Asn Asn Arg Leu
        1720                1725                1730 ttg aag atc ctc tta gaa gtt gta aag aca aca gca gct gtt gaa      5460
Leu Lys Ile Leu Leu Glu Val Val Lys Thr Thr Ala Ala Val Glu
    1735                1740                1745 gaa aca att ggt cgc cat gtc ctt ggg att cta gat aga tct agt      5505
Glu Thr Ile Gly Arg His Val Leu Gly Ile Leu Asp Arg Ser Ser
1750                1755                1760 aaa agc cag tca tct gcc agc cta att tgg agg tca gaa gca gag      5550
Lys Ser Gln Ser Ser Ala Ser Leu Ile Trp Arg Ser Glu Ala Glu
        1765                1770                1775 gca tct gta aag tca tgt gtc cat gag gaa cat aca aga gtt aca      5595
Ala Ser Val Lys Ser Cys Val His Glu Glu His Thr Arg Val Thr
    1780                1785                1790
```

-continued

| | | |
|---|---|---|
| gat gaa tcc att ccc tct tat tct gga agt gat atg cca aga aat<br>Asp Glu Ser Ile Pro Ser Tyr Ser Gly Ser Asp Met Pro Arg Asn<br>              1795                          1800                          1805 | 5640 |
| gac att aac atg tgg tca aaa gta act gag gaa gga aca gag ctg<br>Asp Ile Asn Met Trp Ser Lys Val Thr Glu Glu Gly Thr Glu Leu<br>              1810                          1815                          1820 | 5685 |
| tca caa cga ctt gtg agg agt ggt ttt gct gga act gaa ata gac<br>Ser Gln Arg Leu Val Arg Ser Gly Phe Ala Gly Thr Glu Ile Asp<br>              1825                          1830                          1835 | 5730 |
| cct gaa aat gaa gaa ctt atg ctg aac att agc tct cga cta caa<br>Pro Glu Asn Glu Glu Leu Met Leu Asn Ile Ser Ser Arg Leu Gln<br>              1840                          1845                          1850 | 5775 |
| gca gca gtt gaa aaa ctc cta gaa gcc ata agt gaa act agc agt<br>Ala Ala Val Glu Lys Leu Leu Glu Ala Ile Ser Glu Thr Ser Ser<br>              1855                          1860                          1865 | 5820 |
| cag ctt gaa cat gcg aaa gtg aca cag aca gag ttg atg cgt gag<br>Gln Leu Glu His Ala Lys Val Thr Gln Thr Glu Leu Met Arg Glu<br>              1870                          1875                          1880 | 5865 |
| tca ttt aga cag aaa caa gaa gca aca gag tcc ctt aag tgc caa<br>Ser Phe Arg Gln Lys Gln Glu Ala Thr Glu Ser Leu Lys Cys Gln<br>              1885                          1890                          1895 | 5910 |
| gag gaa ctt cga gag cgc ctt cat gag gag tcc agg gcc aga gaa<br>Glu Glu Leu Arg Glu Arg Leu His Glu Glu Ser Arg Ala Arg Glu<br>              1900                          1905                          1910 | 5955 |
| cag cta gct gtg gag ctc agt aag gct gag ggc gtc att gat ggc<br>Gln Leu Ala Val Glu Leu Ser Lys Ala Glu Gly Val Ile Asp Gly<br>              1915                          1920                          1925 | 6000 |
| tat gca gat gaa aaa act ctt ttt gaa agg caa att cag gaa aaa<br>Tyr Ala Asp Glu Lys Thr Leu Phe Glu Arg Gln Ile Gln Glu Lys<br>              1930                          1935                          1940 | 6045 |
| act gat ata ata gat cgt ctt gag cag gag ttg tta tgt gca agt<br>Thr Asp Ile Ile Asp Arg Leu Glu Gln Glu Leu Leu Cys Ala Ser<br>              1945                          1950                          1955 | 6090 |
| aac agg ttg caa gaa ttg gag gca gag caa cag cag atc caa gaa<br>Asn Arg Leu Gln Glu Leu Glu Ala Glu Gln Gln Gln Ile Gln Glu<br>              1960                          1965                          1970 | 6135 |
| gaa aga gaa tta ctg tcc aga caa aag gaa gct atg aaa gca gag<br>Glu Arg Glu Leu Leu Ser Arg Gln Lys Glu Ala Met Lys Ala Glu<br>              1975                          1980                          1985 | 6180 |
| gca ggc cca gtt gaa caa caa tta cta cag gag aca gaa aaa tta<br>Ala Gly Pro Val Glu Gln Gln Leu Leu Gln Glu Thr Glu Lys Leu<br>              1990                          1995                          2000 | 6225 |
| atg aag gaa aaa cta gaa gta caa tgt caa gct gaa aaa gta cgt<br>Met Lys Glu Lys Leu Glu Val Gln Cys Gln Ala Glu Lys Val Arg<br>              2005                          2010                          2015 | 6270 |
| gat gac ctt caa aaa caa gtg aaa gct cta gaa ata gat gtg gaa<br>Asp Asp Leu Gln Lys Gln Val Lys Ala Leu Glu Ile Asp Val Glu<br>              2020                          2025                          2030 | 6315 |
| gaa caa gtc agt agg ttt ata gag ctg gaa caa gaa aaa aat act<br>Glu Gln Val Ser Arg Phe Ile Glu Leu Glu Gln Glu Lys Asn Thr<br>              2035                          2040                          2045 | 6360 |
| gaa cta atg gat tta aga cag caa aac caa gca ttg gaa aag cag<br>Glu Leu Met Asp Leu Arg Gln Gln Asn Gln Ala Leu Glu Lys Gln<br>              2050                          2055                          2060 | 6405 |
| tta gaa aaa atg aga aaa ttt tta gat gag caa gcc att gac aga<br>Leu Glu Lys Met Arg Lys Phe Leu Asp Glu Gln Ala Ile Asp Arg<br>              2065                          2070                          2075 | 6450 |
| gaa cat gag aga gat gta ttc caa cag gaa ata cag aaa cta gaa<br>Glu His Glu Arg Asp Val Phe Gln Gln Glu Ile Gln Lys Leu Glu | 6495 |

-continued

```
                2080                2085                2090
cag caa ctt aag gtt gtt cct cga ttc cag cct atc agt gaa cat       6540
Gln Gln Leu Lys Val Val Pro Arg Phe Gln Pro Ile Ser Glu His
        2095                2100                2105 caa act aga gag gtt gaa cag tta gca aat cat ctg aaa gaa aaa       6585
Gln Thr Arg Glu Val Glu Gln Leu Ala Asn His Leu Lys Glu Lys
        2110                2115                2120 aca gac aaa tgc agt gag ctt ttg ctc tct aaa gag cag ctt caa       6630
Thr Asp Lys Cys Ser Glu Leu Leu Leu Ser Lys Glu Gln Leu Gln
        2125                2130                2135 agg gat ata caa gaa agg aat gaa gaa ata gag aaa ctg gag ttc       6675
Arg Asp Ile Gln Glu Arg Asn Glu Glu Ile Glu Lys Leu Glu Phe
        2140                2145                2150 aga gta aga gaa ctg gag cag gcg ctt ctt gtg agt gca gat act       6720
Arg Val Arg Glu Leu Glu Gln Ala Leu Leu Val Ser Ala Asp Thr
        2155                2160                2165 ttt caa aag gta gag gac cga aaa cac ttt gga gct gta gaa gct       6765
Phe Gln Lys Val Glu Asp Arg Lys His Phe Gly Ala Val Glu Ala
        2170                2175                2180 aaa cca gaa ttg tcc cta gaa gta caa ttg cag gct gaa cga gat       6810
Lys Pro Glu Leu Ser Leu Glu Val Gln Leu Gln Ala Glu Arg Asp
        2185                2190                2195 gcc ata gac aga aag gaa aaa gag att aca aac tta gaa gag caa       6855
Ala Ile Asp Arg Lys Glu Lys Glu Ile Thr Asn Leu Glu Glu Gln
        2200                2205                2210 tta gaa cag ttt aga gaa gaa ctg gaa aat aag aat gaa gaa gtt       6900
Leu Glu Gln Phe Arg Glu Glu Leu Glu Asn Lys Asn Glu Glu Val
        2215                2220                2225 caa caa tta cat atg caa tta gaa ata cag aaa aag gaa tct act       6945
Gln Gln Leu His Met Gln Leu Glu Ile Gln Lys Lys Glu Ser Thr
        2230                2235                2240 acc cgc cta caa gaa ctt gaa cag gaa aac aaa tta ttt aag gat       6990
Thr Arg Leu Gln Glu Leu Glu Gln Glu Asn Lys Leu Phe Lys Asp
        2245                2250                2255 gac atg gag aaa ctg gga ctt gcc ata aag gaa tct gat gcc atg       7035
Asp Met Glu Lys Leu Gly Leu Ala Ile Lys Glu Ser Asp Ala Met
        2260                2265                2270 tct act caa gac caa cat gtg cta ttt ggg aaa ttt gct caa ata       7080
Ser Thr Gln Asp Gln His Val Leu Phe Gly Lys Phe Ala Gln Ile
        2275                2280                2285 ata cag gaa aaa gag gta gaa att gac caa tta aat gaa caa gtt       7125
Ile Gln Glu Lys Glu Val Glu Ile Asp Gln Leu Asn Glu Gln Val
        2290                2295                2300 acg aaa ctc cag cag caa ctt aaa att aca aca gat aac aag gtt       7170
Thr Lys Leu Gln Gln Gln Leu Lys Ile Thr Thr Asp Asn Lys Val
        2305                2310                2315 att gaa gaa aaa aat gaa ctg ata agg gat ctt gaa acc caa ata       7215
Ile Glu Glu Lys Asn Glu Leu Ile Arg Asp Leu Glu Thr Gln Ile
        2320                2325                2330 gaa tgt ttg atg agt gat caa gaa tgt gtg aag aga aat aga gaa       7260
Glu Cys Leu Met Ser Asp Gln Glu Cys Val Lys Arg Asn Arg Glu
        2335                2340                2345 gaa gaa ata gag cag ctc aat gaa gtg att gaa aaa ctt caa cag       7305
Glu Glu Ile Glu Gln Leu Asn Glu Val Ile Glu Lys Leu Gln Gln
        2350                2355                2360 gaa ttg gca aat att gga cag aag aca tca atg aat gct cat tcc       7350
Glu Leu Ala Asn Ile Gly Gln Lys Thr Ser Met Asn Ala His Ser
        2365                2370                2375 ctc tca gaa gaa gca gac agt tta aaa cat caa ttg gat gtg gtt       7395
```

-continued

```
Leu Ser Glu Glu  Ala Asp Ser Leu Lys  His Gln Leu Asp  Val Val
        2380                  2385              2390 ata gct gaa aag  ctg gcc ttg gaa cag  caa gta gaa acc  gct aat              7440
Ile Ala Glu Lys  Leu Ala Leu Glu Gln  Gln Val Glu Thr  Ala Asn
        2395                  2400              2405 gaa gaa atg acc  ttc atg aaa aat gta  ctt aaa gaa acc  aat ttt              7485
Glu Glu Met Thr  Phe Met Lys Asn Val  Leu Lys Glu Thr  Asn Phe
        2410                  2415              2420 aaa atg aat cag  cta aca cag gaa tta  ttc agc tta aag  aga gaa              7530
Lys Met Asn Gln  Leu Thr Gln Glu Leu  Phe Ser Leu Lys  Arg Glu
        2425                  2430              2435 cgt gaa agt gtg  gaa aag att caa agc  ata cca gag aat  agt gtt              7575
Arg Glu Ser Val  Glu Lys Ile Gln Ser  Ile Pro Glu Asn  Ser Val
        2440                  2445              2450 aac gtg gct ata  gat cat ctg agc aaa  gac aaa cct gaa  cta gaa              7620
Asn Val Ala Ile  Asp His Leu Ser Lys  Asp Lys Pro Glu  Leu Glu
        2455                  2460              2465 gta gtc ctt aca  gag gat gct ctt aaa  tcc cta gaa aat  cag aca              7665
Val Val Leu Thr  Glu Asp Ala Leu Lys  Ser Leu Glu Asn  Gln Thr
        2470                  2475              2480 tac ttc ara tct  ttt gaa gaa aat ggc  aaa ggt tcc ata  att aat              7710
Tyr Phe Xaa Ser  Phe Glu Glu Asn Gly  Lys Gly Ser Ile  Ile Asn
        2485                  2490              2495 ttg gaa aca agg  ttg cta caa ctt gag  agc act gtt agt  gca aag              7755
Leu Glu Thr Arg  Leu Leu Gln Leu Glu  Ser Thr Val Ser  Ala Lys
        2500                  2505              2510 gac tta gaa ctt  acc cag tgt tat aaa  caa ata aaa gac  atg caa              7800
Asp Leu Glu Leu  Thr Gln Cys Tyr Lys  Gln Ile Lys Asp  Met Gln
        2515                  2520              2525 gaa caa ggc cag  ttt gaa aca gaa atg  ctt caa aag aag  att gta              7845
Glu Gln Gly Gln  Phe Glu Thr Glu Met  Leu Gln Lys Lys  Ile Val
        2530                  2535              2540 aac cta cag aaa  ata gtt gaa gaa aaa  gtg gct gct gct  ctt gtc              7890
Asn Leu Gln Lys  Ile Val Glu Glu Lys  Val Ala Ala Ala  Leu Val
        2545                  2550              2555 agt caa atc caa  ctt gag gca gtt cag  gaa tat gca aaa  ttc tgt              7935
Ser Gln Ile Gln  Leu Glu Ala Val Gln  Glu Tyr Ala Lys  Phe Cys
        2560                  2565              2570 caa gat aat caa  aca att tca tca gaa  cct gaa aga aca  aat att              7980
Gln Asp Asn Gln  Thr Ile Ser Ser Glu  Pro Glu Arg Thr  Asn Ile
        2575                  2580              2585 cag aat tta aat  caa cta aga gaa gat  gag ttg ggg tca  gat ata              8025
Gln Asn Leu Asn  Gln Leu Arg Glu Asp  Glu Leu Gly Ser  Asp Ile
        2590                  2595              2600 tca gca tta acc  ttg aga ata tca gaa  tta gaa agc cag  gtt gtt              8070
Ser Ala Leu Thr  Leu Arg Ile Ser Glu  Leu Glu Ser Gln  Val Val
        2605                  2610              2615 gaa atg cat act  agt ttg att tta gaa  aaa gaa caa gta  gaa att              8115
Glu Met His Thr  Ser Leu Ile Leu Glu  Lys Glu Gln Val  Glu Ile
        2620                  2625              2630 gca gaa aaa aat  gtt tta gaa aaa gaa  aag aag ctg cta  gaa cta              8160
Ala Glu Lys Asn  Val Leu Glu Lys Glu  Lys Lys Leu Leu  Glu Leu
        2635                  2640              2645 cag aag cta ttg  gag ggc aat gag aaa  aaa cag aga gag  aaa gaa              8205
Gln Lys Leu Leu  Glu Gly Asn Glu Lys  Lys Gln Arg Glu  Lys Glu
        2650                  2655              2660 aag aaa aga agc  cct caa gat gtt gaa  gtt ctc aag aca  act act              8250
Lys Lys Arg Ser  Pro Gln Asp Val Glu  Val Leu Lys Thr  Thr Thr
        2665                  2670              2675
```

```
gag cta ttt cat agc aat gaa gaa agt gga ttt ttt aat gaa ctc       8295
Glu Leu Phe His Ser Asn Glu Glu Ser Gly Phe Phe Asn Glu Leu
            2680                2685                2690 gag gct ctt aga gct gaa tca gtg gct acc aaa gca gaa ctt gcc       8340
Glu Ala Leu Arg Ala Glu Ser Val Ala Thr Lys Ala Glu Leu Ala
            2695                2700                2705 agt tat aaa gaa aag gct gaa aaa ctt caa gaa gag ctt ttg gta       8385
Ser Tyr Lys Glu Lys Ala Glu Lys Leu Gln Glu Glu Leu Leu Val
            2710                2715                2720 aaa gaa aca aat atg aca tct ctt cag aaa gac tta agc caa gtt       8430
Lys Glu Thr Asn Met Thr Ser Leu Gln Lys Asp Leu Ser Gln Val
            2725                2730                2735 agg gat cac ctc gca gag gca aaa gag aaa ttg tcc att tta gaa       8475
Arg Asp His Leu Ala Glu Ala Lys Glu Lys Leu Ser Ile Leu Glu
            2740                2745                2750 aaa gaa gat gag act gag gta caa gaa agc aaa aag gcc tgc atg       8520
Lys Glu Asp Glu Thr Glu Val Gln Glu Ser Lys Lys Ala Cys Met
            2755                2760                2765 ttt gag cca ctt cct ata aaa ctg agt aag agc att gca tcc cag       8565
Phe Glu Pro Leu Pro Ile Lys Leu Ser Lys Ser Ile Ala Ser Gln
            2770                2775                2780 aca gat ggg act ctg aag atc agt agc agc aat cag act cca caa       8610
Thr Asp Gly Thr Leu Lys Ile Ser Ser Ser Asn Gln Thr Pro Gln
            2785                2790                2795 att ctt gtt aaa aat gca gga ata caa att aat tta cag agt gaa       8655
Ile Leu Val Lys Asn Ala Gly Ile Gln Ile Asn Leu Gln Ser Glu
            2800                2805                2810 tgt tcc tca gaa gaa gtt act gaa ata atc agt cag ttt act gaa       8700
Cys Ser Ser Glu Glu Val Thr Glu Ile Ile Ser Gln Phe Thr Glu
            2815                2820                2825 aaa att gag aag atg caa gaa cta cat gct gct gaa att ttg gac       8745
Lys Ile Glu Lys Met Gln Glu Leu His Ala Ala Glu Ile Leu Asp
            2830                2835                2840 atg gaa tcc aga cat att tca gaa act gaa acc tta aag agg gaa       8790
Met Glu Ser Arg His Ile Ser Glu Thr Glu Thr Leu Lys Arg Glu
            2845                2850                2855 cac tat gtt gcc gtt cag tta ctg aaa gag gaa tgt ggt acc ttg       8835
His Tyr Val Ala Val Gln Leu Leu Lys Glu Glu Cys Gly Thr Leu
            2860                2865                2870 aag gca gtg ata cag tgt ctg aga agt aaa gag gga tcc tca att       8880
Lys Ala Val Ile Gln Cys Leu Arg Ser Lys Glu Gly Ser Ser Ile
            2875                2880                2885 cct gag cta gca cat tct gat gct tac cag act aga gaa ata tgc       8925
Pro Glu Leu Ala His Ser Asp Ala Tyr Gln Thr Arg Glu Ile Cys
            2890                2895                2900 tcc agt gat tct gga tca gac tgg ggt cag gga att tat ctt aca       8970
Ser Ser Asp Ser Gly Ser Asp Trp Gly Gln Gly Ile Tyr Leu Thr
            2905                2910                2915 cac agt cag gga ttt gac ata gca tca gaa ggc cga gga gaa gaa       9015
His Ser Gln Gly Phe Asp Ile Ala Ser Glu Gly Arg Gly Glu Glu
            2920                2925                2930 agt gaa agt gca aca gat tcc ttt cca aag aaa ata aag gga tta       9060
Ser Glu Ser Ala Thr Asp Ser Phe Pro Lys Lys Ile Lys Gly Leu
            2935                2940                2945 ctg aga gct gtc cat aat gaa ggc atg cag gtg ctt tct ctc act       9105
Leu Arg Ala Val His Asn Glu Gly Met Gln Val Leu Ser Leu Thr
            2950                2955                2960 gag tct ccc tat agt gat gga gag gac cat tct att cag cag gtt       9150
Glu Ser Pro Tyr Ser Asp Gly Glu Asp His Ser Ile Gln Gln Val
            2965                2970                2975
```

| | | | | | | | | | | | | |
|---|---|---|---|---|---|---|---|---|---|---|---|---|
| tca | gaa | cct | tgg | cta | gaa | gag | aga | aaa | gct | tac | atc | aat | aca | atc | 9195 |
| Ser | Glu | Pro | Trp | Leu | Glu | Glu | Arg | Lys | Ala | Tyr | Ile | Asn | Thr | Ile | |
| | | | 2980 | | | | 2985 | | | | | 2990 | | | |
| tca | tct | cta | aag | gat | tta | att | aca | aag | atg | caa | ctg | caa | aga | gaa | 9240 |
| Ser | Ser | Leu | Lys | Asp | Leu | Ile | Thr | Lys | Met | Gln | Leu | Gln | Arg | Glu | |
| | | | 2995 | | | | 3000 | | | | | 3005 | | | |
| gcc | gag | gtt | tat | gat | agt | tct | caa | tct | cat | gag | agc | ttc | tca | gac | 9285 |
| Ala | Glu | Val | Tyr | Asp | Ser | Ser | Gln | Ser | His | Glu | Ser | Phe | Ser | Asp | |
| | | | 3010 | | | | 3015 | | | | | 3020 | | | |
| tgg | cga | ggt | gaa | cta | ctg | ctt | gcc | ctt | caa | caa | gtt | ttc | tta | gaa | 9330 |
| Trp | Arg | Gly | Glu | Leu | Leu | Leu | Ala | Leu | Gln | Gln | Val | Phe | Leu | Glu | |
| | | | 3025 | | | | 3030 | | | | | 3035 | | | |
| gag | cgt | agt | gtt | tta | cta | gca | gca | ttt | cgg | acg | gag | ctg | aca | gct | 9375 |
| Glu | Arg | Ser | Val | Leu | Leu | Ala | Ala | Phe | Arg | Thr | Glu | Leu | Thr | Ala | |
| | | | 3040 | | | | 3045 | | | | | 3050 | | | |
| cta | ggt | act | aca | gat | gca | gtt | ggt | tta | cta | aac | tgt | ttg | gaa | cag | 9420 |
| Leu | Gly | Thr | Thr | Asp | Ala | Val | Gly | Leu | Leu | Asn | Cys | Leu | Glu | Gln | |
| | | | 3055 | | | | 3060 | | | | | 3065 | | | |
| aga | ata | caa | gaa | cag | ggt | gtt | gaa | tat | caa | gca | gct | atg | gaa | tgc | 9465 |
| Arg | Ile | Gln | Glu | Gln | Gly | Val | Glu | Tyr | Gln | Ala | Ala | Met | Glu | Cys | |
| | | | 3070 | | | | 3075 | | | | | 3080 | | | |
| ctc | cag | aaa | gca | gat | aga | agg | agt | ttg | tta | tct | gaa | att | cag | gca | 9510 |
| Leu | Gln | Lys | Ala | Asp | Arg | Arg | Ser | Leu | Leu | Ser | Glu | Ile | Gln | Ala | |
| | | | 3085 | | | | 3090 | | | | | 3095 | | | |
| ctg | cat | gca | caa | atg | aat | ggt | agg | aaa | att | act | ctg | aaa | aga | gaa | 9555 |
| Leu | His | Ala | Gln | Met | Asn | Gly | Arg | Lys | Ile | Thr | Leu | Lys | Arg | Glu | |
| | | | 3100 | | | | 3105 | | | | | 3110 | | | |
| caa | gag | agt | gag | aaa | cca | agc | caa | gaa | ctc | ttg | gaa | tat | aat | ata | 9600 |
| Gln | Glu | Ser | Glu | Lys | Pro | Ser | Gln | Glu | Leu | Leu | Glu | Tyr | Asn | Ile | |
| | | | 3115 | | | | 3120 | | | | | 3125 | | | |
| cag | cag | aag | cag | tct | caa | atg | ctg | gag | atg | caa | gtg | gag | ctc | agc | 9645 |
| Gln | Gln | Lys | Gln | Ser | Gln | Met | Leu | Glu | Met | Gln | Val | Glu | Leu | Ser | |
| | | | 3130 | | | | 3135 | | | | | 3140 | | | |
| agt | atg | aaa | gac | aga | gca | acg | gaa | ctg | cag | gag | cag | ctg | agt | tct | 9690 |
| Ser | Met | Lys | Asp | Arg | Ala | Thr | Glu | Leu | Gln | Glu | Gln | Leu | Ser | Ser | |
| | | | 3145 | | | | 3150 | | | | | 3155 | | | |
| gag | aaa | atg | gtg | gtt | gct | gaa | ctg | aag | agt | gag | ctt | gca | caa | act | 9735 |
| Glu | Lys | Met | Val | Val | Ala | Glu | Leu | Lys | Ser | Glu | Leu | Ala | Gln | Thr | |
| | | | 3160 | | | | 3165 | | | | | 3170 | | | |
| aaa | ttg | gaa | cta | gaa | aca | aca | ctc | aag | gca | cag | cat | aaa | cac | cta | 9780 |
| Lys | Leu | Glu | Leu | Glu | Thr | Thr | Leu | Lys | Ala | Gln | His | Lys | His | Leu | |
| | | | 3175 | | | | 3180 | | | | | 3185 | | | |
| aaa | gaa | ttg | gag | gct | ttc | agg | ttg | gaa | gtt | aaa | gat | aag | aca | gat | 9825 |
| Lys | Glu | Leu | Glu | Ala | Phe | Arg | Leu | Glu | Val | Lys | Asp | Lys | Thr | Asp | |
| | | | 3190 | | | | 3195 | | | | | 3200 | | | |
| gaa | gta | cat | ttg | ctt | aat | gac | aca | tta | gca | agt | gaa | cag | aaa | aaa | 9870 |
| Glu | Val | His | Leu | Leu | Asn | Asp | Thr | Leu | Ala | Ser | Glu | Gln | Lys | Lys | |
| | | | 3205 | | | | 3210 | | | | | 3215 | | | |
| tca | aga | gag | ctc | cag | tgg | gct | ttg | gag | aaa | gag | aaa | gcc | aag | ttg | 9915 |
| Ser | Arg | Glu | Leu | Gln | Trp | Ala | Leu | Glu | Lys | Glu | Lys | Ala | Lys | Leu | |
| | | | 3220 | | | | 3225 | | | | | 3230 | | | |
| gga | cgc | agt | gaa | gaa | cgg | gat | aaa | gaa | gaa | ctt | gag | gat | ctg | aag | 9960 |
| Gly | Arg | Ser | Glu | Glu | Arg | Asp | Lys | Glu | Glu | Leu | Glu | Asp | Leu | Lys | |
| | | | 3235 | | | | 3240 | | | | | 3245 | | | |
| ttt | tca | ctt | gag | agt | cag | aaa | caa | agg | aat | ctt | cag | cta | aat | cta | 10005 |
| Phe | Ser | Leu | Glu | Ser | Gln | Lys | Gln | Arg | Asn | Leu | Gln | Leu | Asn | Leu | |
| | | | 3250 | | | | 3255 | | | | | 3260 | | | |
| ctt | ttg | gaa | caa | cag | aaa | caa | cta | ctg | aac | gaa | tcc | cag | caa | aaa | 10050 |
| Leu | Leu | Glu | Gln | Gln | Lys | Gln | Leu | Leu | Asn | Glu | Ser | Gln | Gln | Lys | |

-continued

```
                  3265                      3270                      3275
         ata gaa tca cag   aga atg cta tat   gat gcc cag ttg   tca gaa gaa         10095
         Ile Glu Ser Gln   Arg Met Leu Tyr   Asp Ala Gln Leu   Ser Glu Glu
                 3280                      3285                    3290 caa ggt cga aac   tta gag ctt cag   gta ctt ctt gaa   tct gag aaa         10140
         Gln Gly Arg Asn   Leu Glu Leu Gln   Val Leu Leu Glu   Ser Glu Lys
                 3295                      3300                    3305 gtt cga att cgg   gaa atg agt agt   acc cta gat agg   gag cgg gaa         10185
         Val Arg Ile Arg   Glu Met Ser Ser   Thr Leu Asp Arg   Glu Arg Glu
                 3310                      3315                    3320 ttg cac gca cag   ctg cag agc agt   gat ggt act gga   cag tct cgg         10230
         Leu His Ala Gln   Leu Gln Ser Ser   Asp Gly Thr Gly   Gln Ser Arg
                 3325                      3330                    3335 cca ccc ttg ccc   tca gag gac cta   ctg aaa gag ctg   cag aaa cag         10275
         Pro Pro Leu Pro   Ser Glu Asp Leu   Leu Lys Glu Leu   Gln Lys Gln
                 3340                      3345                    3350 cta gag gaa aaa   cac agt cgc ata   gta gaa ttg tta   aat gag act         10320
         Leu Glu Glu Lys   His Ser Arg Ile   Val Glu Leu Leu   Asn Glu Thr
                 3355                      3360                    3365 gaa aaa tat aaa   ctg gat tct ttg   caa aca cga cag   caa atg gaa         10365
         Glu Lys Tyr Lys   Leu Asp Ser Leu   Gln Thr Arg Gln   Gln Met Glu
                 3370                      3375                    3380 aaa gat agg cag   gtt cac agg aaa   aca ctg cag aca   gaa cag gag         10410
         Lys Asp Arg Gln   Val His Arg Lys   Thr Leu Gln Thr   Glu Gln Glu
                 3385                      3390                    3395 gcc aac act gag   gga cag aaa aaa   atg cat gag ctc   cag tcc aaa         10455
         Ala Asn Thr Glu   Gly Gln Lys Lys   Met His Glu Leu   Gln Ser Lys
                 3400                      3405                    3410 gtg gaa gat ctt   cag cgc cag ctg   gaa gag aaa aga   caa caa gtt         10500
         Val Glu Asp Leu   Gln Arg Gln Leu   Glu Glu Lys Arg   Gln Gln Val
                 3415                      3420                    3425 tat aag tta gac   ctt gaa gga cag   cga cta caa gga   atc atg cag         10545
         Tyr Lys Leu Asp   Leu Glu Gly Gln   Arg Leu Gln Gly   Ile Met Gln
                 3430                      3435                    3440 gaa ttc cag aag   caa gaa cta gaa   cga gaa gaa aaa   cga gaa agt         10590
         Glu Phe Gln Lys   Gln Glu Leu Glu   Arg Glu Glu Lys   Arg Glu Ser
                 3445                      3450                    3455 aga aga att ctg   tat cag aac ctt   aat gag cca acc   acg tgg agc         10635
         Arg Arg Ile Leu   Tyr Gln Asn Leu   Asn Glu Pro Thr   Thr Trp Ser
                 3460                      3465                    3470 tta acc agt gat   aga act aga aat   tgg gtt ctt caa   cag aaa ata         10680
         Leu Thr Ser Asp   Arg Thr Arg Asn   Trp Val Leu Gln   Gln Lys Ile
                 3475                      3480                    3485 gaa gga gaa aca   aaa gaa tca aac   tac gct aaa ttg   att gaa atg         10725
         Glu Gly Glu Thr   Lys Glu Ser Asn   Tyr Ala Lys Leu   Ile Glu Met
                 3490                      3495                    3500 aat gga gga gga   acc ggc tgt aat   cat gaa tta gaa   atg atc aga         10770
         Asn Gly Gly Gly   Thr Gly Cys Asn   His Glu Leu Glu   Met Ile Arg
                 3505                      3510                    3515 caa aag ctt caa   tgt gta gct tca   aaa cta cag gtt   cta ccc cag         10815
         Gln Lys Leu Gln   Cys Val Ala Ser   Lys Leu Gln Val   Leu Pro Gln
                 3520                      3525                    3530 aaa gcc tct gag   aga cta cag ttt   gaa aca gca gat   gat gaa gat         10860
         Lys Ala Ser Glu   Arg Leu Gln Phe   Glu Thr Ala Asp   Asp Glu Asp
                 3535                      3540                    3545 ttc att tgg gtt   cag gaa aat att   gat gaa att tta   caa cta             10905
         Phe Ile Trp Val   Gln Glu Asn Ile   Asp Glu Ile Leu   Gln Leu
                 3550                      3555                    3560 cag aaa tta act   ggc cag caa ggt   gaa gag ccc agc   ttg gtg tcc         10950
```

| | | | | | | | | | | | | |
|---|---|---|---|---|---|---|---|---|---|---|---|---|
| Gln | Lys | Leu | Thr | Gly | Gln | Gln | Gly | Glu | Glu | Pro | Ser | Leu | Val | Ser |
| | | | 3565 | | | | | 3570 | | | | 3575 | | |

| cca | agt | act | tct | tgt | ggc | tca | ttg | act | gaa | aga | cta | ctg | aga | caa | 10995 |
|---|---|---|---|---|---|---|---|---|---|---|---|---|---|---|---|
| Pro | Ser | Thr | Ser | Cys | Gly | Ser | Leu | Thr | Glu | Arg | Leu | Leu | Arg | Gln | |
| | | | 3580 | | | | | 3585 | | | | 3590 | | | |

| aat | gct | gag | ctg | aca | ggg | cat | atc | agt | caa | ctg | act | gaa | gag | aag | 11040 |
|---|---|---|---|---|---|---|---|---|---|---|---|---|---|---|---|
| Asn | Ala | Glu | Leu | Thr | Gly | His | Ile | Ser | Gln | Leu | Thr | Glu | Glu | Lys | |
| | | | 3595 | | | | | 3600 | | | | 3605 | | | |

| aat | gac | tta | agg | aac | atg | gtt | atg | aag | ctg | gaa | gag | cag | atc | agg | 11085 |
|---|---|---|---|---|---|---|---|---|---|---|---|---|---|---|---|
| Asn | Asp | Leu | Arg | Asn | Met | Val | Met | Lys | Leu | Glu | Glu | Gln | Ile | Arg | |
| | | | 3610 | | | | | 3615 | | | | 3620 | | | |

| tgg | tat | cga | cag | aca | gga | gct | ggt | aga | gat | aat | tct | tcc | agg | ttt | 11130 |
|---|---|---|---|---|---|---|---|---|---|---|---|---|---|---|---|
| Trp | Tyr | Arg | Gln | Thr | Gly | Ala | Gly | Arg | Asp | Asn | Ser | Ser | Arg | Phe | |
| | | | 3625 | | | | | 3630 | | | | 3635 | | | |

| tca | ttg | aat | ggt | ggt | gcc | aac | att | gaa | gcc | atc | att | gcc | tct | gaa | 11175 |
|---|---|---|---|---|---|---|---|---|---|---|---|---|---|---|---|
| Ser | Leu | Asn | Gly | Gly | Ala | Asn | Ile | Glu | Ala | Ile | Ile | Ala | Ser | Glu | |
| | | | 3640 | | | | | 3645 | | | | 3650 | | | |

| aaa | gaa | gta | tgg | aac | aga | gaa | aaa | ttg | act | ctc | cag | aaa | tct | ttg | 11220 |
|---|---|---|---|---|---|---|---|---|---|---|---|---|---|---|---|
| Lys | Glu | Val | Trp | Asn | Arg | Glu | Lys | Leu | Thr | Leu | Gln | Lys | Ser | Leu | |
| | | | 3655 | | | | | 3660 | | | | 3665 | | | |

| aaa | agg | gca | gag | gct | gaa | gta | tac | aaa | ctg | aaa | gct | gaa | cta | aga | 11265 |
|---|---|---|---|---|---|---|---|---|---|---|---|---|---|---|---|
| Lys | Arg | Ala | Glu | Ala | Glu | Val | Tyr | Lys | Leu | Lys | Ala | Glu | Leu | Arg | |
| | | | 3670 | | | | | 3675 | | | | 3680 | | | |

| aat | gac | tct | tta | ctt | caa | act | ctg | agc | cct | gat | tct | gaa | cat | gtc | 11310 |
|---|---|---|---|---|---|---|---|---|---|---|---|---|---|---|---|
| Asn | Asp | Ser | Leu | Leu | Gln | Thr | Leu | Ser | Pro | Asp | Ser | Glu | His | Val | |
| | | | 3685 | | | | | 3690 | | | | 3695 | | | |

| act | tta | aag | aga | att | tat | ggt | aaa | tac | ttg | agg | gca | gaa | agt | ttt | 11355 |
|---|---|---|---|---|---|---|---|---|---|---|---|---|---|---|---|
| Thr | Leu | Lys | Arg | Ile | Tyr | Gly | Lys | Tyr | Leu | Arg | Ala | Glu | Ser | Phe | |
| | | | 3700 | | | | | 3705 | | | | 3710 | | | |

| cga | aag | gct | ctc | att | tac | cag | aag | aaa | tac | ctg | ctg | ctg | tta | ctg | 11400 |
|---|---|---|---|---|---|---|---|---|---|---|---|---|---|---|---|
| Arg | Lys | Ala | Leu | Ile | Tyr | Gln | Lys | Lys | Tyr | Leu | Leu | Leu | Leu | Leu | |
| | | | 3715 | | | | | 3720 | | | | 3725 | | | |

| ggt | ggg | ttc | cag | gaa | tgt | gaa | gat | gcc | acc | ttg | gcc | ctg | ctt | gcc | 11445 |
|---|---|---|---|---|---|---|---|---|---|---|---|---|---|---|---|
| Gly | Gly | Phe | Gln | Glu | Cys | Glu | Asp | Ala | Thr | Leu | Ala | Leu | Leu | Ala | |
| | | | 3730 | | | | | 3735 | | | | 3740 | | | |

| cgg | atg | ggg | ggg | cag | cca | gct | ttc | acg | gat | cta | gag | gtg | atc | acc | 11490 |
|---|---|---|---|---|---|---|---|---|---|---|---|---|---|---|---|
| Arg | Met | Gly | Gly | Gln | Pro | Ala | Phe | Thr | Asp | Leu | Glu | Val | Ile | Thr | |
| | | | 3745 | | | | | 3750 | | | | 3755 | | | |

| aat | cgc | cca | aag | ggc | ttc | acc | agg | ttt | cgg | tcg | gcc | gtc | aga | gta | 11535 |
|---|---|---|---|---|---|---|---|---|---|---|---|---|---|---|---|
| Asn | Arg | Pro | Lys | Gly | Phe | Thr | Arg | Phe | Arg | Ser | Ala | Val | Arg | Val | |
| | | | 3760 | | | | | 3765 | | | | 3770 | | | |

| tcc | att | gca | att | tcc | aga | atg | aaa | ttt | ttg | gtt | cga | cgg | tgg | cat | 11580 |
|---|---|---|---|---|---|---|---|---|---|---|---|---|---|---|---|
| Ser | Ile | Ala | Ile | Ser | Arg | Met | Lys | Phe | Leu | Val | Arg | Arg | Trp | His | |
| | | | 3775 | | | | | 3780 | | | | 3785 | | | |

| cga | gtc | aca | ggt | tct | gtt | tcc | atc | aat | att | aac | aga | gat | ggc | ttt | 11625 |
|---|---|---|---|---|---|---|---|---|---|---|---|---|---|---|---|
| Arg | Val | Thr | Gly | Ser | Val | Ser | Ile | Asn | Ile | Asn | Arg | Asp | Gly | Phe | |
| | | | 3790 | | | | | 3795 | | | | 3800 | | | |

| gga | ctg | aat | caa | ggt | gca | gaa | aag | act | gac | tca | ttt | tat | cat | tct | 11670 |
|---|---|---|---|---|---|---|---|---|---|---|---|---|---|---|---|
| Gly | Leu | Asn | Gln | Gly | Ala | Glu | Lys | Thr | Asp | Ser | Phe | Tyr | His | Ser | |
| | | | 3805 | | | | | 3810 | | | | 3815 | | | |

| tct | ggt | ggg | ctg | gag | tta | tat | gga | gaa | cca | aga | cat | act | acg | tat | 11715 |
|---|---|---|---|---|---|---|---|---|---|---|---|---|---|---|---|
| Ser | Gly | Gly | Leu | Glu | Leu | Tyr | Gly | Glu | Pro | Arg | His | Thr | Thr | Tyr | |
| | | | 3820 | | | | | 3825 | | | | 3830 | | | |

| cgc | tca | aga | tca | gat | ctg | gac | tat | att | agg | tcc | cct | tta | cca | ttt | 11760 |
|---|---|---|---|---|---|---|---|---|---|---|---|---|---|---|---|
| Arg | Ser | Arg | Ser | Asp | Leu | Asp | Tyr | Ile | Arg | Ser | Pro | Leu | Pro | Phe | |
| | | | 3835 | | | | | 3840 | | | | 3845 | | | |

| cag | aat | agg | tac | cca | ggc | act | cca | gct | gat | ttc | aat | cct | ggt | tct | 11805 |
|---|---|---|---|---|---|---|---|---|---|---|---|---|---|---|---|
| Gln | Asn | Arg | Tyr | Pro | Gly | Thr | Pro | Ala | Asp | Phe | Asn | Pro | Gly | Ser | |
| | | | 3850 | | | | | 3855 | | | | 3860 | | | |

-continued

```
tta gca tgt tct cag ctt cag aat tac gat cct gac aga gcc cta        11850
Leu Ala Cys Ser Gln Leu Gln Asn Tyr Asp Pro Asp Arg Ala Leu
            3865                3870                3875 aca gat tat atc act cgg cta gag gca ctg caa aga cga ctt gga        11895
Thr Asp Tyr Ile Thr Arg Leu Glu Ala Leu Gln Arg Arg Leu Gly
            3880                3885                3890 act ata cag tca ggt tca act act caa ttt cat gct ggc atg aga        11940
Thr Ile Gln Ser Gly Ser Thr Thr Gln Phe His Ala Gly Met Arg
            3895                3900                3905 aga taa tcctttgaaa catcattaat tgaagtgatt ttaaatagat ttccttttgt     11996
Arg aaatcaatgg ttcttttgtg cttttgtatt gtgaatattc aatgggacca atatgaacac  12056
agcttatgat tgtatacaaa tcccttgcca gcacatgaaa acaaactgga atttgtatat  12116
ataagcattg tgtatgtatt catgcacaat aattattgaa ttacctgtat atttgtggaa  12176
tgctaattta aaacattaaa ttataaacct tgtgtattta tcaaatgggt gaaaagatta  12236 aactttacg cattacaata ctgctgaatg tgtagctcga ggtgtcctgc acttttctta   12296
taaggctact gaagttacat gttttgccta atatattcta ctggtgatga agacagataa  12356
tatcacttgt agagacctat ttttgtataa tggtagaagt tttgaatttt atggggtatt  12416
ttgtcaagta ctgaaataaa aatgacttca ccattttcac cacact             12462
```

```
<210> SEQ ID NO 2
<211> LENGTH: 3907
<212> TYPE: PRT
<213> ORGANISM: Homo sapiens
<220> FEATURE:
<221> NAME/KEY: misc_feature
<222> LOCATION: (2484)..(2484)
<223> OTHER INFORMATION: The 'Xaa' at location 2484 stands for Arg, or
      Lys.

<400> SEQUENCE: 2
```

```
Met Glu Asp Glu Glu Arg Gln Lys Lys Leu Glu Ala Gly Lys Ala Lys
1               5                   10                  15

Leu Ala Gln Phe Arg Gln Arg Lys Ala Gln Ser Asp Gly Gln Ser Pro
            20                  25                  30

Ser Lys Lys Gln Lys Lys Arg Lys Thr Ser Ser Ser Lys His Asp
        35                  40                  45

Val Ser Ala His His Asp Leu Asn Ile Asp Gln Ser Gln Cys Asn Glu
    50                  55                  60

Met Tyr Ile Asn Ser Ser Gln Arg Val Glu Ser Thr Val Ile Pro Glu
65                  70                  75                  80

Ser Thr Ile Met Arg Thr Leu His Ser Gly Glu Ile Thr Ser His Glu
                85                  90                  95

Gln Gly Phe Ser Val Glu Leu Glu Ser Glu Ile Ser Thr Thr Ala Asp
            100                 105                 110

Asp Cys Ser Ser Glu Val Asn Gly Cys Ser Phe Val Met Arg Thr Gly
        115                 120                 125

Lys Pro Thr Asn Leu Leu Arg Glu Glu Glu Phe Gly Val Asp Asp Ser
    130                 135                 140

Tyr Ser Glu Gln Gly Ala Gln Asp Ser Pro Thr His Leu Glu Met Met
145                 150                 155                 160

Glu Ser Glu Leu Ala Gly Lys Gln His Glu Ile Glu Glu Leu Asn Arg
                165                 170                 175

Glu Leu Glu Glu Met Arg Val Thr Tyr Gly Thr Glu Gly Leu Gln Gln
            180                 185                 190
```

-continued

```
Leu Gln Glu Phe Glu Ala Ala Ile Lys Gln Arg Asp Gly Ile Ile Thr
            195                 200                 205
Gln Leu Thr Ala Asn Leu Gln Gln Ala Arg Arg Glu Lys Asp Glu Thr
        210                 215                 220
Met Arg Glu Phe Leu Glu Leu Thr Glu Gln Ser Gln Lys Leu Gln Ile
225                 230                 235                 240
Gln Phe Gln Gln Leu Gln Ala Ser Glu Thr Leu Arg Asn Ser Thr His
            245                 250                 255
Ser Ser Thr Ala Ala Asp Leu Leu Gln Ala Lys Gln Gln Ile Leu Thr
        260                 265                 270
His Gln Gln Gln Leu Glu Glu Gln Asp His Leu Leu Glu Asp Tyr Gln
    275                 280                 285
Lys Lys Lys Glu Asp Phe Thr Met Gln Ile Ser Phe Leu Gln Glu Lys
        290                 295                 300
Ile Lys Val Tyr Glu Met Glu Gln Asp Lys Val Glu Asn Ser Asn
305                 310                 315                 320
Lys Glu Glu Ile Gln Glu Lys Glu Thr Ile Ile Glu Glu Leu Asn Thr
            325                 330                 335
Lys Ile Ile Glu Glu Lys Lys Thr Leu Glu Leu Lys Asp Lys Leu
        340                 345                 350
Thr Thr Ala Asp Lys Leu Leu Gly Glu Leu Gln Glu Gln Ile Val Gln
    355                 360                 365
Lys Asn Gln Glu Ile Lys Asn Met Lys Leu Glu Leu Thr Asn Ser Lys
        370                 375                 380
Gln Lys Glu Arg Gln Ser Ser Glu Glu Ile Lys Gln Leu Met Gly Thr
385                 390                 395                 400
Val Glu Glu Leu Gln Lys Arg Asn His Lys Asp Ser Gln Phe Glu Thr
            405                 410                 415
Asp Ile Val Gln Arg Met Glu Gln Glu Thr Gln Arg Lys Leu Glu Gln
        420                 425                 430
Leu Arg Ala Glu Leu Asp Glu Met Tyr Gly Gln Gln Ile Val Gln Met
    435                 440                 445
Lys Gln Glu Leu Ile Arg Gln His Met Ala Gln Met Glu Glu Met Lys
        450                 455                 460
Thr Arg His Lys Gly Glu Met Glu Asn Ala Leu Arg Ser Tyr Ser Asn
465                 470                 475                 480
Ile Thr Val Asn Glu Asp Gln Ile Lys Leu Met Asn Val Ala Ile Asn
            485                 490                 495
Glu Leu Asn Ile Lys Leu Gln Asp Thr Asn Ser Gln Lys Glu Lys Leu
        500                 505                 510
Lys Glu Glu Leu Gly Leu Ile Leu Glu Glu Lys Cys Ala Leu Gln Arg
    515                 520                 525
Gln Leu Glu Asp Leu Val Glu Glu Leu Ser Phe Ser Arg Glu Gln Ile
        530                 535                 540
Gln Arg Ala Arg Gln Thr Ile Ala Glu Gln Glu Ser Lys Leu Asn Glu
545                 550                 555                 560
Ala His Lys Ser Leu Ser Thr Val Glu Asp Leu Lys Ala Glu Ile Val
            565                 570                 575
Ser Ala Ser Glu Ser Arg Lys Glu Leu Glu Leu Lys His Glu Ala Glu
        580                 585                 590
Val Thr Asn Tyr Lys Ile Lys Leu Glu Met Leu Glu Lys Glu Lys Asn
    595                 600                 605
```

-continued

Ala Val Leu Asp Arg Met Ala Glu Ser Gln Glu Ala Glu Leu Glu Arg
        610                 615                 620
Leu Arg Thr Gln Leu Leu Phe Ser His Glu Glu Leu Ser Lys Leu
625                 630                 635                 640
Lys Glu Asp Leu Glu Ile Glu His Arg Ile Asn Ile Glu Lys Leu Lys
                645                 650                 655
Asp Asn Leu Gly Ile His Tyr Lys Gln Gln Ile Asp Gly Leu Gln Asn
            660                 665                 670
Glu Met Ser Gln Lys Ile Glu Thr Met Gln Phe Glu Lys Asp Asn Leu
        675                 680                 685
Ile Thr Lys Gln Asn Gln Leu Ile Leu Glu Ile Ser Lys Leu Lys Asp
    690                 695                 700
Leu Gln Gln Ser Leu Val Asn Ser Lys Ser Glu Glu Met Thr Leu Gln
705                 710                 715                 720
Ile Asn Glu Leu Gln Lys Glu Ile Glu Ile Leu Arg Gln Glu Lys
                725                 730                 735
Glu Lys Gly Thr Leu Glu Gln Glu Val Gln Glu Leu Gln Leu Lys Thr
            740                 745                 750
Glu Leu Leu Glu Lys Gln Met Lys Glu Lys Glu Asn Asp Leu Gln Glu
        755                 760                 765
Lys Phe Ala Gln Leu Glu Ala Glu Asn Ser Ile Leu Lys Asp Glu Lys
    770                 775                 780
Lys Thr Leu Glu Asp Met Leu Lys Ile His Thr Pro Val Ser Gln Glu
785                 790                 795                 800
Glu Arg Leu Ile Phe Leu Asp Ser Ile Lys Ser Lys Ser Lys Asp Ser
                805                 810                 815
Val Trp Glu Lys Glu Ile Glu Ile Leu Ile Glu Glu Asn Glu Asp Leu
            820                 825                 830
Lys Gln Gln Cys Ile Gln Leu Asn Glu Glu Ile Glu Lys Gln Arg Asn
        835                 840                 845
Thr Phe Ser Phe Ala Glu Lys Asn Phe Glu Val Asn Tyr Gln Glu Leu
    850                 855                 860
Gln Glu Glu Tyr Ala Cys Leu Leu Lys Val Lys Asp Asp Leu Glu Asp
865                 870                 875                 880
Ser Lys Asn Lys Gln Glu Leu Glu Tyr Lys Ser Lys Leu Lys Ala Leu
                885                 890                 895
Asn Glu Glu Leu His Leu Gln Arg Ile Asn Pro Thr Thr Val Lys Met
            900                 905                 910
Lys Ser Ser Val Phe Asp Glu Asp Lys Thr Phe Val Ala Glu Thr Leu
        915                 920                 925
Glu Met Gly Glu Val Val Glu Lys Asp Thr Thr Glu Leu Met Glu Lys
    930                 935                 940
Leu Glu Val Thr Lys Arg Glu Lys Leu Glu Leu Ser Gln Arg Leu Ser
945                 950                 955                 960
Asp Leu Ser Glu Gln Leu Lys Gln Lys His Gly Glu Ile Ser Phe Leu
                965                 970                 975
Asn Glu Glu Val Lys Ser Leu Lys Gln Lys Glu Gln Val Ser Leu
            980                 985                 990
Arg Cys Arg Glu Leu Glu Ile Ile Ile Asn His Asn Arg Ala Glu Asn
        995                 1000                1005
Val Gln Ser Cys Asp Thr Gln Val Ser Ser Leu Leu Asp Gly Val
    1010                1015                1020
Val Thr Met Thr Ser Arg Gly Ala Glu Gly Ser Val Ser Lys Val

-continued

```
                1025                1030                1035
Asn Lys Ser Phe Gly Glu Glu Ser Lys Ile Met Val Glu Asp Lys
        1040                1045                1050

Val Ser Phe Glu Asn Met Thr Val Gly Glu Glu Ser Lys Gln Glu
        1055                1060                1065

Gln Leu Ile Leu Asp His Leu Pro Ser Val Thr Lys Glu Ser Ser
        1070                1075                1080

Leu Arg Ala Thr Gln Pro Ser Glu Asn Asp Lys Leu Gln Lys Glu
        1085                1090                1095

Leu Asn Val Leu Lys Ser Glu Gln Asn Asp Leu Arg Leu Gln Met
        1100                1105                1110

Glu Ala Gln Arg Ile Cys Leu Ser Leu Val Tyr Ser Thr His Val
        1115                1120                1125

Asp Gln Val Arg Glu Tyr Met Glu Asn Glu Lys Asp Lys Ala Leu
        1130                1135                1140

Cys Ser Leu Lys Glu Glu Leu Ile Phe Ala Gln Glu Glu Lys Ile
        1145                1150                1155

Lys Glu Leu Gln Lys Ile His Gln Leu Glu Leu Gln Thr Met Lys
        1160                1165                1170

Thr Gln Glu Thr Gly Asp Glu Gly Lys Pro Leu His Leu Leu Ile
        1175                1180                1185

Gly Lys Leu Gln Lys Ala Val Ser Glu Cys Ser Tyr Phe Leu
        1190                1195                1200

Gln Thr Leu Cys Ser Val Leu Gly Glu Tyr Tyr Thr Pro Ala Leu
        1205                1210                1215

Lys Cys Glu Val Asn Ala Glu Asp Lys Glu Asn Ser Gly Asp Tyr
        1220                1225                1230

Ile Ser Glu Asn Glu Asp Pro Glu Leu Gln Asp Tyr Arg Tyr Glu
        1235                1240                1245

Val Gln Asp Phe Gln Glu Asn Met His Thr Leu Leu Asn Lys Val
        1250                1255                1260

Thr Glu Glu Tyr Asn Lys Leu Leu Val Leu Gln Thr Arg Leu Ser
        1265                1270                1275

Lys Ile Trp Gly Gln Gln Thr Asp Gly Met Lys Leu Glu Phe Gly
        1280                1285                1290

Glu Glu Asn Leu Pro Lys Glu Glu Thr Glu Phe Leu Ser Ile His
        1295                1300                1305

Ser Gln Met Thr Asn Leu Glu Asp Ile Asp Val Asn His Lys Ser
        1310                1315                1320

Lys Leu Ser Ser Leu Gln Asp Leu Glu Lys Thr Lys Leu Glu Glu
        1325                1330                1335

Gln Val Gln Glu Leu Glu Ser Leu Ile Ser Ser Leu Gln Gln Gln
        1340                1345                1350

Leu Lys Glu Thr Glu Gln Asn Tyr Glu Ala Glu Ile His Cys Leu
        1355                1360                1365

Gln Lys Arg Leu Gln Ala Val Ser Glu Ser Thr Val Pro Pro Ser
        1370                1375                1380

Leu Pro Val Asp Ser Val Val Ile Thr Glu Ser Asp Ala Gln Arg
        1385                1390                1395

Thr Met Tyr Pro Gly Ser Cys Val Lys Lys Asn Ile Asp Gly Thr
        1400                1405                1410

Ile Glu Phe Ser Gly Glu Phe Gly Val Lys Glu Glu Thr Asn Ile
        1415                1420                1425
```

-continued

```
Val Lys Leu Leu Glu Lys Gln Tyr Gln Glu Gln Leu Glu Glu Glu
    1430            1435                1440
Val Ala Lys Val Ile Val Ser Met Ser Ile Ala Phe Ala Gln Gln
    1445            1450                1455
Thr Glu Leu Ser Arg Ile Ser Gly Gly Lys Glu Asn Thr Ala Ser
    1460            1465                1470
Ser Lys Gln Ala His Ala Val Cys Gln Gln Glu Gln His Tyr Phe
    1475            1480                1485
Asn Glu Met Lys Leu Ser Gln Asp Gln Ile Gly Phe Gln Thr Phe
    1490            1495                1500
Glu Thr Val Asp Val Lys Phe Lys Glu Glu Phe Lys Pro Leu Ser
    1505            1510                1515
Lys Glu Leu Gly Glu His Gly Lys Glu Ile Leu Leu Ser Asn Ser
    1520            1525                1530
Asp Pro His Asp Ile Pro Glu Ser Lys Asp Cys Val Leu Thr Ile
    1535            1540                1545
Ser Glu Glu Met Phe Ser Lys Asp Lys Thr Phe Ile Val Arg Gln
    1550            1555                1560
Ser Ile His Asp Glu Ile Ser Val Ser Ser Met Asp Ala Ser Arg
    1565            1570                1575
Gln Leu Met Leu Asn Glu Glu Gln Leu Glu Asp Met Arg Gln Glu
    1580            1585                1590
Leu Val Arg Gln Tyr Gln Glu His Gln Gln Ala Thr Glu Leu Leu
    1595            1600                1605
Arg Gln Ala His Met Arg Gln Met Glu Arg Gln Arg Glu Asp Gln
    1610            1615                1620
Glu Gln Leu Gln Glu Glu Ile Lys Arg Leu Asn Arg Gln Leu Ala
    1625            1630                1635
Gln Arg Ser Ser Ile Asp Asn Glu Asn Leu Val Ser Glu Arg Glu
    1640            1645                1650
Arg Val Leu Leu Glu Glu Leu Glu Ala Leu Lys Gln Leu Ser Leu
    1655            1660                1665
Ala Gly Arg Glu Lys Leu Cys Cys Glu Leu Arg Asn Ser Ser Thr
    1670            1675                1680
Gln Thr Gln Asn Gly Asn Glu Asn Gln Gly Glu Val Glu Glu Gln
    1685            1690                1695
Thr Phe Lys Glu Lys Glu Leu Asp Arg Lys Pro Glu Asp Val Pro
    1700            1705                1710
Pro Glu Ile Leu Ser Asn Glu Arg Tyr Ala Leu Gln Lys Ala Asn
    1715            1720                1725
Asn Arg Leu Leu Lys Ile Leu Leu Glu Val Val Lys Thr Thr Ala
    1730            1735                1740
Ala Val Glu Glu Thr Ile Gly Arg His Val Leu Gly Ile Leu Asp
    1745            1750                1755
Arg Ser Ser Lys Ser Gln Ser Ser Ala Ser Leu Ile Trp Arg Ser
    1760            1765                1770
Glu Ala Glu Ala Ser Val Lys Ser Cys Val His Glu Glu His Thr
    1775            1780                1785
Arg Val Thr Asp Glu Ser Ile Pro Ser Tyr Ser Gly Ser Asp Met
    1790            1795                1800
Pro Arg Asn Asp Ile Asn Met Trp Ser Lys Val Thr Glu Glu Gly
    1805            1810                1815
```

-continued

```
Thr Glu Leu Ser Gln Arg Leu Val Arg Ser Gly Phe Ala Gly Thr
    1820                1825                1830

Glu Ile Asp Pro Glu Asn Glu Leu Met Leu Asn Ile Ser Ser
    1835                1840                1845

Arg Leu Gln Ala Ala Val Glu Lys Leu Leu Glu Ala Ile Ser Glu
    1850                1855                1860

Thr Ser Ser Gln Leu Glu His Ala Lys Val Thr Gln Thr Glu Leu
    1865                1870                1875

Met Arg Glu Ser Phe Arg Gln Lys Gln Glu Ala Thr Glu Ser Leu
    1880                1885                1890

Lys Cys Gln Glu Glu Leu Arg Glu Arg Leu His Glu Glu Ser Arg
    1895                1900                1905

Ala Arg Glu Gln Leu Ala Val Glu Leu Ser Lys Ala Glu Gly Val
    1910                1915                1920

Ile Asp Gly Tyr Ala Asp Glu Lys Thr Leu Phe Glu Arg Gln Ile
    1925                1930                1935

Gln Glu Lys Thr Asp Ile Ile Asp Arg Leu Glu Gln Glu Leu Leu
    1940                1945                1950

Cys Ala Ser Asn Arg Leu Gln Glu Leu Glu Ala Glu Gln Gln Gln
    1955                1960                1965

Ile Gln Glu Glu Arg Glu Leu Leu Ser Arg Gln Lys Glu Ala Met
    1970                1975                1980

Lys Ala Glu Ala Gly Pro Val Glu Gln Gln Leu Leu Gln Glu Thr
    1985                1990                1995

Glu Lys Leu Met Lys Glu Lys Leu Glu Val Gln Cys Gln Ala Glu
    2000                2005                2010

Lys Val Arg Asp Asp Leu Gln Lys Gln Val Lys Ala Leu Glu Ile
    2015                2020                2025

Asp Val Glu Glu Gln Val Ser Arg Phe Ile Glu Leu Glu Gln Glu
    2030                2035                2040

Lys Asn Thr Glu Leu Met Asp Leu Arg Gln Gln Asn Gln Ala Leu
    2045                2050                2055

Glu Lys Gln Leu Glu Lys Met Arg Lys Phe Leu Asp Glu Gln Ala
    2060                2065                2070

Ile Asp Arg Glu His Glu Arg Asp Val Phe Gln Gln Glu Ile Gln
    2075                2080                2085

Lys Leu Glu Gln Gln Leu Lys Val Val Pro Arg Phe Gln Pro Ile
    2090                2095                2100

Ser Glu His Gln Thr Arg Glu Val Glu Gln Leu Ala Asn His Leu
    2105                2110                2115

Lys Glu Lys Thr Asp Lys Cys Ser Glu Leu Leu Leu Ser Lys Glu
    2120                2125                2130

Gln Leu Gln Arg Asp Ile Gln Glu Arg Asn Glu Glu Ile Glu Lys
    2135                2140                2145

Leu Glu Phe Arg Val Arg Glu Leu Glu Gln Ala Leu Leu Val Ser
    2150                2155                2160

Ala Asp Thr Phe Gln Lys Val Glu Asp Arg Lys His Phe Gly Ala
    2165                2170                2175

Val Glu Ala Lys Pro Glu Leu Ser Leu Glu Val Gln Leu Gln Ala
    2180                2185                2190

Glu Arg Asp Ala Ile Asp Arg Lys Glu Lys Glu Ile Thr Asn Leu
    2195                2200                2205

Glu Glu Gln Leu Glu Gln Phe Arg Glu Glu Leu Glu Asn Lys Asn
```

-continued

```
                2210                2215                2220
Glu Glu Val Gln Gln Leu His Met Gln Leu Glu Ile Gln Lys Lys
2225                2230                2235
Glu Ser Thr Thr Arg Leu Gln Glu Leu Glu Gln Glu Asn Lys Leu
2240                2245                2250
Phe Lys Asp Asp Met Glu Lys Leu Gly Leu Ala Ile Lys Glu Ser
2255                2260                2265
Asp Ala Met Ser Thr Gln Asp Gln His Val Leu Phe Gly Lys Phe
2270                2275                2280
Ala Gln Ile Ile Gln Glu Lys Glu Val Glu Ile Asp Gln Leu Asn
2285                2290                2295
Glu Gln Val Thr Lys Leu Gln Gln Gln Leu Lys Ile Thr Thr Asp
2300                2305                2310
Asn Lys Val Ile Glu Glu Lys Asn Glu Leu Ile Arg Asp Leu Glu
2315                2320                2325
Thr Gln Ile Glu Cys Leu Met Ser Asp Gln Glu Cys Val Lys Arg
2330                2335                2340
Asn Arg Glu Glu Glu Ile Glu Gln Leu Asn Glu Val Ile Glu Lys
2345                2350                2355
Leu Gln Gln Glu Leu Ala Asn Ile Gly Gln Lys Thr Ser Met Asn
2360                2365                2370
Ala His Ser Leu Ser Glu Glu Ala Asp Ser Leu Lys His Gln Leu
2375                2380                2385
Asp Val Val Ile Ala Glu Lys Leu Ala Leu Glu Gln Gln Val Glu
2390                2395                2400
Thr Ala Asn Glu Glu Met Thr Phe Met Lys Asn Val Leu Lys Glu
2405                2410                2415
Thr Asn Phe Lys Met Asn Gln Leu Thr Gln Glu Leu Phe Ser Leu
2420                2425                2430
Lys Arg Glu Arg Glu Ser Val Glu Lys Ile Gln Ser Ile Pro Glu
2435                2440                2445
Asn Ser Val Asn Val Ala Ile Asp His Leu Ser Lys Asp Lys Pro
2450                2455                2460
Glu Leu Glu Val Val Leu Thr Glu Asp Ala Leu Lys Ser Leu Glu
2465                2470                2475
Asn Gln Thr Tyr Phe Xaa Ser Phe Glu Glu Asn Gly Lys Gly Ser
2480                2485                2490
Ile Ile Asn Leu Glu Thr Arg Leu Leu Gln Leu Glu Ser Thr Val
2495                2500                2505
Ser Ala Lys Asp Leu Glu Leu Thr Gln Cys Tyr Lys Gln Ile Lys
2510                2515                2520
Asp Met Gln Glu Gln Gly Gln Phe Glu Thr Glu Met Leu Gln Lys
2525                2530                2535
Lys Ile Val Asn Leu Gln Lys Ile Val Glu Glu Lys Val Ala Ala
2540                2545                2550
Ala Leu Val Ser Gln Ile Gln Leu Glu Ala Val Gln Glu Tyr Ala
2555                2560                2565
Lys Phe Cys Gln Asp Asn Gln Thr Ile Ser Ser Glu Pro Glu Arg
2570                2575                2580
Thr Asn Ile Gln Asn Leu Asn Gln Leu Arg Glu Asp Glu Leu Gly
2585                2590                2595
Ser Asp Ile Ser Ala Leu Thr Leu Arg Ile Ser Glu Leu Glu Ser
2600                2605                2610
```

-continued

```
Gln Val Val Glu Met His Thr Ser Leu Ile Leu Glu Lys Glu Gln
2615                 2620                 2625

Val Glu Ile Ala Glu Lys Asn Val Leu Glu Lys Glu Lys Lys Leu
2630                 2635                 2640

Leu Glu Leu Gln Lys Leu Leu Glu Gly Asn Glu Lys Lys Gln Arg
2645                 2650                 2655

Glu Lys Glu Lys Lys Arg Ser Pro Gln Asp Val Glu Val Leu Lys
2660                 2665                 2670

Thr Thr Thr Glu Leu Phe His Ser Asn Glu Glu Ser Gly Phe Phe
2675                 2680                 2685

Asn Glu Leu Glu Ala Leu Arg Ala Glu Ser Val Ala Thr Lys Ala
2690                 2695                 2700

Glu Leu Ala Ser Tyr Lys Glu Lys Ala Glu Lys Leu Gln Glu Glu
2705                 2710                 2715

Leu Leu Val Lys Glu Thr Asn Met Thr Ser Leu Gln Lys Asp Leu
2720                 2725                 2730

Ser Gln Val Arg Asp His Leu Ala Glu Ala Lys Glu Lys Leu Ser
2735                 2740                 2745

Ile Leu Glu Lys Glu Asp Glu Thr Glu Val Gln Glu Ser Lys Lys
2750                 2755                 2760

Ala Cys Met Phe Glu Pro Leu Pro Ile Lys Leu Ser Lys Ser Ile
2765                 2770                 2775

Ala Ser Gln Thr Asp Gly Thr Leu Lys Ile Ser Ser Ser Asn Gln
2780                 2785                 2790

Thr Pro Gln Ile Leu Val Lys Asn Ala Gly Ile Gln Ile Asn Leu
2795                 2800                 2805

Gln Ser Glu Cys Ser Ser Glu Glu Val Thr Glu Ile Ile Ser Gln
2810                 2815                 2820

Phe Thr Glu Lys Ile Glu Lys Met Gln Glu Leu His Ala Ala Glu
2825                 2830                 2835

Ile Leu Asp Met Glu Ser Arg His Ile Ser Glu Thr Glu Thr Leu
2840                 2845                 2850

Lys Arg Glu His Tyr Val Ala Val Gln Leu Leu Lys Glu Glu Cys
2855                 2860                 2865

Gly Thr Leu Lys Ala Val Ile Gln Cys Leu Arg Ser Lys Glu Gly
2870                 2875                 2880

Ser Ser Ile Pro Glu Leu Ala His Ser Asp Ala Tyr Gln Thr Arg
2885                 2890                 2895

Glu Ile Cys Ser Ser Asp Ser Gly Ser Asp Trp Gly Gln Gly Ile
2900                 2905                 2910

Tyr Leu Thr His Ser Gln Gly Phe Asp Ile Ala Ser Glu Gly Arg
2915                 2920                 2925

Gly Glu Glu Ser Glu Ser Ala Thr Asp Ser Phe Pro Lys Lys Ile
2930                 2935                 2940

Lys Gly Leu Leu Arg Ala Val His Asn Glu Gly Met Gln Val Leu
2945                 2950                 2955

Ser Leu Thr Glu Ser Pro Tyr Ser Asp Gly Glu Asp His Ser Ile
2960                 2965                 2970

Gln Gln Val Ser Glu Pro Trp Leu Glu Glu Arg Lys Ala Tyr Ile
2975                 2980                 2985

Asn Thr Ile Ser Ser Leu Lys Asp Leu Ile Thr Lys Met Gln Leu
2990                 2995                 3000
```

-continued

```
Gln Arg Glu Ala Glu Val Tyr Asp Ser Ser Gln Ser His Glu Ser
    3005                3010                3015

Phe Ser Asp Trp Arg Gly Glu Leu Leu Leu Ala Leu Gln Gln Val
    3020                3025                3030

Phe Leu Glu Glu Arg Ser Val Leu Leu Ala Ala Phe Arg Thr Glu
    3035                3040                3045

Leu Thr Ala Leu Gly Thr Thr Asp Ala Val Gly Leu Leu Asn Cys
    3050                3055                3060

Leu Glu Gln Arg Ile Gln Glu Gln Gly Val Glu Tyr Gln Ala Ala
    3065                3070                3075

Met Glu Cys Leu Gln Lys Ala Asp Arg Arg Ser Leu Leu Ser Glu
    3080                3085                3090

Ile Gln Ala Leu His Ala Gln Met Asn Gly Arg Lys Ile Thr Leu
    3095                3100                3105

Lys Arg Glu Gln Glu Ser Glu Lys Pro Ser Gln Glu Leu Leu Glu
    3110                3115                3120

Tyr Asn Ile Gln Gln Lys Gln Ser Gln Met Leu Glu Met Gln Val
    3125                3130                3135

Glu Leu Ser Ser Met Lys Asp Arg Ala Thr Glu Leu Gln Glu Gln
    3140                3145                3150

Leu Ser Ser Glu Lys Met Val Val Ala Glu Leu Lys Ser Glu Leu
    3155                3160                3165

Ala Gln Thr Lys Leu Glu Leu Glu Thr Thr Leu Lys Ala Gln His
    3170                3175                3180

Lys His Leu Lys Glu Leu Glu Ala Phe Arg Leu Glu Val Lys Asp
    3185                3190                3195

Lys Thr Asp Glu Val His Leu Leu Asn Asp Thr Leu Ala Ser Glu
    3200                3205                3210

Gln Lys Lys Ser Arg Glu Leu Gln Trp Ala Leu Glu Lys Glu Lys
    3215                3220                3225

Ala Lys Leu Gly Arg Ser Glu Glu Arg Asp Lys Glu Glu Leu Glu
    3230                3235                3240

Asp Leu Lys Phe Ser Leu Glu Ser Gln Lys Gln Arg Asn Leu Gln
    3245                3250                3255

Leu Asn Leu Leu Leu Glu Gln Gln Lys Gln Leu Leu Asn Glu Ser
    3260                3265                3270

Gln Gln Lys Ile Glu Ser Gln Arg Met Leu Tyr Asp Ala Gln Leu
    3275                3280                3285

Ser Glu Glu Gln Gly Arg Asn Leu Glu Leu Gln Val Leu Leu Glu
    3290                3295                3300

Ser Glu Lys Val Arg Ile Arg Glu Met Ser Ser Thr Leu Asp Arg
    3305                3310                3315

Glu Arg Glu Leu His Ala Gln Leu Gln Ser Ser Asp Gly Thr Gly
    3320                3325                3330

Gln Ser Arg Pro Pro Leu Pro Ser Glu Asp Leu Leu Lys Glu Leu
    3335                3340                3345

Gln Lys Gln Leu Glu Glu Lys His Ser Arg Ile Val Glu Leu Leu
    3350                3355                3360

Asn Glu Thr Glu Lys Tyr Lys Leu Asp Ser Leu Gln Thr Arg Gln
    3365                3370                3375

Gln Met Glu Lys Asp Arg Gln Val His Arg Lys Thr Leu Gln Thr
    3380                3385                3390

Glu Gln Glu Ala Asn Thr Glu Gly Gln Lys Lys Met His Glu Leu
```

-continued

```
            3395                3400                3405
Gln Ser Lys Val Glu Asp Leu Gln Arg Gln Leu Glu Glu Lys Arg
            3410                3415                3420
Gln Gln Val Tyr Lys Leu Asp Leu Glu Gly Gln Arg Leu Gln Gly
            3425                3430                3435
Ile Met Gln Glu Phe Gln Lys Gln Glu Leu Glu Arg Glu Glu Lys
            3440                3445                3450
Arg Glu Ser Arg Arg Ile Leu Tyr Gln Asn Leu Asn Glu Pro Thr
            3455                3460                3465
Thr Trp Ser Leu Thr Ser Asp Arg Thr Arg Asn Trp Val Leu Gln
            3470                3475                3480
Gln Lys Ile Glu Gly Glu Thr Lys Glu Ser Asn Tyr Ala Lys Leu
            3485                3490                3495
Ile Glu Met Asn Gly Gly Gly Thr Gly Cys Asn His Glu Leu Glu
            3500                3505                3510
Met Ile Arg Gln Lys Leu Gln Cys Val Ala Ser Lys Leu Gln Val
            3515                3520                3525
Leu Pro Gln Lys Ala Ser Glu Arg Leu Gln Phe Glu Thr Ala Asp
            3530                3535                3540
Asp Glu Asp Phe Ile Trp Val Gln Glu Asn Ile Asp Glu Ile Ile
            3545                3550                3555
Leu Gln Leu Gln Lys Leu Thr Gly Gln Gly Glu Glu Pro Ser
            3560                3565                3570
Leu Val Ser Pro Ser Thr Ser Cys Gly Ser Leu Thr Glu Arg Leu
            3575                3580                3585
Leu Arg Gln Asn Ala Glu Leu Thr Gly His Ile Ser Gln Leu Thr
            3590                3595                3600
Glu Glu Lys Asn Asp Leu Arg Asn Met Val Met Lys Leu Glu Glu
            3605                3610                3615
Gln Ile Arg Trp Tyr Arg Gln Thr Gly Ala Gly Arg Asp Asn Ser
            3620                3625                3630
Ser Arg Phe Ser Leu Asn Gly Gly Ala Asn Ile Glu Ala Ile Ile
            3635                3640                3645
Ala Ser Glu Lys Glu Val Trp Asn Arg Glu Lys Leu Thr Leu Gln
            3650                3655                3660
Lys Ser Leu Lys Arg Ala Glu Ala Glu Val Tyr Lys Leu Lys Ala
            3665                3670                3675
Glu Leu Arg Asn Asp Ser Leu Leu Gln Thr Leu Ser Pro Asp Ser
            3680                3685                3690
Glu His Val Thr Leu Lys Arg Ile Tyr Gly Lys Tyr Leu Arg Ala
            3695                3700                3705
Glu Ser Phe Arg Lys Ala Leu Ile Tyr Gln Lys Lys Tyr Leu Leu
            3710                3715                3720
Leu Leu Leu Gly Gly Phe Gln Glu Cys Glu Asp Ala Thr Leu Ala
            3725                3730                3735
Leu Leu Ala Arg Met Gly Gly Gln Pro Ala Phe Thr Asp Leu Glu
            3740                3745                3750
Val Ile Thr Asn Arg Pro Lys Gly Phe Thr Arg Phe Arg Ser Ala
            3755                3760                3765
Val Arg Val Ser Ile Ala Ile Ser Arg Met Lys Phe Leu Val Arg
            3770                3775                3780
Arg Trp His Arg Val Thr Gly Ser Val Ser Ile Asn Ile Asn Arg
            3785                3790                3795
```

```
Asp Gly Phe Gly Leu Asn Gln Gly Ala Glu Lys Thr Asp Ser Phe
    3800            3805                3810

Tyr His Ser Ser Gly Gly Leu Glu Leu Tyr Gly Glu Pro Arg His
    3815            3820                3825

Thr Thr Tyr Arg Ser Arg Ser Asp Leu Asp Tyr Ile Arg Ser Pro
    3830            3835                3840

Leu Pro Phe Gln Asn Arg Tyr Pro Gly Thr Pro Ala Asp Phe Asn
    3845            3850                3855

Pro Gly Ser Leu Ala Cys Ser Gln Leu Gln Asn Tyr Asp Pro Asp
    3860            3865                3870

Arg Ala Leu Thr Asp Tyr Ile Thr Arg Leu Glu Ala Leu Gln Arg
    3875            3880                3885

Arg Leu Gly Thr Ile Gln Ser Gly Ser Thr Thr Gln Phe His Ala
    3890            3895                3900

Gly Met Arg Arg
    3905

<210> SEQ ID NO 3
<211> LENGTH: 101
<212> TYPE: DNA
<213> ORGANISM: Homo sapiens

<400> SEQUENCE: 3
agtccttaca gaggatgctc ttaaatccct agaaaatcag acatacttca ratcttttga      60
agaaaatggc aaaggttcca taattaattt ggaaacaagg t                        101
```